US011786529B2

(12) United States Patent
Hilger et al.

(10) Patent No.: US 11,786,529 B2
(45) Date of Patent: Oct. 17, 2023

(54) TREATMENT OF INDOLENT OR AGGRESSIVE B-CELL LYMPHOMAS USING A COMBINATION COMPRISING BTK INHIBITORS

(71) Applicant: BEIGENE SWITZERLAND GMBH, Zürich (CH)

(72) Inventors: James Hilger, Zürich (CH); Xiaoping Zhang, Zürich (CH); Shibao Feng, Zürich (CH); Sunhee Ro, Zürich (CH); Jane Huang, Zürich (CH)

(73) Assignee: BEIGENE SWITZERLAND GMBH, Basel (CH)

(*) Notice: Subject to any disclaimer, the term of this patent is extended or adjusted under 35 U.S.C. 154(b) by 180 days.

(21) Appl. No.: 16/766,803

(22) PCT Filed: Nov. 29, 2018

(86) PCT No.: PCT/US2018/063068
§ 371 (c)(1),
(2) Date: May 26, 2020

(87) PCT Pub. No.: WO2019/108795
PCT Pub. Date: Jun. 6, 2019

(65) Prior Publication Data
US 2020/0368237 A1 Nov. 26, 2020

Related U.S. Application Data

(60) Provisional application No. 62/592,111, filed on Nov. 29, 2017.

(51) Int. Cl.
*A61K 31/519* (2006.01)
*C07K 16/28* (2006.01)
*A61K 9/00* (2006.01)

(52) U.S. Cl.
CPC ........ *A61K 31/519* (2013.01); *C07K 16/2818* (2013.01); *A61K 9/0019* (2013.01)

(58) Field of Classification Search
CPC .... A61K 31/4162; A61K 31/519; A61P 35/00
See application file for complete search history.

(56) References Cited

U.S. PATENT DOCUMENTS

| 5,624,821 | A  | 4/1997  | Winter et al.     |
|-----------|----|---------|-------------------|
| 5,629,204 | A  | 5/1997  | Honjo et al.      |
| 5,648,260 | A  | 7/1997  | Winter et al.     |
| 5,698,520 | A  | 12/1997 | Honjo et al.      |
| 5,994,514 | A  | 11/1999 | Jardieu et al.    |
| 6,165,745 | A  | 12/2000 | Ward et al.       |
| 6,194,551 | B1 | 2/2001  | Idusogie et al.   |
| 6,528,624 | B1 | 3/2003  | Idusogie et al.   |
| 6,632,927 | B2 | 10/2003 | Adair et al.      |
| 6,737,056 | B1 | 5/2004  | Presta            |
| 6,808,710 | B1 | 10/2004 | Wood et al.       |
| 6,936,704 | B1 | 8/2005  | Freeman et al.    |
| 7,029,674 | B2 | 4/2006  | Carreno et al.    |
| 7,038,013 | B2 | 5/2006  | Freeman et al.    |
| 7,101,550 | B2 | 9/2006  | Wood et al.       |
| 7,122,637 | B2 | 10/2006 | Presta            |
| 7,297,775 | B2 | 11/2007 | Idusogie et al.   |
| 7,317,091 | B2 | 1/2008  | Lazar et al.      |
| 7,332,581 | B2 | 2/2008  | Presta            |
| 7,335,742 | B2 | 2/2008  | Presta            |
| 7,355,008 | B2 | 4/2008  | Stavenhagen et al.|
| 7,364,731 | B2 | 4/2008  | Idusogie et al.   |
| 7,371,826 | B2 | 5/2008  | Presta            |
| 7,393,848 | B2 | 7/2008  | Currie et al.     |
| 7,414,171 | B2 | 8/2008  | Honjo et al.      |
| 7,416,726 | B2 | 8/2008  | Ravetch           |
| 7,488,802 | B2 | 2/2009  | Collins et al.    |
| 7,514,444 | B2 | 4/2009  | Honigberg et al.  |
| 7,563,869 | B2 | 7/2009  | Honjo et al.      |
| 7,595,048 | B2 | 9/2009  | Honjo et al.      |
| 7,597,889 | B1 | 10/2009 | Armour et al.     |
| 7,608,429 | B2 | 10/2009 | Reilly et al.     |
| 7,635,757 | B2 | 12/2009 | Freeman et al.    |
| 7,638,492 | B2 | 12/2009 | Wood et al.       |
| 7,655,783 | B2 | 2/2010  | Reilly et al.     |

(Continued)

FOREIGN PATENT DOCUMENTS

| CN | 1753912 A | 3/2006 |
|----|-----------|--------|
| CN | 1771231 A | 5/2006 |

(Continued)

OTHER PUBLICATIONS

Wenzel et al., (Leukemia vol. 27 pp. 1381-1390 published 2013). (Year: 2013).*
Extended European Search Report for European Application No. 14787642.9, dated Jan. 26, 2016, 5 pages.
International Search Report and Written Opinion for International Application No. PCT/CN2014/075943, dated Jul. 18, 2014, 10 pages.
Extended European Search Report for European Application No. 17841172.4, dated Mar. 5, 2020, 6 pages.
International Search Report and Written Opinion for International Application No. PCT/IB2017/054955, dated Sep. 10, 2018, 16 pages.

(Continued)

*Primary Examiner* — Theodore R. Howell
*Assistant Examiner* — George W Kosturko
(74) *Attorney, Agent, or Firm* — COOLEY LLP

(57) ABSTRACT

Disclosed herein is a method for the prevention, delay of progression or treatment of indolent or aggressive B-cell lymphomas in an individual in need thereof, comprising administering a Btk inhibitor (in particularly (S)-7-(1-actyloylpiperidin-4-yl)-2-(4-phenoxyphenyl)-4,5,6,7-tetrahydropyrazolo-[1,5-a]pyrimidine-3-carboxamide or a pharmaceutically acceptable salt thereof) in combination with an anti-PD-1 antibody. The potent and selective BTK inhibitor in combination with the anti-PD-1 antibody have a manageable toxicity profile in patients with indolent and aggressive lymphomas.

16 Claims, 7 Drawing Sheets
Specification includes a Sequence Listing.

(56) References Cited

U.S. PATENT DOCUMENTS

| | | |
|---|---|---|
| 7,670,600 B2 | 3/2010 | Dall'Acqua et al. |
| 7,718,662 B1 | 5/2010 | Chen et al. |
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,084,620 B2 | 12/2011 | Liu et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,246,955 B2 | 8/2012 | Honjo et al. |
| 8,354,509 B2 | 1/2013 | Carven et al. |
| 8,552,154 B2 | 10/2013 | Freeman et al. |
| 8,617,546 B2 | 12/2013 | Kang et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,911,726 B2 | 12/2014 | Takahashi et al. |
| 8,945,561 B2 | 2/2015 | Davis |
| 9,067,999 B1 | 6/2015 | Honjo et al. |
| 9,073,994 B2 | 7/2015 | Honjo et al. |
| 9,084,776 B2 | 7/2015 | Korman et al. |
| 9,139,653 B1 | 9/2015 | Campbell et al. |
| 9,175,082 B2 | 11/2015 | Zhou et al. |
| 9,217,034 B2 | 12/2015 | Li et al. |
| 9,447,106 B2 | 9/2016 | Wang et al. |
| 9,492,540 B2 | 11/2016 | Korman et al. |
| 9,556,188 B2 | 1/2017 | Wang et al. |
| 9,624,298 B2 | 4/2017 | Nastri et al. |
| 9,834,606 B2 | 12/2017 | Li et al. |
| 9,920,123 B2 | 3/2018 | Irving et al. |
| 9,988,450 B2 | 6/2018 | Li et al. |
| 10,005,782 B2 | 6/2018 | Wang et al. |
| 10,058,609 B2 | 8/2018 | Zhou et al. |
| 10,487,147 B2 | 11/2019 | Nastri et al. |
| 10,519,235 B2 | 12/2019 | Li et al. |
| 10,544,225 B2 | 1/2020 | Li et al. |
| 10,550,185 B2 | 2/2020 | Bernett et al. |
| 10,570,139 B2 | 2/2020 | Wang et al. |
| 10,793,632 B2 | 10/2020 | Bernett et al. |
| 10,858,435 B2 | 12/2020 | Finlay |
| 10,864,203 B2 | 12/2020 | Song et al. |
| 10,927,117 B2 | 2/2021 | Wang et al. |
| 11,142,528 B2 | 10/2021 | Wang et al. |
| 11,186,637 B2 | 11/2021 | Li et al. |
| 11,202,782 B2 | 12/2021 | Wang et al. |
| 11,203,637 B2 | 12/2021 | Zhang et al. |
| 11,377,449 B2 | 7/2022 | Wang et al. |
| 11,512,132 B2 | 11/2022 | Li et al. |
| 11,555,038 B2 | 1/2023 | Guo et al. |
| 2002/0094989 A1 | 7/2002 | Hale et al. |
| 2004/0038339 A1 | 2/2004 | Kufer et al. |
| 2005/0064514 A1 | 3/2005 | Stavenhagen et al. |
| 2005/0202028 A1 | 9/2005 | Ledbetter et al. |
| 2006/0121032 A1 | 6/2006 | Dahiyat et al. |
| 2006/0134105 A1 | 6/2006 | Lazar et al. |
| 2006/0178367 A1 | 8/2006 | Currie et al. |
| 2006/0183746 A1 | 8/2006 | Currie et al. |
| 2006/0263856 A1 | 11/2006 | Gillies et al. |
| 2007/0160597 A1 | 7/2007 | Lazar et al. |
| 2008/0076921 A1 | 3/2008 | Honigberg et al. |
| 2008/0139582 A1 | 6/2008 | Honigberg et al. |
| 2009/0068175 A1 | 3/2009 | Lazar et al. |
| 2009/0105209 A1 | 4/2009 | Dewdney et al. |
| 2009/0155256 A1 | 6/2009 | Black et al. |
| 2009/0217401 A1 | 8/2009 | Korman et al. |
| 2009/0318441 A1 | 12/2009 | Brain et al. |
| 2010/0004231 A1 | 1/2010 | Dewdney et al. |
| 2010/0016296 A1 | 1/2010 | Singh et al. |
| 2010/0016301 A1 | 1/2010 | Dewdney et al. |
| 2010/0029610 A1 | 2/2010 | Singh et al. |
| 2010/0035841 A1 | 2/2010 | Jankowski et al. |
| 2010/0087464 A1 | 4/2010 | Mi et al. |
| 2010/0105676 A1 | 4/2010 | Liu et al. |
| 2010/0144705 A1 | 6/2010 | Miller |
| 2010/0151492 A1 | 6/2010 | Ahmed et al. |
| 2010/0160292 A1 | 6/2010 | Whitney et al. |
| 2010/0160303 A1 | 6/2010 | Liu et al. |
| 2010/0197924 A1 | 8/2010 | Gould et al. |
| 2010/0222325 A1 | 9/2010 | Berthel et al. |
| 2010/0249092 A1 | 9/2010 | Singh et al. |
| 2010/0254905 A1 | 10/2010 | Honigberg et al. |
| 2010/0317834 A1 | 12/2010 | Lazar et al. |
| 2011/0008369 A1 | 1/2011 | Finnefrock et al. |
| 2011/0052584 A1 | 3/2011 | Ravetch |
| 2011/0054151 A1 | 3/2011 | Lazar et al. |
| 2011/0118233 A1 | 5/2011 | Blomgren et al. |
| 2011/0124640 A1 | 5/2011 | Liu et al. |
| 2011/0159023 A1 | 6/2011 | Langermann |
| 2011/0171215 A1 | 7/2011 | Davis et al. |
| 2011/0171220 A1 | 7/2011 | Davis et al. |
| 2011/0177088 A1 | 7/2011 | Olive et al. |
| 2011/0195068 A1 | 8/2011 | Langermann et al. |
| 2011/0224235 A1 | 9/2011 | Honigberg et al. |
| 2011/0271358 A1 | 11/2011 | Freeman et al. |
| 2011/0287032 A1 | 11/2011 | Lazar et al. |
| 2011/0301145 A1 | 12/2011 | Barbosa, Jr. et al. |
| 2012/0028981 A1 | 2/2012 | Miller |
| 2012/0040961 A1 | 2/2012 | Gray et al. |
| 2012/0053189 A1 | 3/2012 | Loury |
| 2012/0058996 A1 | 3/2012 | Liu et al. |
| 2012/0076726 A1 | 3/2012 | Gellerfors et al. |
| 2012/0077832 A1 | 3/2012 | Witowski et al. |
| 2012/0082702 A1 | 4/2012 | DeLucca et al. |
| 2012/0129852 A1 | 5/2012 | Duan et al. |
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2012/0237522 A1 | 9/2012 | Kang et al. |
| 2012/0251531 A1 | 10/2012 | Baehner et al. |
| 2013/0004514 A1 | 1/2013 | Zahn et al. |
| 2013/0079327 A1 | 3/2013 | Yamamoto et al. |
| 2013/0089541 A1 | 4/2013 | D'Angelo et al. |
| 2013/0096118 A1 | 4/2013 | Liu et al. |
| 2013/0116213 A1 | 5/2013 | Cha et al. |
| 2013/0259868 A1 | 10/2013 | Roschke et al. |
| 2013/0261103 A1 | 10/2013 | Currie et al. |
| 2013/0281432 A1 | 10/2013 | Currie et al. |
| 2013/0309250 A1 | 11/2013 | Cogswell et al. |
| 2014/0044738 A1 | 2/2014 | Langermann et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162316 A1 | 6/2014 | O'Neil et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2014/0243504 A1 | 8/2014 | Davis et al. |
| 2014/0245468 A1 | 8/2014 | McWhirter et al. |
| 2014/0271642 A1 | 9/2014 | Murphy et al. |
| 2014/0314714 A1 | 10/2014 | Honjo et al. |
| 2014/0341902 A1 | 11/2014 | Maecker et al. |
| 2014/0356322 A1 | 12/2014 | Crews et al. |
| 2014/0356363 A1 | 12/2014 | Zhou et al. |
| 2014/0377269 A1 | 12/2014 | Mabry et al. |
| 2015/0044231 A1 | 2/2015 | Kjaergaard et al. |
| 2015/0079109 A1* | 3/2015 | Li .................. A61P 31/12 530/387.3 |
| 2015/0118222 A1* | 4/2015 | Levy .................. A61K 31/519 424/130.1 |
| 2015/0125444 A1 | 5/2015 | Tsui et al. |
| 2015/0210763 A1 | 7/2015 | Kuramochi et al. |
| 2015/0259354 A1* | 9/2015 | Wang .................. A61P 29/00 514/210.16 |
| 2015/0315274 A1 | 11/2015 | Li et al. |
| 2015/0337053 A1 | 11/2015 | McCarthy et al. |
| 2015/0353631 A1 | 12/2015 | Buttini et al. |
| 2016/0045607 A1 | 2/2016 | Crew et al. |
| 2016/0083392 A1 | 3/2016 | Wang et al. |
| 2016/0272639 A1 | 9/2016 | Crew et al. |

(56) References Cited

U.S. PATENT DOCUMENTS

| | | |
|---|---|---|
| 2017/0008904 A1 | 1/2017 | Crew et al. |
| 2017/0044260 A1 | 2/2017 | Baruah et al. |
| 2017/0073349 A1 | 3/2017 | Wang et al. |
| 2018/0037655 A1 | 2/2018 | Hegde et al. |
| 2018/0050021 A1 | 2/2018 | Ciulli et al. |
| 2018/0072711 A1 | 3/2018 | Crew et al. |
| 2018/0200273 A1 | 7/2018 | Nguyen et al. |
| 2018/0215825 A1 | 8/2018 | Li et al. |
| 2018/0251466 A1 | 9/2018 | Wang et al. |
| 2018/0251551 A1 | 9/2018 | Li et al. |
| 2019/0111142 A1 | 4/2019 | Nguyen et al. |
| 2019/0127359 A1 | 5/2019 | Crews et al. |
| 2019/0169201 A1 | 6/2019 | Wang et al. |
| 2019/0183913 A1 | 6/2019 | Nguyen et al. |
| 2020/0030339 A1 | 1/2020 | Wang et al. |
| 2020/0069666 A1 | 3/2020 | Song et al. |
| 2020/0148690 A1 | 5/2020 | Wang et al. |
| 2020/0181150 A1 | 6/2020 | Wang et al. |
| 2020/0216535 A1 | 7/2020 | Li et al. |
| 2020/0283527 A1 | 9/2020 | Li et al. |
| 2020/0392131 A1 | 12/2020 | Crew et al. |
| 2021/0040213 A1 | 2/2021 | Song et al. |
| 2021/0130363 A1 | 5/2021 | Wang et al. |
| 2021/0147543 A1 | 5/2021 | Wang et al. |
| 2021/0161921 A1 | 6/2021 | Nguyen et al. |
| 2021/0228553 A1 | 7/2021 | Song et al. |
| 2021/0230274 A1 | 7/2021 | Li et al. |
| 2021/0275530 A1 | 9/2021 | Hu et al. |
| 2021/0332049 A1 | 10/2021 | Guo et al. |
| 2022/0119524 A1 | 4/2022 | Li et al. |
| 2022/0135675 A1 | 5/2022 | Zhang et al. |
| 2022/0241285 A1 | 8/2022 | Wang et al. |
| 2022/0249491 A1 | 8/2022 | Qiu et al. |
| 2022/0274994 A1 | 9/2022 | Wang et al. |
| 2022/0281876 A1 | 9/2022 | Wang et al. |
| 2022/0281881 A1 | 9/2022 | Wang et al. |
| 2022/0298163 A1 | 9/2022 | Wang et al. |
| 2022/0340583 A1 | 10/2022 | Wang et al. |
| 2022/0340584 A1 | 10/2022 | Wang et al. |
| 2023/0013862 A1 | 1/2023 | Wang et al. |

FOREIGN PATENT DOCUMENTS

| | | |
|---|---|---|
| CN | 101104640 | 1/2008 |
| CN | 101213297 A | 7/2008 |
| CN | 101355965 A | 1/2009 |
| CN | 101899114 | 12/2010 |
| CN | 102245640 A | 11/2011 |
| CN | 102264762 A | 11/2011 |
| CN | 102656173 A | 9/2012 |
| CN | 104736569 A | 6/2015 |
| CN | 104884458 A | 9/2015 |
| CN | 105531288 A | 4/2016 |
| CN | 106103485 A | 11/2016 |
| CN | 107011441 A | 8/2017 |
| CN | 107090041 A | 8/2017 |
| CN | 108136044 A | 6/2018 |
| CN | 108601764 A | 9/2018 |
| CN | 109475567 A | 3/2019 |
| GB | 1412017 | 10/1975 |
| JP | H 07-278148 A | 10/1995 |
| JP | 2006510582 A | 3/2006 |
| JP | 2008544755 A | 12/2008 |
| JP | 2009155338 A | 7/2009 |
| JP | 2010504324 A | 2/2010 |
| JP | 2010528993 A | 8/2010 |
| JP | 2012511329 A | 5/2012 |
| JP | 2012254092 A | 12/2012 |
| JP | 2016521273 A | 7/2016 |
| KR | 20080011428 A | 2/2008 |
| KR | 20100054780 A | 5/2010 |
| WO | WO 94/29351 | 12/1994 |
| WO | WO 2001/016138 A1 | 3/2001 |
| WO | WO 2001/019829 A2 | 3/2001 |
| WO | WO-2002020740 | 3/2002 |
| WO | WO 2002/050071 A1 | 6/2002 |
| WO | WO 2002/072576 A1 | 9/2002 |
| WO | WO 2003/004497 A1 | 1/2003 |
| WO | WO 2004/017908 A2 | 3/2004 |
| WO | WO 2005/005429 A1 | 1/2005 |
| WO | WO 2005/011597 A2 | 2/2005 |
| WO | WO 2005/014599 A1 | 2/2005 |
| WO | WO 2005/047290 A2 | 5/2005 |
| WO | WO 2005/077981 | 8/2005 |
| WO | WO 2006/053121 A2 | 5/2006 |
| WO | WO 2006/065946 A1 | 6/2006 |
| WO | WO 2006/084015 | 8/2006 |
| WO | WO 2006/099075 A2 | 9/2006 |
| WO | WO 2006/121168 | 11/2006 |
| WO | WO-2006133396 A2 | 12/2006 |
| WO | WO 2007/005874 | 1/2007 |
| WO | WO 2007/026720 A1 | 3/2007 |
| WO | WO 2007/026950 A1 | 3/2007 |
| WO | WO 2007/027594 A1 | 3/2007 |
| WO | WO 2007/027729 A1 | 3/2007 |
| WO | WO 2007/067444 | 6/2007 |
| WO | WO 2007/087068 A2 | 8/2007 |
| WO | WO 2007/136572 | 11/2007 |
| WO | WO 2007/136790 A2 | 11/2007 |
| WO | WO 2008/033834 A1 | 3/2008 |
| WO | WO 2008/033854 A1 | 3/2008 |
| WO | WO 2008/033857 A2 | 3/2008 |
| WO | WO 2008/039218 A2 | 4/2008 |
| WO | WO 2008/054827 A2 | 5/2008 |
| WO | WO 2008/144253 A1 | 11/2008 |
| WO | WO 2008/145142 | 12/2008 |
| WO | WO 2008/156712 | 12/2008 |
| WO | WO 2009/039397 A2 | 3/2009 |
| WO | WO 2009/051822 A1 | 4/2009 |
| WO | WO 2009/077334 A1 | 6/2009 |
| WO | WO 2009/098144 A1 | 8/2009 |
| WO | WO-2009100309 A2 | 8/2009 |
| WO | WO 2009/158571 A1 | 12/2009 |
| WO | WO 2010/000633 A1 | 1/2010 |
| WO | WO 2010/006947 A1 | 1/2010 |
| WO | WO 2010/006970 A1 | 1/2010 |
| WO | WO 2010/028236 A1 | 3/2010 |
| WO | WO 2010/051549 A1 | 5/2010 |
| WO | WO 2010/065898 A2 | 6/2010 |
| WO | WO 2010/068788 A1 | 6/2010 |
| WO | WO 2010/068806 A1 | 6/2010 |
| WO | WO 2010/068810 A2 | 6/2010 |
| WO | WO 2010/077634 | 7/2010 |
| WO | WO 2010/089411 | 8/2010 |
| WO | WO 2010/122038 A1 | 10/2010 |
| WO | WO 2011/006074 A1 | 1/2011 |
| WO | WO 2011/140488 A1 | 11/2011 |
| WO | WO 2011/153514 A2 | 12/2011 |
| WO | WO 2012/020008 A1 | 2/2012 |
| WO | WO-2012083370 A1 | 6/2012 |
| WO | WO 2012/135408 | 10/2012 |
| WO | WO 2012/135801 A1 | 10/2012 |
| WO | WO 2012/143522 A1 | 10/2012 |
| WO | WO 2012/145493 | 10/2012 |
| WO | WO-2012130831 A1 | 10/2012 |
| WO | WO 2012/156334 A1 | 11/2012 |
| WO | WO 2012/158795 A1 | 11/2012 |
| WO | WO 2012/175692 | 12/2012 |
| WO | WO 2013/079174 | 6/2013 |
| WO | WO-2013106643 A2 | 7/2013 |
| WO | WO 2013/173223 | 11/2013 |
| WO | WO 2013/181634 | 12/2013 |
| WO | WO 2014/055897 | 4/2014 |
| WO | WO 2014/100079 | 6/2014 |
| WO | WO-2014108452 A1 | 7/2014 |
| WO | WO 2014/173289 A1 | 10/2014 |
| WO | WO 2015/035606 | 3/2015 |
| WO | WO 2015/061752 A1 | 4/2015 |
| WO | WO-2015112900 A1 | 7/2015 |
| WO | WO 2016/000619 | 1/2016 |
| WO | WO-2016008411 A1 | 1/2016 |
| WO | WO-2016024228 A1 | 2/2016 |
| WO | WO-2016025720 A1 | 2/2016 |
| WO | WO-2016064649 A1 | 4/2016 |

(56) References Cited

FOREIGN PATENT DOCUMENTS

| WO | WO 2016/087994 A1 | 6/2016 |
|---|---|---|
| WO | WO 2016/100914 A1 | 6/2016 |
| WO | WO 2016/105582 A1 | 6/2016 |
| WO | WO-2016146985 A1 | 9/2016 |
| WO | WO-2016149668 A1 | 9/2016 |
| WO | WO-2016149989 A1 | 9/2016 |
| WO | WO-2016197032 A1 | 12/2016 |
| WO | WO-2016197114 A1 | 12/2016 |
| WO | WO-2017011590 A1 | 1/2017 |
| WO | WO-2017025016 A1 | 2/2017 |
| WO | WO-2017030814 A1 | 2/2017 |
| WO | WO 2017/046746 A1 | 3/2017 |
| WO | WO 2017/059224 A2 | 4/2017 |
| WO | WO-2017079267 A1 | 5/2017 |
| WO | WO-2017182418 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197056 A1 | 11/2017 |
| WO | WO-2017201449 A1 | 11/2017 |
| WO | WO-2017211924 A1 | 12/2017 |
| WO | WO-2017214491 A1 | 12/2017 |
| WO | WO 2018/033135 | 2/2018 |
| WO | WO 2018/033853 | 2/2018 |
| WO | WO-2018033556 A1 | 2/2018 |
| WO | WO-2018071606 A1 | 4/2018 |
| WO | WO-2018098275 A1 | 5/2018 |
| WO | WO-2018098280 A1 | 5/2018 |
| WO | WO 2018/137681 | 8/2018 |
| WO | WO 2018/193105 A1 | 10/2018 |
| WO | WO-2019001417 A1 | 1/2019 |
| WO | WO 2019/034009 | 2/2019 |
| WO | WO 2019/108795 | 6/2019 |
| WO | WO-2019157353 A1 | 8/2019 |
| WO | WO-2019183226 A1 | 9/2019 |
| WO | WO-2020249001 A1 | 12/2020 |
| WO | WO-2020249002 A1 | 12/2020 |
| WO | WO-2021018018 A1 | 2/2021 |

OTHER PUBLICATIONS

Extended European Search Report for European Application No. 17841107.0, dated Feb. 21, 2020, 12 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/100145, dated Nov. 14, 2018, 8 pages.
International Search Report and Written Opinion for International Application No. PCT/US2018/063068, dated Feb. 27, 2019, 8 pages.
Bradshaw, J. M., "The Src, Syk, and Tec family kinases: Distinct types of molecular switches," Cellular Signalling, 22:1175-1184 (2010).
Kersseboom, R. et al., "Constitutive activation of Bruton's tyrosine kinase induces the formation of autoreactive IgM plasma cells," Eur. J. Immunol. 40:2643-2654, 2010.
Luo, J et al., "Modern Physical Pharmaceutics Theory and Practice," Shang Hai Science and Technology Literature Publishing House, Apr. 2005, pp. 293-295.
Caira, E. D. et al., "Crystalline polymorphism of organic compounds," Topics in Current Chemistry, vol. 198, 1998, pp. 163-208.
Conley, M. E. et al., "Primary B Cell Immunodeficiencies: Comparisons and Contrasts," Annu. Rev. Immunol., 27:199-227 (2009).
Davis, R. E. et al., "Chronic active B-cell-receptorsignalling in diffuse large B-cell lymphoma," Nature, 463:88-92 (2010).
Gurcan, H. M. et al., "A review of the current use of rituximab in autoimmune diseases," Int. Immunopharmacol., 9:10-25 (2009).
Hackam, D. G. et al., "Translation of research evidence from animals to humans," JAMA, 296(14):1731-1732 (2006).
Humphries, L. A. et al., "Tec Kinases Mediate Sustained Calcium Influx via Site-specific Tyrosine Phosphorylation of the Phospholipase Cγ Src Homology 2-Src Homology 3 Linker," J. Biol. Chem. 279(36):37651-37661 (2004).
Jenkins, S. M. et al., "Substituent variation in azabicydic triazole- and tetrazole-based muscarinic receptor ligands," J. Med. Chem., 35(13):2392-2406 (1992).
Jordan, V. C., "Tamoxifen: A most unlikely pioneering medicine," Nature Reviews: Drug Discovery, 2:205-213 (2003).
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Mohamed, A. J. et al., "Bruton's tyrosine kinase (Btk): function, regulation, and transformation with special emphasis on the PH domain," Immunol. Rev., 228:58-73 (2009).
Pan, Z, "Bruton's tyrosine kinase as a drug discovery target," Drug News Perspect, 21(7):357-362 (2008).
Rokosz, L. L. et al., "Kinase inhibitors as drugs for chronic inflammatory and immunological diseases: progress and challenges," Expert Opin. Ther. Targets, 12(7):883-903 (2008).
Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Uckun, F. M. et al., "Bruton's tyrosine kinase as a new therapeutic target," Anti-Cancer Agents in Medicinal Chemistry, 7(6):624-632 (2007).
Vetrie, D. et al., "The gene involved in X-linked agammaglobulinaemia is a member of the src family of protein-tyrosine kinases," Nature, 361:226-233 (1993).
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).
International Search Report and Written Opinion for International Application No. PCT/CN2013/083467, dated Jun. 16, 2014, 9 pages.
Supplementary Partial European Search Report for European Application No. 13893636.4, dated Feb. 28, 2017, 13 pages.
Extended European Search Report for European Application No. 15815646.3, dated Dec. 21, 2017, 10 pages.
International Search Report and Written Opinion for International Application No. PCT/CN2015/083066, dated Sep. 24, 2015, 8 pages.
European Search Report for European Application No. 16167542.6, dated Nov. 14, 2016, 5 pages.
Abdiche et al., "Assessing kinetic and epitopic diversity across orthogonal monoclonal antibody generation platforms." mABs (Feb.-Mar. 2016); 8(2):264-277.
Arlauckas, S.P. et al., "In vivo imaging reveals a tumor-associated macrophage-mediated resistance pathway in anti-PD-1 therapy," Sci. Transl. Med., 9, eaal3604 (May 2017).
Araki, K. et al., "Programmed cell death 1-directed immunotherapy for enhancing T-cell function," Cold Spring Harbor Symposia on Quantitative Biology, vol. LXXVIII, 239-247 (2013).

(56) References Cited

OTHER PUBLICATIONS

Ahmadzadeh, M. et al., "Tumor antigen-specific CD8 T cells infiltrating the tumor express high levels of PD-1 and are functionally impaired," Blood. Aug. 20, 2009;114(8):1537-1544. doi: 10.1182/blood-2008-12-195792. Epub May 7, 2009.
Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).
Boyd et al., "Deep sequencing and human antibody repertoire analysis." Current Opinion in Immunology (Jun. 2016); 40:103-109. Epub Apr. 8, 2016.
Brahmer, J. R. et al., "Safety and Activity of Anti-PD-L1 Antibody in Patients with Advanced Cancer," N Engl J Med. (Jun. 2012), 366(26):2455-2465.
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Brand, F-X et al., "Prospect for anti-HER2 receptor therapy in breast cancer," Anticancer Research, 26:463-470 (2006).
Casset, F. et al., "A peptide mimetic of an anti-CD4 monoclonal antibody by rational design," Biochemical and Biophysical Research Communications, 307:198-205 (2003).
Chia-Jui, Y. et al., Abstract of "Preliminary results of a phase 1A/1B study of BGB-A317, an anti-PD-1 monoclonal antibody (mAb), in patients with advanced hepatocellular carcinoma (HCC)," Annals of Oncology (2017).
Clynes, R. A. et al., "Inhibitory Fc receptors modulate in vivo cytoxicity against tumor targets," Nat. Med. 6(4):443-446 (Apr. 2000).
Conroy, et al., "Antibodies: From novel repertoires to defining and refining the structure of biologically important targets," Methods (Mar. 2017); 116:12-22. Epub Jan. 11, 2017.
Dahan, R. et al., "FcγRs Modulate the Anti-tumor Activity of Antibodies Targeting the PD-1/PD-L1 Axis," Cancer Cell (Sep. 2015), 28(3):285-95. doi: 10.1016/j.ccell.2015.08.004.
Damschroder et al., "Analysis of human and primate CD2 molecules by protein sequence and epitope mapping with anti-human CD2 antibodies," Mol Immunol. (Aug. 2004), 41(10):985-1000.
Dorfman, D. M. et al., "Programmed death-1 (PD-1) is a marker of germinal center-associated T Cells and angioimmunoblastic T-cell lymphoma," American Journal of Surgical Pathology, 30(7):802-810 (Jul. 2006).
Ferrara et al., "Recombinant renewable polyclonal antibodies." mABs (2015); 7(1):32-41.
Fuller, M. J. et al., "Immunotherapy of chronic hepatitis C virus infection with antibodies against programmed cell death-1 (PD-1)," Proceedings of the National Academy of Sciences, 110(37):15001-15006 (Sep. 2013).
Gelderman, K. A. et al., "Complement function in mAb-mediated cancer immunotherapy," Trends in Immunology, 25(3):158-164 (Mar. 2004).
Hamid, O. et al., "Safety and tumor responses with lambrolizumab (Anti-PD-1) in melanoma," New England Journal of Medicine, 369(2):134-144 (Jul. 2013).
InvivoGen Insight, "IgG-Fc Engineering for Therapeutic Use," Apr./May 2006, 4 pages.
James, L. K. et al., "Potential Mechanisms for IgG4 Inhibition of Immediate Hypersensitivity Reactions," Curr Allergy Asthma Rep. 2016; 16:23. Published online Feb. 1, 20168. doi: 10.1007/s11882-016-0600-2.
Jiao, Y. et al., "Advances in the research of the anti-cancer agent—Raf kinase inhibitor," Strait Pharmaceutical Journal, vol. 19, No. 8, 2007, pp. 1-5 (with English Abstract).
Khan et al., "Cross-neutralizing anti-HIV-1 human single chain variable fragments (scFvs) against CD4 binding site and N332 glycan identified from a recombinant phage library." Scientific Reports (2017); Article No. 45163, 12 pages.
Könitzer et al., "Generation of a highly diverse panel of antagonistic chicken monoclonal antibodies against the GIP receptor." mABs (Apr. 2017); 9(3):536-549. Epub Jan. 5, 2017.
Lund, J. et al., "Multiple interactions of IgG with its core oligosaccharide can modulate recognition by complement and human Fc gamma receptor I and influence the synthesis of its oligosaccharide chains," J Immunol., Dec. 1, 1996, 157(11):4963-4969.
Panka, D. J. et al., "Variable region framework differences result in decreased or increased affinity of variant anti-digoxin antibodies," May 1988, Proc. Natl. Acad. Sci. USA, 85:3080-3084.
Parola et al., "Integrating high-throughput screening and sequencing for monoclonal antibody discovery and engineering." Immunology (Jan. 2018); 153(1):31-41. Epub Oct. 30, 2017.
De Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).
Paul, W. E. (Ed.), Chap. 9, Structure and Function of Immunoglobulins, In: Fundamental Immunology, Third Edition, pp. 292-295, 1993.
Presta, L. G. et al., "Engineering therapeutic antibodies for improved function," Biochemical Society Transactions (2002) vol. 30, Part 4, pp. 487-490.
Rudikoff, S. et al., "Single amino acid substitution altering antigen-binding specificity," Proc. Natl. Acad. Sci. USA, 79:1979-1983 (Mar. 1982).
Sequence Alignment, 2014, 1 page.
Sheehan et al., "Phage and Yeast Display." Microbial. Spectr. (2015); 3(1):AID-0028-2014; 17 pages.
Shields, R. L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, 276(9):6591-6604 (2001).
Smith, K. G. et al., "FcγRIIB in autoimmunity and infection: evolutionary and therapeutic implications," Nat Rev Immunol. May 2010;10(5):328-43.
Stave, J. W. et al., "Antibody and antigen contact residues define epitope and paratope size and structure," The Journal of Immunology, vol. 191, Jan. 2013, pp. 1428-1435.
Strome, S. E. et al., "A Mechanistic Perspective of Monoclonal Antibodies in Cancer Therapy Beyond Target-Related Effects," The Oncologist, 2007; 12:1084-1095.
Sznol, M. et al., "Antagonist antibodies to PD-1 and B7-H1 (PD-L1) in the treatment of advanced human cancer," Clinical Cancer Research, 19(5):1021-1034 (Mar. 2013).
Van Regenmortel, M. H. V., "Development of a Preventive HIV Vaccine Requires Solving Inverse Problems Which Is Unattainable by Rational Vaccine Design." Front Immunol. (Jan. 2018); 8: 2009. eCollection 2017.
Wang, C. et al., "In Vitro Characterization of the Anti-PD-1 Antibody Nivolumab, BMS-936558, and In Vivo Toxicology in Non-Human Primates," Cancer Immunol Res; 2(9):846-856 (Sep. 2014).
Wherry, E. J., "T cell exhaustion," Nature Immunology 12(6):492-499 (2011). Published online May 18, 2011.
Wu, H. et al., "Humanization of a murine monoclonal antibody by simultaneous optimization of framework and CDR residues," Journal of Molecular Biology, 294(1):151-162 (Nov. 1999).
Xu, D. et al., "In vitro characterization of five humanized OKT3 effector function variant antibodies," Cell Immunol. Feb. 25, 2000;200(1):16-26.
Zhou et al., "Structural Repertoire of HIV-1-Neutralizing Antibodies Targeting the CD4 Supersite in 14 Donors." Cell (Jun. 2015); 161(6):1280-1292.
Lee et al., "Molecular-level analysis of the serum antibody repertoire in young adults before and after seasonal influenza vaccination." Nat Med. (Dec. 2016); 22(12):1456-1464. Epub Nov. 7, 2016.
Balar, A. et al., "Pembrolizumab (pembro) as first-line therapy for advanced/unresectable or metastatic urothelial cancer: Preliminary results from the phase 2 Keynote-052 study," Annals of Oncology 27 (Supplement 6): vi552-vi587, 2016.

(56) References Cited

OTHER PUBLICATIONS

Balbach, S. et al, "Pharmaceutical evaluation of early development candidates: 'The 100 mg-approach'," International Journal of Pharmaceutics, (2004), 275, pp. 1-12.

Beigene Co., Ltd., "Phase I Clinical Research to Evaluate Safety, Tolerability and Pharmacokinetics/Pharmacodynamics Characteristics of BTK Inhibitor, BGB-3111, in Treating Chinese B Lymphocyte Tumor Patients," [Online], May 2016, Retrieved from the Internet: http://www.chinadrugtrials.org.cn/clinicaltrials.searchlistdetail.dhtml, Retrieved on: Mar. 21, 2022, 17 pages (with Machine Translation).

Beigene, "Efficacy and Safety of Zanubrutinib in Relapsed or Refractory Chronic Lymphocytic Leukemia/Small Lymphocytic Lymphoma," [Online], Jul. 2017, Retrieved from the Internet: <https://clinicaltrials.gov/ct2/show/NCT03206918>, Retrieved on: Apr. 4, 2022, 7 pages.

Bellmunt, J. et al., "Keynote-045: open-label, phase II study of pembrolizumab versus investigator's choice of paclitaxel, docetaxel, or vinflunine for previously treated advanced urothelial cancer," Journal for ImmunoTherapy of Cancer, 2016, 4(Suppl. 2):91, Presented at 31st Society for Immunotherapy of Cancer Annual Meeting, Nov. 9-13, 2016, National Harbor, MD, 1 page.

Bellmunt, J. et al., "Pembrolizumab as Second-Line Therapy for Advanced Urothelial Carcinoma," N. Engl. J. Med., vol. 376, No. 11, Mar. 2017, pp. 1015-1026.

Bellmunt, J. et al., "Randomized Phase III Study Comparing Paclitaxel/Cisplatin/Gemcitabine and Gemcitabine/Cisplatin in Patients with Locally Advanced or Metastatic Urothelial Cancer Without Prior Systemic Therapy: EORTC Intergroup Study 30987," J Clin Oncol., Apr. 1, 2012;30(10):1107-1113.

Benson, D. M., Jr. et al., "The PD-1/PD-L1 axis modulates the natural killer cell versus multiple myeloma effect: a therapeutic target for CT-011, a novel monoclonal anti-PD-1 antibody," Blood, 116(13):2286-2294 (Sep. 2010).

Business Wire, "China NMPA Approves Tislelizumab in Non-Small Cell Lung Cancer and Hepatocellular Carcinoma," [Online], Retrieved from the Internet: businesswire.com/news/home/20210622006142/en, Jun. 2021, 7 pages.

Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.

De Toni, E. N. et al., "Tapering of Immunosuppression and Sustained Treatment With Nivolumab in a Liver Transplant Recipient," Gastroenterology, May 2017;152(6):1631-1633. doi: 10.1053/j.gastro.2017.01.063.

Desai, J. et al., "Updated safety, efficacy, and pharmacokinetics (PK) results from thephase I study of BGB-A317, an anti-programmed death-1 (PD-1) mAb in patients with advanced solid tumors," J. Immunother. Cancer, 2016; 4(Suppl 1):P154, 2 pages.

El-Khoueiry, A. B. et al., "Nivolumab in patients with advanced hepatocellular carcinoma (CheckMate 040): an open-label, non-comparative, phase 1/2 dose escalation and expansion trial," Lancet (Jun. 2017) vol. 389, No. 10088, pp. 2492-2502.

Extended European Search Report for European Application No. 18744173.8, dated Oct. 21, 2020, 12 pages.

Extended European Search Report for European Application No. 18823691.3, dated Feb. 22, 2021, 9 pages.

Galsky, M. D. et al., "Effectiveness of Adjuvant Chemotherapy for Locally Advanced Bladder Cancer," J Clin Oncol. Mar. 10, 2016;34(8):825-832.

Hirayama, Y., "Handbook for organic compound crystal—Principle and know-how," 2008, 28 pages.

"History of Changes for Study: NCT02690558. Phase 2 Study of Pembrolizumab in Combination With Gemcitabine and Cisplatin as Neoadjuvant Therapy," NCT02690558, Mar. 10, Mar. 2017, Retrieved from the Internet: URL:https://clinicaltrials.gov/ct2/history/NCT02690558?V_4=View#StudyPageTop, 5 pages.

International Search Report and Written Opinion for International Application No. PCT/CN2018/092827, dated Sep. 29, 2018, 14 pages.

International Search Report and Written Opinion for International Application No. PCT/CN2020/095352, dated Sep. 16, 2020, 23 pages.

International Search Report and Written Opinion for International Application No. PCT/CN2020/095353, dated Sep. 15, 2020, 23 pages.

International Search Report and Written Opinion for International Application No. PCT/US2019/017313, dated Jun. 25, 2019, 16 pages.

Jie, L., "Deuterated Drugs Progress," Chemical Engineering Design Communication Medicine and Chemical Industry, 2016, vol. 42, No. 4, p. 199.

Kourtzelis, I., et al., "The Dual Role of Complement in Cancer and its Implication in Anti-Tumor Therapy," Annals of Translational Medicine, 2016, vol. 4(14), 14 pages.

Kudo, M., Immune Checkpoint Blockade in Hepatocellular Carcinoma: 2017 Update, Liver Cancer, Nov. 2016; 6(1):1-12.

Kudo, M., "Immune Checkpoint Inhibition in Hepatocellular Carcinoma: Basics and Ongoing Clinical Trials," Oncology, 2017;92 Suppl 1:50-62. doi: 10.1159/000451016. Epub Feb. 2, 2017.

Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR2015, Philadelphia, PA, United States, Aug. 2015, 2 pages.

MedChemExpress, "Zanubrutinib," Product Data Sheet, Retrieved from the Internet: www.medchemexpress.com, Retrieved Aug. 17, 2021, 2 pages.

Office Action for Japanese Application No. 2019-508889, dated Jun. 22, 2021, 7 pages.

Pan, Z. et al., "Discovery of Selective Irreversible Inhibitors for Bruton's Tyrosine Kinase," ChemMedChem 2007, vol. 2, pp. 58-61.

Piao, C-Y et al., "Lamivudine treatment in patients with HBV-related hepatocellular carcinoma-using an untreated, matched control cohort," Acta Med. Okayama, vol. 59, No. 5, pp. 217-224 (2005).

Plimack, E. R. et al., "Pembrolizumab (MK-3475) for advanced urothelial cancer: Updated results and biomarker analysis from Keynote-012," J. Clin. Oncol., vol. 33, Issue 15 Suppl., May 2015, Abstract 4502, 2 pages.

Samonakis, D. N. et al., "Systemic treatment for hepatocellular carcinoma: Still unmet expectations," World J Hepatol., Jan. 2017; 9(2):80-90.

Sharma, P. et al., "Efficacy and safety of nivolumab monotherapy in metastatic urothelial cancer (mUC): Results from the phase I/II CheckMate 032 study," J. Clin. Oncol., vol. 34, No. 15 Suppl., May 2016, p. 4501.

Sharma, P. et al., "Nivolumab monotherapy in recurrent metastatic urothelial carcinoma (CheckMate 032): a multicentre, open-label, two-stage, multi-arm, phase 1/2 trial," Lancet Oncol., Nov. 2016, vol. 17, No. 11, pp. 1590-1598.

Shioji, Y., "Production Technology of Solid Preparations," Tokyo, CMC Publication, Jan. 27, 2003, Popular Edition, pp. 9 and 12-13.

Singhal, D. et al., "Drug polymorphism and dosage form design: a practical perspective," Advanced Drug Delivery Reviews, 56 (2004) pp. 335-347.

Takada, N., "Bulk Drug Form Screening and Selection at Drug Discovery Phase," Pharm Stage, Jan. 2007, vol. 6, No. 10, pp. 20-25.

Tam, C. S. et al., "A head-to-head Phase III study comparing zanubrutinib versus ibrutinib in patients with Waldenström macroglobulinemia," Future Oncology, vol. 14, No. 22, Sep. 2018, pp. 2229-2237.

Topalian, S. L., "Safety, Activity, and Immune Correlates of Anti-PD-1 Antibody in Cancer," N. Engl. J. Med., Jun. 2012; vol. 366, No. 26, pp. 2443-2454.

Wanich, N. et al., "High prevalence of hepatocellular carcinoma in patients with chronic hepatitis B infection in Thailand," Asian Pac J Cancer Prev, vol. 17, No. 6, pp. 2857-2860 (2016).

(56) References Cited

OTHER PUBLICATIONS

An, S. et al., "Small-molecule PROTACs: An emerging and promising approach for the development of targeted therapy drugs," EBioMedicine, Oct. 2018, vol. 36, pp. 553-562.
Ardley, H. C. et al., "E3 ubiquitin ligases," Essays Biochem., 2005, vol. 41, pp. 15-30.
Atkinson, B. T., "Tec regulates platelet activation by GPVI in the absence of Btk," Blood, Nov. 15, 2003, vol. 102, Issue 19, pp. 3592-3599.
Brinckerhoff, Courtenay C., "A Fresh Look At The Lead Compound Analysis," Pharma Patents, Foley & Lardner LLP, Jan. 22, 2019, 4 pages.
Buhimschi, A. D., "Targeting the C481S Ibrutinib-Resistance Mutation in Bruton's Tyrosine Kinase Using PROTAC-Mediated Degradation," Biochemistry, vol. 57, No. 26, Jul. 2018, pp. 3564-3575.
Buske, C et al., "A Head-To-Head Phase 3 Study Comparing BGB-3111 and Ibrutinib in Patients With Waldenström Macroglobulinemia," Hematological Oncology, 2017, vol. 35, pp. 422-423.
Byrd, J. C et al., "Acalabrutinib (ACP-196) in Relapsed Chronic Lymphocytic Leukemia," N. Engl. J. Med., 2016, vol. 374, pp. 323-332.
Byrd, J. C. et al., "Targeting BTK with Ibrutinib in Relapsed Chronic Lymphocytic Leukemia," N. Engl. J. Med., 2013, vol. 369, pp. 32-42.
Byrd, J. C. et al., "Three-year follow-up of treatment-naïve and previously treated patients with CLL and SLL receiving single-agent ibrutinib," Blood, Apr. 15, 2015, vol. 125, Issue 16, pp. 2497-2506.
Cermakova, K. et al., "Next-Generation Drugs and Probes for Chromatin Biology: From Targeted Protein Degradation to Phase Separation," Molecules, Aug. 2018, vol. 23, No. 1958, 26 pages.
Chen, J. et al., "Impact of Bruton's Tyrosine Kinase Inhibitors On Collagen-Induced Platelet Aggregation: a Pharmacokinetic/Pharmacodynamic Perspective," Eha Learning Center, Meeting Abstract 2016, 4 pages.
ClinicalTrials.gov Identifier: NCT03053440, A Study Comparing BGB-3111 and Ibrutinib in Subjects With Waldenström's Macroglobulinemia (WM) (Aug. 8, 2017), 12 pages.
ClinicalTrials.gov Identifier: NCT03145064, Study of BTK Inhibitor BGB-3111 in Subjects With Relapsed/Refractory Non-GCB Type Diffuse Large B Cell Lymphoma (May 5, 2017), 5 pages.
ClinicalTrials.gov Identifier: NCT03189524, A Study to Investigate Zanubrutinib in Chinese Participants With B-cell Lymphoma (Jun. 15, 2017), 5 pages.
ClinicalTrials.gov Identifier: NCT03206970, Study to Evaluate Efficacy and Safety of BGB-3111 in Participants With Relapsed or Refractory Mantle Cell Lymphoma (MCL) (Jul. 3, 2017), 6 pages.
Crews, C. M., "Inducing Protein Degradation as a Therapeutic Strategy," Jan. 2018, vol. 61(2), pp. 403-404.
Di Paolo et al., "Specific Btk inhibition suppresses B cell- and myeloid cell-mediated arthritis," Nat. Chem. Biol., 2011, vol. 7, pp. 41-50.
Dobrovolsky, D. et al., "Bruton tyrosine kinase degradation as a therapeutic strategy for cancer," Blood, Feb. 2019, vol. 133(9), pp. 952-961.
Eng, Melissa C., "United States: Selecting a Lead Compound: A Balancing Act In The Chemical Obviousness Inquiry," Monday, Mar. 8, 2018, 2 pages, retrieved from the Internet on Nov. 28, 2022, https://www.mondaq.com/unitedstates/patent/680778/selecting-a-lead-compound-a- balancing-act-in-the-chemical-obviousness-inquiry.
Grice, G. L. et al., "The Proteasome Distinguishes between Heterotypic and Homotypic Lysine-11-Linked Polyubiquitin Chains," Cell Rep., Jul. 2015, vol. 12(4), pp. 545-553.
Hu, Nan, et al. "BTK inhibitor BGB-3111 demonstrates anti-tumor activity in solid tumor models," Cancer Research, 2017, vol. 77, Supplement 13, pp. 2010-2010.

"International Nonproprietary Names for Pharmaceutical Substances (Inn)," Who Drug Information, 2017, vol. 31, No. 2, pp. 241-242, 355.
International Search Report and Written Opinion for International Application No. PCT/CN2020/103988, dated Oct. 27, 2020, 14 pages.
Kaur, V. et al., "Ibrutinib in CLL: a focus on adverse events, resistance, and novel approaches beyond ibrutinib," Ann. Hematol., 2017, vol. 96(7), pp. 1175-1184.
Komander, D. et al., "The ubiquitin code," Annu. Rev. Biochem., 2012, vol. 81, pp. 203-229.
Lebraud, H. et al., "Protein degradation: a validated therapeutic strategy with exciting prospects," Essays Biochem., Nov. 2017, vol. 61(5), pp. 517-527.
Li, et al., "Skin toxicities associated with epidermal growth factor receptor inhibitors," Target Oncol., 2009, vol. 4(2), pp. 107-119.
Lochmuller, C. H et al., "Chromatographic resolution of enantiomers selective review," J. Chromatogr., Oct. 1975, vol. 113, No. 3, pp. 283-302.
Lu, et al., "Hijacking the E3 ubiquitin ligase cereblon to efficiently target BRD4", Chem Biol, Jun. 18, 2015, vol. 22(6), pp. 755-763.
Lu, M. et al., "Discovery of a Keap1-dependent peptide PROTAC to knockdown Tau by ubiquitination-proteasome degradation pathway," Eur J Med Chem., Feb. 2018, vol. 146, pp. 251-259.
Melosky et al., "Supportive Care Treatments for Toxicities of Anti-EGFR and Other Targeted Agents," Curr. Oncol. 19 (Suppl 1), 2012, pp. 59-63.
Miller, Cary, "Prior Art Chemical Structures Must be More Than a 'Code Name'," Jones Day, Apr. 18, 2018, , 2 pages, retrieved online Nov. 28, 2022, <https://www.ptablitigationblog.com/prior-art-chemical-structures-must-be-more-than-a-code-name/>>https://www.ptablitigationblog.com/prior-art-chemical-structures-must-be-more-than-a-code-name/.>.
Neklesa, "Targeted protein degradation by PROTACs." Pharmacology & Therapeutics, Jun. 2017, vol. 174, pp. 138-144.
Noonan, Kevin E., "Novartis Pharmaceuticals Corp. v. West-Ward Pharmaceuticals Int'l (Fed. Cir. 2019)," Patent Docs, May 16, 2019, 3 pages, retrieved from the internet on Nov. 28, 2022, <https://www.patentdocs.org/2019/05/novartis- pharmaceuticals-corp-v-west-ward-pharmaceuticals-intl-fed-cir-2019.html.>.
Ottis, P. et al., "Assessing Different E3 Ligases for Small Molecule Induced Protein Ubiquitination and Degradation," ACS Chem. Biol., Oct. 2017, vol. 12(10), pp. 2570-2578.
Ottis, P. et al., "Proteolysis-Targeting Chimeras: Induced Protein Degradation as a Therapeutic Strategy," ACS Chem. Biol., Apr. 2017, vol. 12(4), pp. 92-898.
Raedler, L. A., "Farydak (Panobinostat): First HDAC Inhibitor Approved for Patients with Relapsed Multiple Myeloma," Am. Health Drug Benefits, Mar. 2016, vol. 9, pp. 84-87.
Sakamoto, K. M., "Chimeric molecules to target proteins for ubiquitination and degradation," Methods Enzymol., Dec. 2005, vol. 399, pp. 833-847.
Sakamoto, K. M. et al., "Protacs: chimeric molecules that target proteins to the Skp1-Cullin-F box complex for ubiquitination and degradation," Proc Natl Acad Sci USA, Jul. 2001, vol. 98(15), pp. 8554-8559.
Seymour, J. F., et al., "High Overall Response Rate With the Btk Inhibitor BGB-3111 in Patients With Chronic Lymphocytic Leukemia/Small Lymphocytic Lymphoma: an Update On Safety and Activity," Hematological Oncology, 2022, 35: 234- 235.
Sun, Y. et al., "Degradation of Bruton's tyrosine kinase mutants by PROTACs for potential treatment of ibrutinib-resistant non-Hodgkin lymphomas," Leukemia, Mar. 2019, vol. 33, pp. 2105-2110.
Sun, Y. et al., Letter to the Editor, "PROTAC-induced BTK degradation as a novel therapy for mutated Btk C481S induced ibrutinib-resistant B-cell malignancies," Cell Research, Jul. 2018, vol. 28(7), pp. 779-781.
Swatek, K. N. et al., "Ubiquitin modifications," Cell Res., Apr. 2016, vol. 26, No. 4, pp. 399-422.
Tam, C. et al., " The BTK Inhibitor, Bgb-3111, Is Safe, Tolerable, and Highly Active in Patients with Relapsed/ Refractory B-Cell

(56) References Cited

OTHER PUBLICATIONS

Malignancies: Initial Report of a Phase 1 First-in-Human Trial," Blood, 2015, vol. 126 (23), 8 pages.

Tam, C. S. et al., "Phase 1 study of the selective BTK inhibitor zanubrutinib in B-cell malignancies and safety and efficacy evaluation in CLL," The American Society of Hematology, 2019, vol. 134, No. 11, pp. 851-859.

Tam, C.S. et al., "Clinical pharmacology and PK/PD translation of the second-generation Bruton's tyrosine kinase inhibitor, zanubrutinib," Expert Review of Clinical Pharmacology, 2021, vol. 14:11, pp. 1329-1344.

Tam, C.S. et al., "High Major Response Rate, Including Very Good Partial Responses (VGPR), in Patients (pts) with Waldenstrom Macroglobulinemia (WM) Treated with the Highly Specific BTK Inhibitor Bgb-3111: Expansion Phase Results from an Ongoing Phase I Study," Blood, 2016, vol. 128 (22), p. 1216.

Tam, C.S. et al., "Twice Daily Dosing with the Highly Specific BTK Inhibitor, Bgb-3111, Achieves Complete and Continuous BTK Occupancy in Lymph Nodes, and Is Associated with Durable Responses in Patients (pts) with Chronic Lymphocytic Leukemia (CLL)/Small Lymphocytic Lymphoma (SLL)," Blood, 2016; vol. 128 (22), p. 642.

Toure, M. et al., "Small-Molecule PROTACS: New Approaches to Protein Degradation," Angew. Chem. Int. Ed., 2016, 55(6):1966-1973.

Wang, M. L. et al., "Targeting BTK with Ibrutinib in Relapsed or Refractory Mantle- Cell Lymphoma," N. Engl. J. Med., Aug. 8, 2013, vol. 369, pp. 507-516.

Wu, J. et al., "Second-generation inhibitors of Bruton tyrosine kinase," J Hematol Oncol. Sep. 2, 2016, vol. 9(1), p. 80.

Zhou, P. et al., "Harnessing the ubiquitination machinery to target the degradation of specific cellular proteins," Mol. Cell., Sep. 2000, vol. 6(3), pp. 751-756.

Zorba, A. et al., "Delineating the role of cooperativity in the design of potent PROTACs for BTK," PNAS, Jun. 2018, vol. 115(31), pp. E7285-E7292.

\* cited by examiner

TREATMENT OF INDOLENT OR AGGRESSIVE B-CELL LYMPHOMAS USING A COMBINATION COMPRISING BTK INHIBITORS

CROSS-REFERENCE TO RELATED APPLICATIONS

This application is a U.S. National Stage Application under 35 U.S.C. § 371 of International Application No. PCT/US2018/063068, filed Nov. 29, 2018, which claims the benefit of priority to U.S. Provisional Application No. 62/592,111, filed on Nov. 29, 2017, the disclosures of each of which are hereby incorporated by references in their entireties for all purposes.

DESCRIPTION OF THE TEXT FILE SUBMITTED ELECTRONICALLY HEREWITH

The contents of the text file submitted electronically herewith are incorporated herein by reference in their entirety: A computer readable format copy of the Sequence Listing (filename: BEIG_-030_01US_SeqList.txt, date recorded: May 26, 2020; file size 129,310 bytes).

FIELD OF THE INVENTION

Disclosed herein is a method for the prevention, delay of progression or treatment of indolent or aggressive B-cell lymphomas in an individual in need thereof, comprising administering a Btk inhibitor (in particular (S)-7-(1-acryloylpiperidin-4-yl)-2-(4-phenoxyphenyl)-4,5,6,7-tetrahydropyrazolo-[1,5-a]pyrimidine-3-carboxamide or a pharmaceutically acceptable salt thereof) in combination with an anti-PD-1 antibody. The potent and selective BTK inhibitor in combination with the anti-PD-1 antibody have a manageable toxicity profile in patients with indolent and aggressive lymphomas.

BACKGROUND OF THE INVENTION

The lymphatic system is made up of lymph nodes, lymphatic organs, and lymphatic vessels and the lymphatic system carries lymph, a colorless fluid that contains lymphocytes. There are several types of lymphocytes, including: B-lymphocytes, or B cells and T-lymphocytes, or T cells.

Lymphomas are cancers of lymphoid tissue. They comprise a group of heterogeneous cancers, divided into non-Hodgkin's lymphomas (NHL) and Hodgkin's lymphomas (HL). There are two main types of lymphoma: Hodgkin's lymphoma and non-Hodgkin's lymphoma (NHL). About 90% of people in western countries with lymphoma have B-cell non-Hodgkin's lymphoma (https://www.cancer.net/cancer-types/lymphoma-non-hodgkin/subtypes).

Based on how quickly the cancer is growing, NHL can be categorized as aggressive or indolent. Indolent NHL types have a relatively good prognosis but they are not curable in advanced clinical stages. Most of the indolent types are nodular (or follicular) in morphology. Follicular lymphoma (FL) is by far the most common of the indolent NHLs and represents almost 25% of all new cases of NHL. The aggressive type of NHL (e.g. diffuse large B-cell lymphoma (DLBCL)) has a shorter life expectancy.

Bruton's tyrosine kinase (Btk) belongs to the Tec family of cytoplasmic tyrosine kinases, which is the second largest family of non-receptor kinases in humans [Vetrie et al., Nature 361: 226-233, 1993; Bradshaw, Cell Signal. 22: 1175-84, 2010]. It is expressed in all cell lineages of the hematopoietic system, except for T cells and is localized in bone marrow, spleen and lymph node tissue [Smith et al., J. Immunol. 152: 557-565, 1994]. Inactivating mutations in the gene encoding Btk cause X-linked agammaglobulinemia (XLA) in humans and X-linked immunodeficiency (XID) in mice [Conley et al., Annu. Rev. Immunol. 27: 199-227, 2009]. Both diseases are characterized by dramatic defects in B cell development and function, suggesting the essential role of Btk for B cell development and function. In addition, constitutive activation of Btk in B cells results in the accumulation of autoreactive plasma cells [Kersseboom et al., Eur J Immunol. 40:2643-2654, 2010]. Btk is activated by upstream Src-family kinases in BCR signaling pathway. Once activated, Btk in turn phosphorylates phospholipase-Cγ (PLCγ), leading to $Ca^{2+}$ mobilization and activation of NF-κB and MAP kinase pathways. These proximal signaling events promote expression of genes involved in proliferation and survival [Humphries et al., J. Biol. Chem. 279: 37651, 2004]. In addition to its essential regulatory role as downstream of BCR, Btk activity also plays a critical role in FcR signaling. Signaling via FcRγ associated receptors also promotes Btk-dependent proinflammatory cytokine production by cells such as macrophages [Di Paolo et al., Nat. Chem. Biol. 7: 41-50, 2011]. Btk has been an important target due to its proximal location in the BCR and FcR signaling pathways. Preclinical studies show that Btk deficient mice are resistant to developing collagen-induced arthritis. In addition, aberrant activating of Btk plays important role in pathogenesis of B-cell lymphomas indicating that inhibition of Btk is useful in the treatment of hematological malignancies [Davis et al., Nature 463: 88-92, 2010].

WO2014/173289A1 disclosed a series of fused heterocyclic compounds having the following general Formula (I) or a stereoisomer thereof, or a pharmaceutically acceptable salt thereof as Btk inhibitors, which have demonstrated potent inhibitory activity against Bruton's tyrosine kinase.

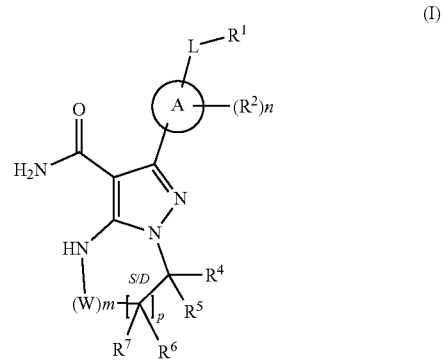

WO2018/033853A2 disclosed a crystalline form of the Btk inhibitor in WO2014/173289A1, particularly, (S)-7-(1-acryloylpiperidin-4-yl)-2-(4-phenoxyphenyl)-4,5,6,7-tetrahydropyrazolo[1,5-a]pyrimidine-3-carboxamide (hereinafter Compound 1) for the treatment of cancers with aberrations in the B-cell receptor (BCR) and FcR signaling pathway in which Btk plays important roles. Compound 1 has demonstrated to have potent and irreversible inhibitory activities against Btk. The contents of the publications WO2014/173289 and WO2018/033853 are hereby incorporated by reference in their entireties for all purposes.

Compound 1

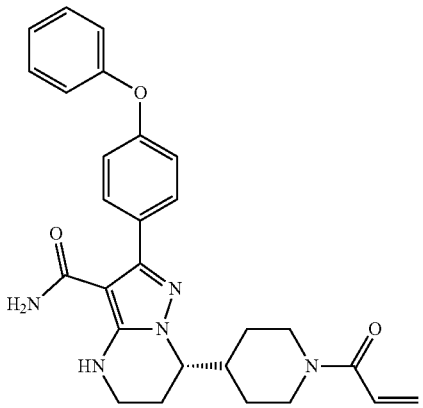

SUMMARY OF THE INVENTION

The inventors of the present application have found that the combination of a Btk inhibitor (in particular, Compound 1) with an anti-PD-1 antibody can be used to treat indolent or aggressive B-cell lymphomas in an individual.

In a first aspect, disclosed herein is a method for the prevention, delay of progression or treatment of indolent or aggressive B-cell lymphomas in an individual in need thereof, comprising administering a therapeutically effective amount of a Btk inhibitor of Formula (I) or a stereoisomer thereof, or a pharmaceutically acceptable salt thereof, in combination with a therapeutically effective amount of an anti-PD-1 antibody.

In a second aspect, disclosed herein is a Btk inhibitor of Formula (I) or a stereoisomer thereof, or a pharmaceutically acceptable salt thereof, for use in the prevention, delay of progression or treatment of indolent or aggressive B-cell lymphomas in combination with an anti-PD-1 antibody. In one embodiment of this aspect, disclosed herein is an anti-PD-1 antibody for use in the prevention, delay of progression or treatment of indolent or aggressive B-cell lymphomas in combination with a Btk inhibitor of Formula (I) or a stereoisomer thereof, or a pharmaceutically acceptable salt thereof.

The methods disclosed herein, as a combination therapies, provide methods of treatment that are significantly more efficacious than either single agent.

In an embodiment of each of the above aspects, the anti-PD-1 antibody is a monoclonal antibody.

In an embodiments of each of the above aspects, the indolent or aggressive B-cell lymphomas is indolent or aggressive Hodgkin's lymphoma. In other embodiment, the indolent or aggressive B-cell lymphomas is the indolent or aggressive non-Hodgkin's lymphoma. In a further embodiment, the indolent or aggressive B-cell lymphomas is indolent or aggressive chronic lymphocytic leukemia (CLL), small lymphocytic lymphoma (SLL), follicular lymphoma (FL), mantle cell lymphoma (MCL), marginal zone lymphoma (MZL), Waldenström's macroglobulinemia (WM), Hairy cell leukemia (HCL), Burkitt's-like leukemia (BL), B cell prolymphocytic leukemia (B-PLL), diffuse large B cell lymphoma (DLBCL), germinal center B-cell diffuse large B-cell lymphoma (GCB-DLBCL), non-germinal center B-cell diffuse large B-cell lymphoma (non-GCB DLBCL), DLBCL with undetermined subtype, primary central nervous system lymphoma (PCNSL), secondary central nervous system lymphoma (SCNSL) of breast or testicular origin, transformed lymphoma, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, lymphomatoid granulomatosis, or a combination thereof. In an embodiment of each of the above aspects, the indolent or aggressive B-cell lymphomas is indolent or aggressive diffuse large B-cell lymphoma (DLBCL). In an embodiment of each of the above aspects, DLBCL is activated B-cell diffuse large B-cell lymphoma (ABC-DLBCL), GCB-DLBCL or Non-GCB DLBCL. In an embodiment of each of the above aspects, the indolent or aggressive B-cell lymphomas is indolent or aggressive chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma or a combination thereof. In an embodiment of each of the above aspects, the indolent or aggressive B-cell lymphomas is indolent or aggressive relapsed or refractory (R/R) B-cell malignancy. In an embodiment of each of the above aspects, the relapsed or refractory B-cell malignancy is diffuse large B-cell lymphoma (DLBCL). In an embodiments of each of the above aspects, the relapsed or refractory DLBCL is activated B-cell diffuse large B-cell lymphoma (ABC-DLBCL), GCB-DLBCL or Non-GCB DLBCL. In an embodiment of each of the above aspects, the relapsed or refractory (R/R) B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In an embodiment of each of the above aspects, the B-cell malignancy is a metastasized B-cell malignancy. In an embodiment of each of the above aspects, the metastasized B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma or a combination thereof.

In an embodiment of each of the above aspects, the BTK inhibitor is (S)-7-(1-acryloylpiperidin-4-yl)-2-(4-phenoxyphenyl)-4,5,6,7-tetra-hydropyrazolo[1,5-a]pyrimidine-3-carboxamide (Compound 1), or a pharmaceutically acceptable salt thereof. In an embodiment of each of the above aspects, the anti-PD-1 antibody is Mab 1 as disclosed herein. In an embodiment of each of the above aspects, the Btk inhibitor and the anti-PD-1 antibody are administered simultaneously, sequentially or intermittently.

DETAILED DESCRIPTION OF THE INVENTION

Figure 1:
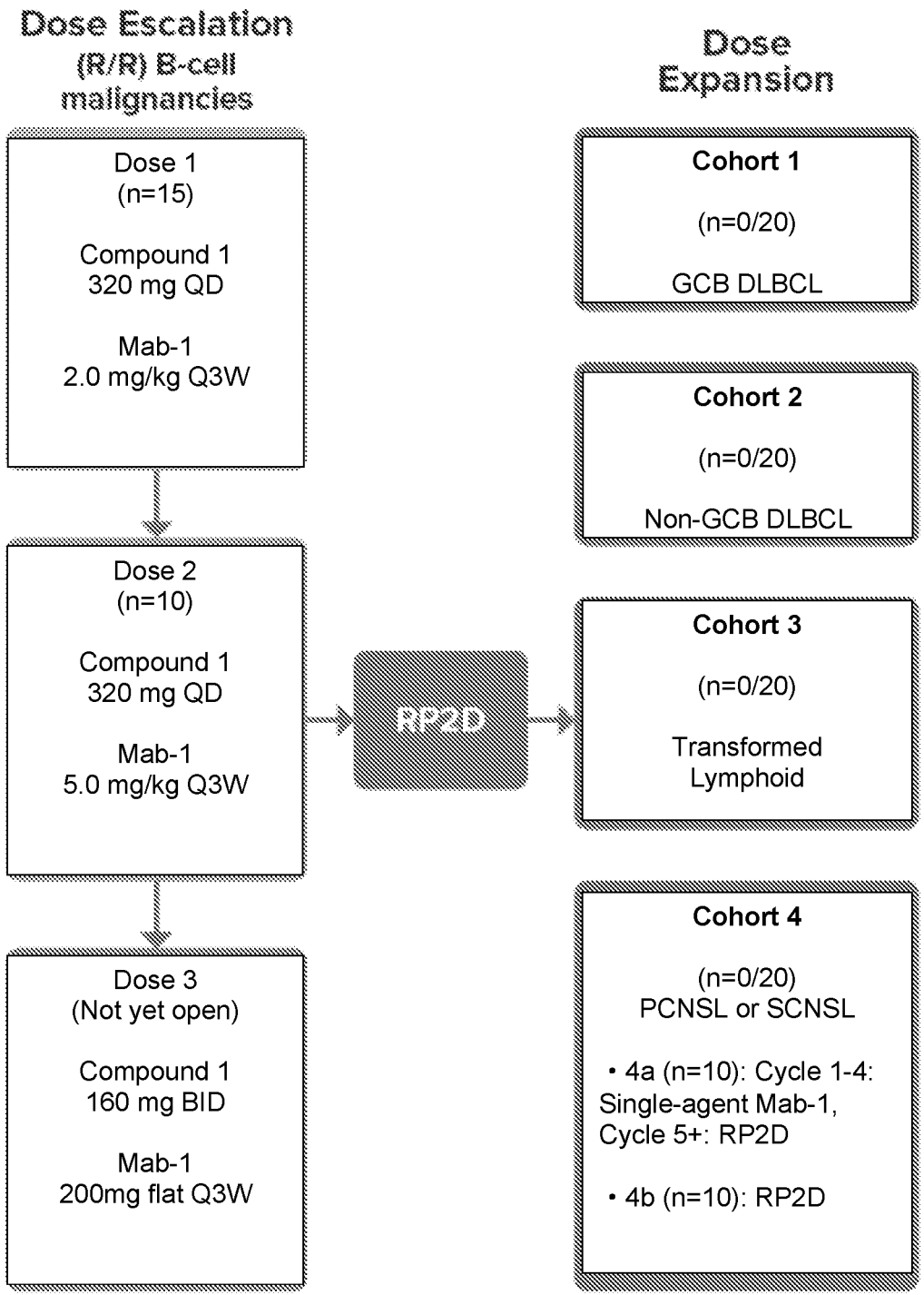
FIG. 1 shows the trial design of the combination of Compound 1 and Mab-1.

Abbreviations (1):

| | |
|---|---|
| ABC-DLBCL | Activated B-cell diffuse large B-cell lymphoma |
| A2AR | Adenosine A2A receptor |
| B-PLL | B cell prolymphocytic leukemia |
| Btk | Bruton's Tyrosine Kinase |
| BTLA | B and T Lymphocyte Attenuator, CD272 |
| CDR | Complementarity Determining Region |
| CLL | chronic lymphocytic leukemia |
| CTLA-4 | Cytotoxic T-Lymphocyte-Associated protein 4, CD152 |
| DLBCL | diffuse large B-cell lymphoma |
| DMEM | Dulbecco minimum essential medium |
| HVEM | Herpesvirus Entry Mediator |
| non-CLL/SLL | non-chronic lymphocytic leukemia/small lymphocytic lymphoma |
| IG | immunoglobulin G |
| i.p. | Intraperitoneal or Intraperitoneally |
| mAb | Monoclonal antibodies |
| PD-1 | Programmed Death 1 protein, Pdcd-1, CD279 |
| p.o. | "by mouth" or "per os" |
| QD | Once daily |
| BID | Twice daily |
| Q4D | Once every four days |
| QW | Once weekly |
| Q2W | Once every two weeks |
| Q3W | Once every three weeks |
| SLL | small lymphocytic lymphoma |
| Vh | Heavy chain variable region |
| Vl | Light chain variable region |
| VISTA | V-domain Ig suppressor of T-cell activation |

Abbreviations (2):

| | |
|---|---|
| ACN | acetonitrile |
| AcOH | Acetic acid |
| D-DBTA | (2S,3S)-Dibenzoyl tartaric acid |
| DCM | Dichloromethane |
| DMF | N,N-dimethylformamide |
| DMF-DMA | N,N-dimethylformamide dimethyl acetal |
| EA | Ethyl Acetate |
| EDCI | 1-Ethyl-3-(3-dimethylaminopropyl)carbodiimide |
| EtOAc | ethyl acetate |
| HOBt | Hydroxybenzotriazole |
| HPLC | High Performance Liquid Chromatography |
| L-DBTA | (2R,3R)-Dibenzoyl tartaric acid |
| MeCN | Acetonitrile |
| MeOH | Methanol |
| MeMgBr | Methyl Magnesium Bromide |
| MsOH | Methanesulfonic Acid |
| MTBE | Methyl tertiary butyl ether |
| NLT | not less than |
| NMR | Nuclear Magnetic Resonance |
| NMT | not more than |
| Pd | Palladium |
| pH | Hydrogen ion concentration |
| RT | Room Temperature |
| TEA | Triethylamine |
| XRPD | X-ray Powder Diffraction |

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

Throughout this specification and the claims which follow, unless the context requires otherwise, the word "comprise", and variations such as "comprises" and "comprising", will be understood to imply the inclusion of an active agent (e.g., a mAb or a Btk inhibitor) or a stated amino acid sequence, but not the exclusion of any other active ingredient or amino acid sequence. When used herein the term "comprising" can be interchangeable with the term "containing" or "including".

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, and indane; and tricyclic ring systems such as 10-15 membered tricyclic ring systems wherein at least one ring is carbocyclic and aromatic, for example, fluorene. For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from: 5- to 7-membered aromatic, monocyclic rings comprising 1, 2, 3 or 4 heteroatoms selected from N, O, and S, with the remaining ring atoms being carbon; 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring. For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

The "heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-difhietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxafhiepanyl, 1,4-oxaazepanyl, 1,4-difhiepanyl, 1,4-fhiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco [3.1.0]hexanyl, 3-azabicyclo [4.1.0]heptanyl and azabicyclo [2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

Substituents are selected from: halogen, —$R^a$, —$OR^a$, =O, =$NR^a$, =N—$OR^a$, —$NR^aR^b$, —$SR^a$, —$SiR^aR^aR^b$, —OC(O)$R^a$, —C(O)$R^a$, —CO$_2R^a$, —CONR$^aR^b$, —OC(O) NR$^aR^b$, —NR$^b$C(O)$R^a$, —$NR^a$—C(O)NR$^bR^b$, —$NR^a$—SO$_2$NR$^b$, —NR$^b$CO$_2R^a$, —NH—C(NH$_2$)=NH, —NR$^a$C (NH$_2$)=NH, —NH—C(NH$_2$)=NR$^a$, —S(O)$R^a$, —SO$_2R^a$, —SO$_2$NR$^aR^b$, —NR$^b$SO$_2$R, —CN and —NO$_2$, —N$_3$, —CH (Ph)$_2$, perfluoro(C$_1$-C$_4$)alkoxy and perfluoro(C$_1$-C$_4$)alkyl, in a number ranging from zero to three, with those groups having zero, one or two substituents being particularly preferred. $R^a$, $R^b$ and $R^c$ each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When $R^a$ and $R^b$ are attached to the same nitrogen atom, they can be combined with the nitrogen atom to form a 5-, 6- or 7-membered ring. Hence, —$NR^aR^b$ includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl". Preferred substituents are selected from: halogen, —$R^a$, —$OR^a$, =O, —$NR^aR^b$, —$SR^a$, —SiR$^aR^aR^b$, —OC(O)$R^a$, —C(O)$R^a$, —CO$_2R^a$, —CONR$^aR^b$, —OC(O)NR$^aR^b$, —NR$^b$C(O)$R^a$, —NR$^b$CO$_2R^a$, —$NR^a$—SO$_2$NR$^bR^b$, —S(O)$R^a$, —SO$_2R^a$, —SO$_2$NR$^aR^b$, —NR$^b$SO$_2$R, —CN and —NO$_2$, perfluoro(C$_1$-C$_4$)alkoxy and perfluoro(C$_1$-C$_4$)alkyl, where $R^a$ and $R^b$ are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

The term "pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethyl-sulfonates, benzoates, salicylates, stearates, alkanoates such as acetate, and salts with HOOC—(CH$_2$)$_n$—COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of R <16> as described herein.

The term "antibody" herein is used in the broadest sense and specifically covers antibodies (including full length monoclonal antibodies) and antibody fragments so long as they recognize antigen, such as, an immune checkpoint (e.g., PD-1). An antibody molecule is usually monospecific, but may also be described as idiospecific, heterospecific, or polyspecific. Antibody molecules bind by means of specific binding sites to specific antigenic determinants or epitopes on antigens.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example, U.S. Pat. No. 4,376,110. The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (Vl/Vh) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located between relatively conserved framework regions (FR). The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). The assignment of amino acids to each domain is, generally, in accordance with the definitions of Sequences of Proteins of Immunological Interest, Kabat, et al., *National Institutes of Health*, Bethesda, Md.; 5<m>ed.; *NIH Publ. No.* 91-3242 (1991); Kabat (1978) *Adv. Prot. Chem.* 32: 1-75; Kabat, et al., (1977) *J. Biol. Chem.* 252:6609-6616; Chothia, et al, (1987) *J Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "complementarity determining region" or "CDR" (i.e., CDR-L1, CDR-L2 and CDR-L3 in the light chain variable domain and CDR-H1, CDR-H2 and CDR-H3 in the heavy chain variable domain). See, Kabat et al. (1991) *Sequences of Proteins of Immunological Interest, 5th Ed.* Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). The term "framework" or "FR" means those variable domain residues other than the hypervariable region residues defined herein as CDR residues.

Unless otherwise indicated, "antibody fragment" or "antigen-binding fragment" means antigen binding fragments of antibodies, i.e. antibody fragments that retain the ability to bind specifically to the antigen bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human PD-1 molecule, if it binds to polypeptides comprising that sequence but does not bind to proteins lacking that sequence.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu", "Hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "disease" refers to any disease, discomfort, illness, symptoms or indications, and can be substituted with the term "disorder" or "condition".

In some embodiments, the B-cell malignancy is chronic lymphocytic leukemia (CLL), small lymphocytic lymphoma (SLL), follicular lymphoma (FL), mantle cell lymphoma (MCL), marginal zone lymphoma (MZL), Waldenström's macroglobulinemia (WM), Hairy cell leukemia (HCL), Burkitt's-like leukemia (BL), B cell prolymphocytic leukemia (B-PLL), diffuse large B cell lymphoma (DLBCL), germinal center B-cell diffuse large B-cell lymphoma (GCB-DLBCL), non-germinal center B-cell diffuse large B-cell lymphoma (non-GCB DLBCL), DLBCL with undetermined subtype, primary central nervous system lymphoma (PCNSL), secondary central nervous system lymphoma (SCNSL) of breast or testicular origin, transformed lymphoma, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, lymphomatoid granulomatosis, or a combination thereof. In some embodiments, the B-cell malignancy is diffuse large B-cell lymphoma (DLBCL). In some embodiments, DLBCL is activated B-cell diffuse large B-cell lymphoma (ABC-DLBCL), GCB-DLBCL or Non-GCB DLBCL. In some embodiments, the B-cell malignancy is chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In some embodiments, the B-cell malignancy is a relapsed or refractory (R/R) B-cell malignancy. In some embodiments, the relapsed or refractory (R/R) B-cell malignancy is diffuse large B-cell lymphoma (DLBCL). In some embodiments, the relapsed or refractory DLBCL is activated B-cell diffuse large B-cell lymphoma (ABC-DLBCL), GCB-DLBCL or Non-GCB DLBCL. In some embodiments, the relapsed or refractory (R/R) B-cell malignancy is chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In some embodiments, the B-cell malignancy is a metastasized B-cell malignancy. In some embodiments, the metastasized B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof.

The term "CDRs" means complementarity determining region(s) in an immunoglobulin variable region, defined using the Kabat numbering system, unless otherwise indicated.

Anti-PD-1 Antibody

PD-1 is an immune checkpoint protein, that limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, *Nature Reviews Cancer*, 12: 252-264, 2012). PD-1 blockade can be accomplished by a variety of mechanisms including antibodies that bind PD-1 or its ligands. Examples of PD-1 and PD-L1 blockers, also named PD-1 and PD-L1 inhibitors, are described in U.S. Pat. Nos. 7,488,802; 7,943,743; 8,008,449; 8,168,757; 8,217,149, and WO03042402, WO2008156712, WO2010089411, WO2010036959, WO2011066342, WO2011159877, WO2011082400, WO2011161699, and WO2015035606, the entire contents of each of which are incorporated herein by reference. In some embodiments the PD-1 inhibitors include an antibody or a fragment antigen binding thereof, which specifically binds to PD-1. In certain other embodiments the PD-1 blockers include anti-PD-1 antibodies and similar binding proteins such as nivolumab (MDX 1106, BMS 936558, ONO-4538, Opdivo®) described in U.S. Pat. No. 8,008,449B2, a fully human IgG4 antibody that binds to and blocks the activation of PD-1 by its ligands PD-L1 and PD-L2; pembrolizumab (lambrolizumab, MK-3475 or SCH 900475, Keytruda®) disclosed in U.S. Pat. No. 8,168,757B2, a humanized monoclonal IgG4 antibody against PD-1; pidilizumab (CT-011), a humanized antibody that binds PD-1; AMP-224, a fusion protein of B7-DC; an antibody Fc portion; BMS-936559 (MDX-1105-01) for PD-L1 (B7-H1) blockade for PD-1 blockade.

In some embodiments, the anti-PD-1 antibody is a monoclonal antibody. In some embodiments, the anti-PD-1 antibody is nivolumab or pidilizumab.

In some embodiments, the anti-PD-1 antibody is a monoclonal antibody or a fragment thereof, disclosed in WO2015/035606 A1 or US2015-0315274, the entire disclosures of which are expressly incorporated herein by reference.

Preferably, the anti-PD-1 monoclonal antibody is an antibody which comprises a heavy chain variable region (Vh) and a light chain variable region (Vl) that contain complement determinant regions (CDRs) listed as follows:

| | |
|---|---|
| a) mu317 | CDR-H1, CDR-H2 and CDR-H3 (SEQ ID NOs: 11, 12, 13, respectively); and CDR-L1, CDR-L2 and CDR-L3 (SEQ ID NOs: 14, 15, 16, respectively); |
| b) mu326 | CDR-H1, CDR-H2 and CDR-H3 (SEQ ID NOs: 17, 18, 19, respectively); and CDR-L1, CDR-L2 and CDR-L3 (SEQ ID NOs: 20, 21, 22, respectively); |
| c) 317-4B6 | CDR-H1, CDR-H2 and CDR-H3 (SEQ ID NOs: 31, 32, 33, respectively); and CDR-L1, CDR-L2 and CDR-L3 (SEQ ID NOs: 34, 35, 36, respectively); |
| d) 326-4A3 | CDR-H1, CDR-H2 and CDR-H3 (SEQ ID NOs: 37, 38, 39, respectively); and CDR-L1, CDR--L2 and CDR-L3 (SEQ ID NOs: 40, 41, 42, respectively); |

| | |
|---|---|
| e) 317-1H | CDR-H1, CDR-H2 and CDR-H3 (SEQ ID NOs: 11, 59, 13, respectively); and CDR-L1, CDR-L2 and CDR-L3 (SEQ ID NOs: 14, 15, 16, respectively); |
| f) 317-4B2 | CDR-HL, CDR-H2 and CDR-H3 (SEQ ID NOs: 11, 60, 13, respectively); and CDR-L1, CDR-L2 and CDR-L3 (SEQ ID NOs: 61, 15, 16, respectively); |
| g) 317-4B5 | CDR-Hl, CDR-H2 and CDR-H3 (SEQ ID NOs: 11, 60, 13, respectively); and CDR-L1, CDR-L2 and CDR-L3 (SEQ ID NOs: 61, 15, 16, respectively); |
| h) 317-4B6 | CDR-H1, CDR-H2 and CDR-H3 (SEQ ID NOs: 11, 32, 13, respectively); and CDR-L1, CDR-L2 and CDR-L3 (SEQ ID NOs: 61, 15, 16, respectively); |
| i) 326-1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| j) 326-3B1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| or k) 326-3G1 | CDR-H1, CDR-H2 and CDR-H3 (SEQ ID NOs: 17, 62, 19, respectively); and CDR-L1, CDR-I 2 and CDR-L3 (SEQ ID NOs: 20, 21, 22, respectively). |

Preferably, the anti-PD-1 monoclonal antibody is an antibody which comprises a heavy chain variable region (Vh) and a light chain variable region (Vl) that contain any combinations of CDRs listed as follows:

| | |
|---|---|
| (a) | CDR-H1 (SEQ ID NO 31), CDR-H2 (SEQ ID NO 12, 32, 59 or 60) and CDR-H3 (SEQ ID NO 33), CDR-L1 (SEQ ID NO 14, 34 or 61), CDR-L2 (SEQ ID NO 35) and CDR-L3 (SEQ ID NO 36); or |
| (b) | CDR-H1 (SEQ ID NO 37), CDR-H2 (SEQ ID NO 18, 38 or 62) and CDR-H3 (SEQ ID NO 39), CDR-L1 (SEQ ID NO 40), CDR-L2 (SEQ ID NO 41) and CDR-L3 (SEQ ID NO 42). |

Preferably, the anti-PD-1 monoclonal antibody is an antibody which comprises a heavy chain variable region (Vh) and a light chain variable region (Vl) comprising:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

In some embodiments, the antibody comprises an IgG4 Fc region having a serine to proline mutation at position 228 (EU numbering system). In some embodiments, this mutation is referred to as the S228P mutation. In some embodiments, the antibody comprises an IgG4 Fc region having a mutation at one or more of positions 233, 234, 235, 265, 309, and 409 (EU numbering system). For example, in some embodiments, the antibody comprises an IgG4 region having a mutation at 228 and at least one other position, wherein the at least one other mutation results in reduced binding to one or more FcγR. In further embodiments, the antibody comprises an IgG4 region having a mutation at position 228 and at least two, at least 3, at least 4, at least 5, or at least 6 additional positions, wherein one or more of the additional mutations results in reduced binding to one or more FcγR. In some embodiments, the antibody comprises an IgG4 region having mutations at positions 234 and 235. In some embodiments, the antibody comprises an IgG4 region having mutations at positions 233, 235, and 235. In some embodiments, the antibody comprises an IgG4 region having mutations at positions 234, 235, and 265. In some embodiments, the antibody comprises an IgG4 region having mutations at positions 233, 234, 235, and 265. In some embodiments, the antibody comprises an IgG4 region having mutations at positions 234, 235, 265, and 409. In some embodiments, the antibody comprises an IgG4 region having mutations at positions 233, 234, 235, 265, and 409. In some embodiments, the antibody comprises an IgG4 region having mutations at positions 234, 235, 265, 309, and 409. In some embodiments, the antibody comprises an IgG4 region having mutations at positions 233, 234, 235, 265, 309, and 409. The mutation at position 234 may be a phenylalanine to valine substitution or a phenylalanine to alanine substitution. The mutation at position 235 may be a leucine to alanine substitution. The mutation at position 233 may be a glutamic acid to proline substitution. The mutation at position 265 may be a aspartic acid to valine substitution or an aspartic acid to threonine substitution. The mutation at position 309 may be a leucine to valine substitution. The mutation at position 409 may be an arginine to a lysine, threonine, or methionine substitution.

Preferably, the anti-PD-1 monoclonal antibody is an antibody which comprises a IgG4 heavy chain effector or constant domain comprising any of SEQ ID NOs: 83-88 or 91-106.

Preferably, the anti-PD-1 monoclonal antibody is an antibody which contains a F(ab) or F(ab)2 comprising a domain said above, including a heavy chain variable region (Vh), a light chain variable region (Vl) and a IgG4 heavy chain effector or constant domain.

Preferably, the anti-PD-1 monoclonal antibody is an antibody which comprise a heavy chain variable region (Vh) and a light chain variable region (Vl), and a IgG4 heavy chain effector or constant domain comprising SEQ ID NOs: 87 or 88, wherein the heavy chain variable region (Vh) and the light chain variable region (Vl) comprise:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

In some embodiments, the anti-PD-1 antibody is an antibody which comprises a heavy chain CDR-H1, CDR-H2, and CDR-H3 according to SEQ ID NOs: 11, 32, and 13, respectively; and a light chain CDR-L1, CDR-L2, and CDR-L3 according to SEQ ID NOs: 61, 15, and 16, respectively. Preferably, the anti-PD-1 monoclonal antibody is an antibody which comprises a heavy chain variable region (Vh) and a light chain variable region (Vl) (comprising SEQ ID No 24 and SEQ ID No 26, respectively) and a IgG4 heavy chain effector or constant domain (comprising SEQ ID NO 88), hereinafter Mab 1, which specifically binds to PD-1, especially PD-1 residues including K45 and I93; or, I93, L95 and P97, and inhibits PD-1-mediated cellular signaling and activities in immune cells, antibodies binding to a set of amino acid residues required for its ligand binding.

The anti-PD1 monoclonal antibodies and antibody fragments thereof may be prepared in accordance with the disclosure of WO2015/035606A1 or US 2015-0315274, the entire disclosures of which are expressly incorporated herein by reference. In a preferred embodiment, the anti-PD1 monoclonal antibodies is Mab 1, which is administered at a dosage of about 2 mg/kg Q3W to about 200 mg/kg Q3W, more preferably, is administered at a dosage of about 2 mg/kg Q3W, 5 mg/kg Q3W or 200 mg flat Q3W.

Btk Inhibitors

"Btk inhibitor" means a compound of Formula (I), or a stereoisomer thereof, or a pharmaceutically acceptable salt thereof.

The Btk inhibitor, as disclosed herein, is a compound of Formula (I),

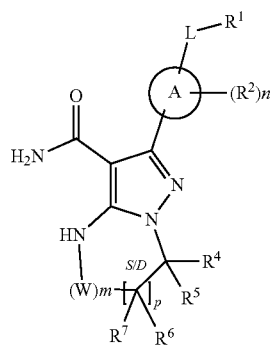

or a stereoisomer thereof, or a pharmaceutically acceptable salt thereof, wherein:

A is a 5- or 6-membered aromatic ring comprising 0-3 heteroatoms of N, S or O; each W is independently —(CH$_2$)— or —C(O)—;

L is a bond, CH$_2$, NR$^{12}$, O, or S;

S/D is a single or double bond, and when a double bond, R$^5$ and R$^7$ are absent;

m is 0, or an integer of 1-4;

n is 0, or an integer of 1-4, wherein when n is more than 1, each R$^2$ may be different;

p is 0, or an integer of 1-2, wherein when p is 0, m is non-zero, and when p is more than 1, each R$^6$ and each R$^7$ may be different;

R$^1$, R$^4$, R$^5$, R$^6$, and R$^7$ are each independently H, halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$, wherein (R$^4$ and R$^5$), or (R$^4$ and R$^6$), or (R$^6$ and R$^7$), or (R$^6$ and R$^6$ when p is 2), together with the atoms to which they are attached, can form a ring selected from cycloalkyl, saturated or unsaturated heterocycle, aryl, and heteroaryl rings optionally substituted with at least one substituent R$^{16}$;

R$^2$ is halogen, alkyl, —S-alkyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$;

R$^{12}$ is H or lower alkyl;

R$^{13}$, R$^{14}$ and R$^{15}$ are each independently H, heteroalkyl, alkyl, alkenyl, alkynyl, cycloalkyl, saturated or unsaturated heterocyclyl, aryl, or heteroaryl; wherein (R$^{13}$ and R$^{14}$), and/or (R$^{14}$ and R$^{15}$) together with the atom(s) to which they are attached, each can form a ring selected from cycloalkyl, saturated or unsaturated heterocycle, aryl, and heteroaryl rings optionally substituted with at least one substituent R$^{16}$;

R$^{16}$ is halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, oxo, —CN, —OR$^a$, —NR$^a$R$^b$, —COR$^a$, —CO$_2$R$^a$, —CONR$^a$R$^b$, —C(=NR$^a$)NR$^b$R$^c$, —NR$^a$COR$^b$, —NR$^a$CONR$^a$R$^b$, —NR$^a$CO$_2$R$^b$, —SO$_2$R$^a$, —SO$_2$aryl, —NR$^a$SO$_2$NR$^b$R$^c$, or —NR$^a$SO$_2$R$^b$, wherein R$^a$, R$^b$, and R$^c$ are independently hydrogen, halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, wherein (R$^a$ and R$^b$), and/or (R$^b$ and R$^c$) together with the atoms to which they are attached, can form a ring selected from cycloalkyl, saturated or unsaturated heterocycle, aryl, and heteroaryl rings.

In some embodiments, the compound of Formula (I) is optically pure.

In some embodiments, S/D is a double bond and R$^5$ and R$^7$ are absent; p is 1 and m is 0, 1 or 2; A is phenyl; and R$^4$ and R$^6$, together with the atoms to which they are attached, form a ring of formula

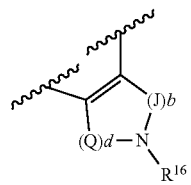

wherein Q is —CH$_2$—; J is —CH$_2$—; and d and b are each independently 0, or an integer of 1-4

S/D is a single bond; p is 1 and m is 0, 1 or 2; A is phenyl; or

S/D is a single bond; p is 0 and R$^6$ and R$^7$ are absent; A is phenyl.

In some embodiments, A is phenyl.
In some embodiments, W is —(CH$_2$)—.
In some embodiments, L is O.
In some embodiments, S/D is a single bond.
In some embodiments, m is 1.
In some embodiments, n is 0. In some embodiments, R$^2$ is absent.
In some embodiments, p is 1.
In some embodiments, R$^1$ is phenyl.
In some embodiments, R$^5$ is H. In some embodiments, R$^6$ and R$^7$ are H.

In some embodiments, A is phenyl; W is —(CH$_2$)—; L is O; S/D is a single bond; m is 1; n is 0; p is 1; R$^1$ is phenyl; R$^2$ is absent; R$^5$ is H; and R$^6$ and R$^7$ are H; yielding the combination structure:

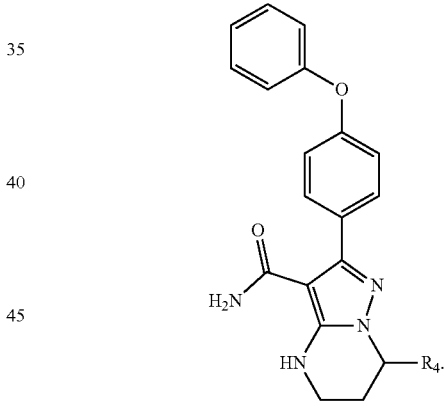

In some embodiments, R$^4$ is N-containing C$_1$-C$_8$ alkyl, N-containing C$_3$-C$_8$ cycloalkyl and phenyl, each optionally substituted.

In some embodiments, R$^4$ is methylamino, aniline group, azetidinyl, pyrrolidinyl, piperidinyl, azacycloheptenyl, each N-substituted with a moiety selected from benzyl, acyl, acryloyl, substituted-acryloyl, propiolyl, and substituted-propiolyl.

In some embodiments, R$^4$ is selected from structures,

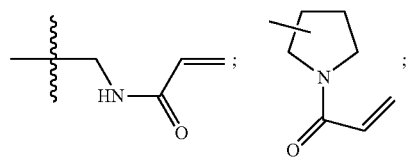

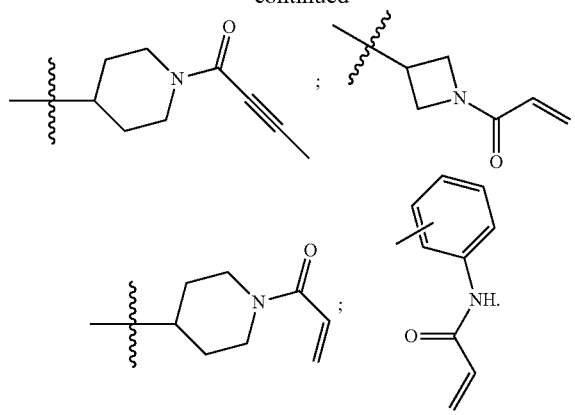

In some embodiments, $R^4$ is

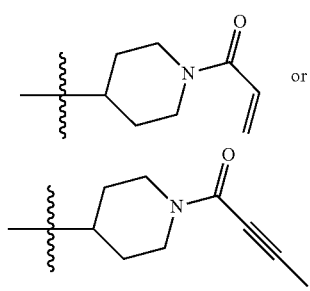

In some embodiments, $R^4$ is 1-acryloylpiperidin-4-yl (i.e., Compound 27 in WO 2014/173289 A1).

In some embodiments, the Btk inhibitor of Formula (I) has the structure of Formula (I-A),

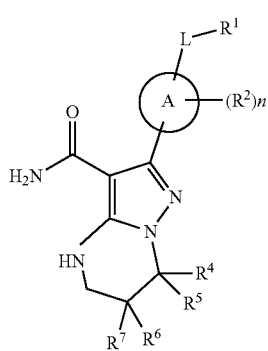

(I-A)

or a stereoisomer thereof, or a pharmaceutically acceptable salt thereof,
wherein:
A is phenyl;
L is a bond, $CH_2$, $NR^{12}$, O, or S;
n is 0, 1, or 2, wherein when n is more than 1, each $R^2$ may be different;
$R^1$ is phenyl, optionally substituted with at least one substituent $R^{16}$;
$R^4$ is N-containing $C_1$-$C_8$ alkyl, N-containing $C_3$-$C_8$ cycloalkyl and phenyl, each optionally substituted with at least one substituent $R^{16a}$;
$R^5$, $R^6$, and $R^7$ are each independently H, halogen, heteroalkyl, alkyl, alkenyl, alkynyl, —CN, —$NR^{13}R^{14}$, or —$OR^{13}$, wherein the alkyl (including alkyl portion of heteroalkyl), alkenyl, and alkynyl, are optionally substituted with at least one substituent $R^{16}$;
$R^2$ is halogen, alkyl, —S-alkyl, —CN, —$NR^{13}R^{14}$, or —$OR^{13}$;
$R^{12}$ is H or $C_1$-$C_3$ alkyl;
$R^{13}$ and $R^{14}$ are each independently H, $C_1$-$C_3$ alkyl, $C_2$-$C_3$ alkenyl, or $C_2$-$C_3$ alkynyl;
$R^{16a}$ is halogen, alkyl, alkenyl, alkynyl, —CN, —$OR^a$, —$NR^aR^b$, —$COR^a$, —$CO_2R^a$, —$CONR^aR^b$, —$NR^aCOR^b$, —$NR^aCONR^aR^b$, —$NR^aCO_2R^b$, wherein $R^a$ and $R^b$ are independently hydrogen, halogen, $C_1$-$C_3$ alkyl, $C_2$-$C_3$ alkenyl, $C_2$-$C_3$ alkynyl; and
$R^{16}$ is halogen, alkyl, alkenyl, alkynyl, —CN, —$OR^a$, or —$NR^aR^b$, wherein $R^a$ and $R^b$ are independently hydrogen, halogen, $C_1$-$C_3$ alkyl, $C_2$-$C_3$ alkenyl, $C_2$-$C_3$ alkynyl.

In some embodiments of the Btk inhibitor of Formula (I-A) or a stereoisomer thereof, or a pharmaceutically acceptable salt thereof,
A is phenyl;
L is O;
n is 0, 1, or 2, wherein when n is more than 1, each $R^2$ may be different;
$R^1$ is phenyl, optionally substituted with at least one substituent $R^{16}$;
$R^4$ is $C_3$-$C_8$ saturated heterocycle containing one N atom as a ring member, optionally substituted with at least one substituent $R^{16a}$;
$R^5$, $R^6$, and $R^7$ are each independently H, halogen, heteroalkyl, alkyl, alkenyl, alkynyl, —CN, —$NR^{13}R^{14}$, or —$OR^{13}$, wherein the alkyl (including alkyl portion of heteroalkyl), alkenyl, and alkynyl, are optionally substituted with at least one substituent $R^{16}$;
$R^2$ is halogen, alkyl, —S-alkyl, —CN, —$NR^{13}R^{14}$, or —$OR^{13}$;
$R^{12}$ is H or $C_1$-$C_3$ alkyl;
$R^{13}$ and $R^{14}$ are each independently H, $C_1$-$C_3$ alkyl, $C_2$-$C_3$ alkenyl, or $C_2$-$C_3$ alkynyl;
$R^{16a}$ is —$C(O)CH=CH_2$, —$C(O)C≡CCH_3$, —$NHC(O)CH=CH_2$, or —$NHC(O)C≡CCH_3$; and
$R^{16}$ is halogen, alkyl, alkenyl, alkynyl, —CN, —$OR^a$, or —$NR^aR^b$, wherein $R^a$ and $R^b$ are independently hydrogen, halogen, $C_1$-$C_3$ alkyl, $C_2$-$C_3$ alkenyl, $C_2$-$C_3$ alkynyl.

As disclosed in each of the above embodiments, the Btk inhibitor is a compound of Formula (II)—i.e., Compound 1.

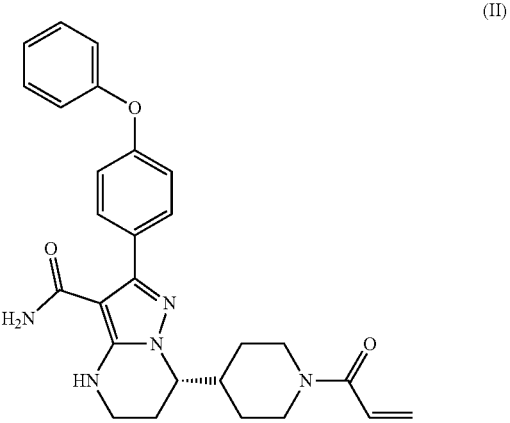 [SMILES: C=CC(=O)N1CCC([C@@H]2CCNc3c(C(N)=O)c(-c4ccc(Oc5ccccc5)cc4)nn32)CC1]

(II)

or a pharmaceutically acceptable salt thereof.

The Btk inhibitor disclosed herein, such as the compound of Formula (II), may be synthesized by synthetic routes disclosed in WO 2014/173289 A1 and unpublished PCT application WO 2018/033853, the entire disclosure of which is expressly incorporated herein by reference. The Btk inhibitor, i.e., Compound 1, disclosed herein, may be prepared in accordance with the procedures in WO 2018/033853, the entire disclosure of which is expressly incorporated herein by reference.

Combination Therapy

The combination therapy may be administered as a simultaneous, or separate or sequential regimen. When administered sequentially, the combination may be administered in two or more administrations. The combined administration includes co-administration, using separate formulation, and consecutive administration in either order, wherein preferably there is a time period while both (or all) active agents simultaneously exert their biological activities.

In some embodiments, the combination therapies provided herein provide a synergistic and/or statistically improved effect relative to either therapy when used as a single agent. For example, the combination therapies disclosed herein result in significant improvement in patient outcome even in indolent and aggressive B-cell malignancies. For example, the combination therapies, in some embodiments, prolong patient survival and progression-free survival while having a manageable toxicity profile in patients suffering from B-cell malignancies, including indolent and aggressive lymphomas.

Suitable dosages for any of the above co-administered agents are those presently used and may be lowered due to the combined action (synergy) of the Btk inhibitor and the targeted therapy agent or the immune checkpoint inhibitor, such as to increase the therapeutic index or mitigate toxicity or other side-effects or consequences.

In a particular embodiment of anti-cancer therapy, the Btk inhibitor and the anti-PD-1 antibody may be further combined with surgical therapy and radiotherapy.

In an embodiment of each of the above aspects, the amounts of the Btk inhibitor the anti-PD-1 antibody disclosed herein and the relative timings of administration be determined by the individual needs of the patient to be treated, administration route, severity of disease or illness, dosing schedule, as well as evaluation and judgment of the designated doctor.

The Btk inhibitor and the anti-PD-1 antibody disclosed herein may be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

In one embodiment of each of the above aspects, the Btk inhibitor the anti-PD-1 antibody disclosed herein may be administered in different route. In a preferred embodiment, the Btk inhibitor is administered orally, and the anti-PD-1 antibody is administered parenterally such as subcutaneously, intracutaneously, intravenously or intraperitoneally. In a preferred embodiment, the BTK inhibitor is administered once a day (once daily, QD), two times per day (twice daily, BID), three times per day (Q3D), four times per day (Q4D), or five times per day (Q5D), and is administered at a dosage of about 80 mg/day to about 640 mg/day. In a preferred embodiment, the BTK inhibitor is administered at a dose of 320 mg QD or 160 mg BID. In a preferred embodiment, the anti-PD1 monoclonal antibodies is Mab 1, which is administered at a dosage of about 2 mg/kg Q3W to about 200 mg/kg once every three weeks (Q3W), more preferably, is administered at a dosage of about 2 mg/kg Q3W, 5 mg/kg Q3W or 200 mg flat Q3W. In a more preferred embodiment, the anti-PD-1 antibody is administered at a dose of 200 mg flat dose every 21 days. In one embodiment, the anti-PD-1 antibody is administered intravenously. In one embodiment, the BTK inhibitor is administered at least 30 minutes before the anti-PD-1 antibody if administered on the same day. Specifically, the BTK inhibitor is administered per day and the anti-PD-1 antibody every three weeks, and the BTK inhibitor is administered at least 30 minutes (sometimes 1 hour or 2 hours) before the anti-PD-1 antibody if administered on the same day.

EXAMPLE

The present invention is further exemplified, but not limited to, by the following examples that illustrate the invention.

Example 1

Preparation of (S)-7-(1-acryloylpiperidin-4-yl)-2-(4-phenoxyphenyl)-4,5,6,7-tetrahydropyrazolo[1,5-a]pyrimidine-3-carboxamide (Compound 1) and Crystalline Form A Thereof Step 1: Synthesis of BG-2

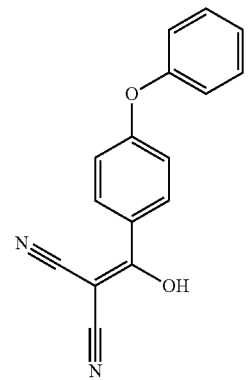

BG-2

Under nitrogen atmosphere, to a solution of EA (5 v), HOBT (1.2 eq.), EDCI (1.2 eq.), 4-phenoxybenzoic acid (BG-1, 80 Kg, 1.0 eq.) and malononitrile (1.2 eq.) was added TEA (2.4 eq.) at 10° C. The mixture was then stirred at RT until the reaction was completed. The mixture was then centrifuged and the cake was washed with EA. The filtrate was washed with aqueous $NaHCO_3$ twice and $NH_4Cl$. The organic phase was washed with 1.5 N $H_2SO_4$ twice and stirred. Concentrated, precipitated from methanol and purified water. The solid was collected by centrifugation and dried under vacuum. This gave 79.9 Kg of BG-2. $^1$H NMR (DMSO-$d_6$) δ 7.62 (d, J=8.6 Hz, 2H), 7.46-7.38 (m, 2H), 7.18 (t, J=7.4 Hz, 1H), 7.06 (d, J=8.0 Hz, 2H), 6.94 (d, J=8.6 Hz, 2H).

Step 2: Synthesis of BG-3

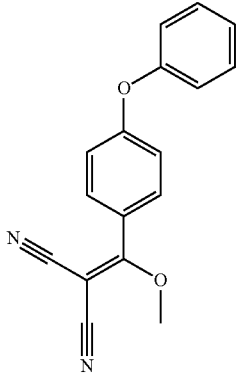

BG-3

Under nitrogen atmosphere, a solution of BG-2 (79.9 kg, 1.0 eq.) in MeCN (5.0 v) was added into trimethoxymethane (12.0 v) at 85° C. The resultant mixture was stirred until the reaction was completed. Sampled for HPLC analysis. Concentrated under vacuum. The residue was precipitated from i-PrOH and hexane. The mixture was centrifuged, and the cake was washed with hexane and dried under vacuum. This gave 71.7 Kg of product. $^1$H NMR (400 MHz, DMSO-d$_6$) δ 7.70 (d, J=8.4 Hz, 2H), 7.52-7.45 (m, 2H), 7.28 (t, J=7.6 Hz, 1H), 7.22-7.06 (m, 4H), 3.93 (s, 3H).

Step 3: Synthesis of BG-4

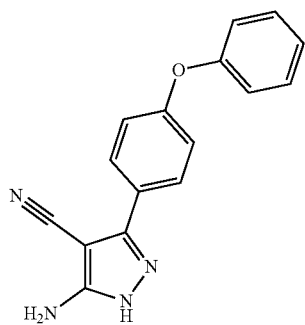

BG-4

Under nitrogen atmosphere, to a solution of BG-3 (71.6 kg, 1.0 eq.) in ethanol (2.5 v) hydrazinium hydroxide (1.0 eq) in ethanol (0.6 v) was charged dropwise to the reactor below 15° C. The solution was heated to RT and stirred until the reaction was completed. Water (4.0 v) was added to the reactor. The solution was then cooled to 5° C., centrifuged and the cake was washed with water (1.0 v). The cake was dried under vacuum. This gave 66.9 Kg of product. $^1$H NMR (DMSO-d$_6$) δ 12.11 (br s, 1H), 7.80 (d, J=8.8 Hz, 2H), 7.46-7.39 (m, 2H), 7.18 (t, J=7.6 Hz, 1H), 7.12-7.04 (m, 4H), 6.43 (br s, 2H).

Steps 4 to 6: Synthesis of BG-8

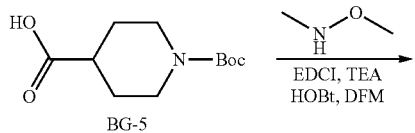

BG-5

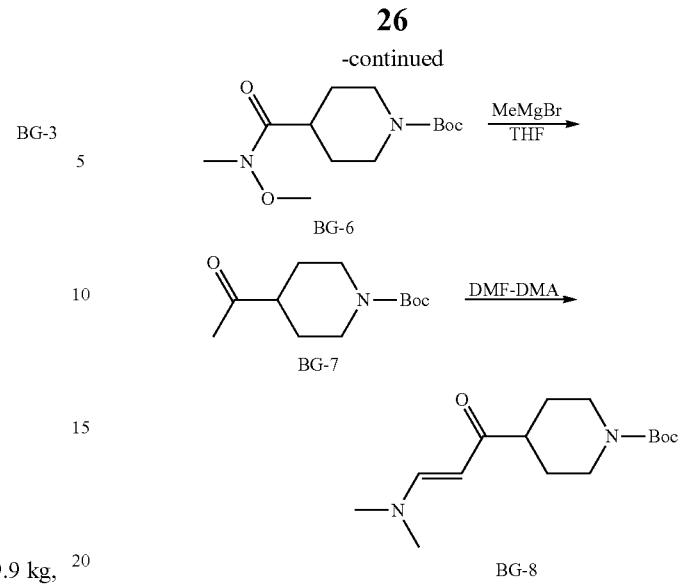

BG-6

BG-7

BG-8

To a mixture of DCM (8.0 v), BG-5 (80.0 Kg, 1.0 eq.), N,O-dimethylhydroxylamine hydrochloride (1.2 eq.), HOBt (1.2 eq.) and EDCI (1.2 eq.), TEA (2.6 eq.) was charged dropwise below 15° C. the mixture was stirred at RT until the reaction was completed, centrifuged and the cake was washed with DCM (1.0 v) twice. The filtrate was washed with 20% aqueous NH$_4$Cl (3×4.0 v). The filtrate was concentrated under vacuum to give the crude product BG-6, which was used in the next step without further purification. The residue was dissolved in toluene (5.0 v) and THF (1.0 v), cooled to 10° C., charged dropwise MeMgBr (1.4 eq.) at 10° C. and then stirred at RT until the reaction was completed. The solution was cooled below 10° C. Saturated aqueous NH$_4$Cl was charged dropwise below 10° C. The mixture was centrifuged, separated, filtrated, and the organic phase was washed with aqueous NaCl twice. The organic phase was concentrated to give the crude product, which was used in the next step without further purification. The residue in DMF (2.5 v) and DMF-DMA (2.5 v) was stirred at 110° C. until the reaction was completed. The reaction mixture was cooled, concentrated and then DCM was added. The final mixture was washed with saturated aqueous NH$_4$Cl. The organic layer was concentrated and precipitated by charging hexane. The mixture was centrifuged and the cake was collected. The cake was dried under vacuum. This gave 82.2 Kg of the desired product. $^1$H NMR (DMSO-d$_6$) δ 7.49 (d, J=12.6 Hz, 1H), 5.01 (d, J=12.6 Hz, 1H), 3.99-3.82 (m, 2H), 3.14-2.94 (m, 2H), 2.89-2.61 (m, 6H), 2.49-2.37 (m, 1H), 1.66-1.56 (m, 2H), 1.39 (s, 9H), 1.39-1.20 (m, 2H).

Step 7: Synthesis of BG-9

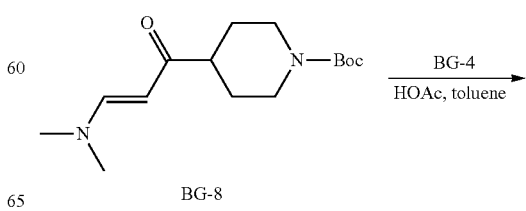

BG-8

-continued

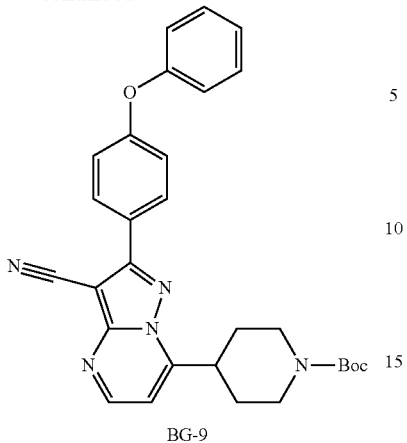

BG-9

Under nitrogen atmosphere, a mixture of toluene (8.0 v), AcOH (0.5 v), BG-8 (1.2 eq.) and BG-4 (66.9 Kg 1.0 eq.) was heated to 95° C. and stirred until the reaction was completed. The mixture was cooled, concentrated and precipitated from methanol. The mixture was centrifuged and the cake was washed with methanol. The cake was dried under vacuum. This gave 107.8 Kg of product. $^1$H NMR (DMSO-d$_6$) δ 8.78 (d, J=4.6 Hz, 1H), 8.15-8.07 (m, 2H), 7.51-7.41 (m, 2H), 7.34 (d, J=4.6 Hz, 1H), 7.27-7.19 (m, 3H), 7.17-7.10 (m, 2H), 4.24-4.02 (m, 2H), 3.81-3.69 (m, 1H), 3.12-3.82 (m, 2H), 2.15-2.04 (m, 2H), 1.76-1.60 (m, 2H), 1.43 (s, 9H).

Step 8: Synthesis of BG-10

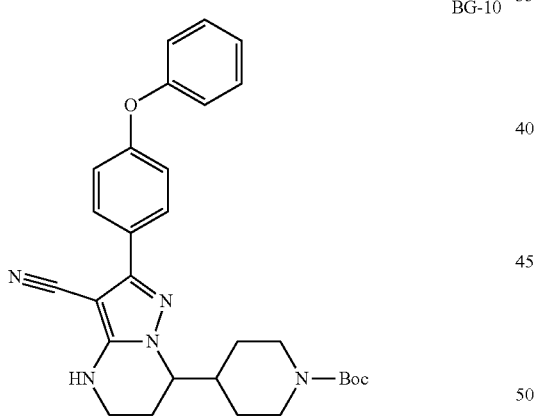

BG-10

To a mixture of THF (10.0 v), BG-9 (13.0 Kg, 1.0 eq.) and D-DBTA (1.0 eq) under N$_2$ was charged Pd/C (10% w/w), hydrogen gas was introduced into the reactor and the hydrogen pressure was maintained to 1.8 MPa. The reactor was heated to 40° C. slowly and stirred until the reaction was completed. The mixture was then cooled, filtered, and the cake was washed with THF. The filtrate was collected, and concentrated under vacuum. DCM was added. The residue was washed with aq. NaHCO$_3$, concentrated and precipitated from MTBE and hexane, then centrifuged. The cake was collected and dried under vacuum to give the desired compound (yield: 94.8% and purity: 98.5%). $^1$H-NMR (DMSO-d$_6$) δ 7.82-7.76 (m, 2H), 7.56-7.51 (m, 1H), 7.45-7.37 (m, 1H), 7.21-7.14 (m, 1H), 7.12-7.03 (m, 4H), 4.09-3.91 (m, 3H), 3.30-3.22 (m, 2H), 2.82-2.55 (m, 2H), 2.18-1.99 (m, 2H), 1.98-1.86 (m, 1H), 1.69-1.58 (m, 1H), 1.56-1.45 (m, 1H), 1.38 (s, 9H), 1.32-1.13 (m, 2H).

Step 9: Synthesis of BG-11

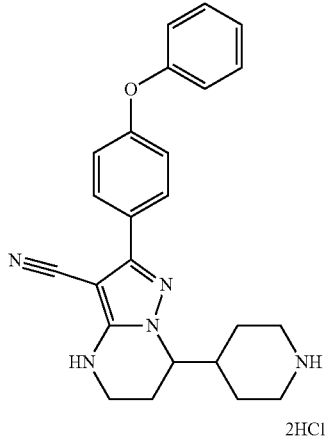

BG-11

To a solution of BG-10 (100.0 Kg 1.0 eq.) in DCM (6.0 v) was added dropwise HCl in EtOH (20.9% w/w, 2.0 v) under nitrogen atmosphere. The mixture was stirred until the reaction was completed. MTBE (4.0 v) was added to the solution, cooled. The cakes was collected by centrifugation and washed with hexane (2.0 V), then the cake was slurried in hexane (5 v), and centrifuged again. The cake was washed with hexane (2.0 V) and dried under vacuum. This gave 85.2 Kg product. $^1$H-NMR (DMSO-d$_6$) δ 9.25-8.85 (m, 2H), 7.84-7.70 (m, 2H), 7.47-7.37 (m, 2H), 7.18 (t, J=7.4 Hz, 1H), 7.12-7.03 (m, 4H), 5.73 (br s, 2H), 4.12-4.03 (m, 1H), 3.25-3.19 (m, 4H), 2.90-2.73 (m, 2H), 2.28-2.12 (m, 1H), 2.10-2.00 (m, 1H), 1.99-1.86 (m, 1H), 1.84-1.52 (m, 4H).

Step 10: Synthesis of BG-11A

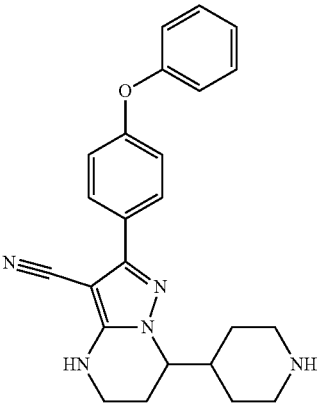

BG-11A

A mixture of BG-11 (85.0 Kg, 1.0 eq) in water (6.0 v) and NaOH (3.0 eq) was stirred until the reaction was completed at RT. The cake was collected and slurried in MTBE (6.0 v). The mixture was then centrifuged to collect the cake. The cake was dried under vacuum. This gave 71.3 Kg product. $^1$H-NMR (DMSO-d$_6$) δ 7.82-7.74 (m, 2H), 7.54-7.49 (m, 1H), 7.45-7.38 (m, 2H), 7.21-7.14 (m, 1H), 7.12-7.04 (m, 4H), 4.03-3.95 (m, 1H), 3.29-3.21 (m, 2H), 3.00-2.87 (m, 2H), 2.46-2.31 (m, 2H), 2.11-1.83 (m, 3H), 1.58-1.12 (m, 4H).

Step 11: Synthesis of BG-11B

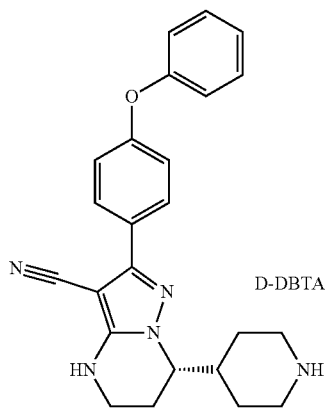

BG-11B

D-DBTA

A mixture of ethanol/water/acetic acid (7:3:1, 46 v) and BG-11A (30 kg, 1.0 eq.) in a reactor was heated to 70±5° C. under nitrogen atmosphere, then a solution of D-DBTA (1.20 eq.) in ethanol/water/acetic acid (7:3:1, 4 v) was added dropwise with the temperature not less than 65° C. The resulting solution was stirred for 16 hrs at 60-65° C., then cooled to RT. The solid was collected by centrifugation and washed with ethanol (2.0 v). The cake was slurried in the mixed solvent of ethanol/water/AcOH (7:3:1, 20 v) for 16 hrs at 55° C. and cooled to RT. The solid was collected by centrifugation, washed with ethanol (2.0 v). The cake was dried under vacuum (Yield: 37.9%). $^1$H-NMR (DMSO-$d_6$) δ 8.76 (br s, 2H), 7.99-7.89 (m, 4H), 7.83-7.75 (m, 2H), 7.66-7.57 (m, 3H), 7.52-7.45 (m, 4H), 7.45-7.39 (m, 2H), 7.21-7.14 (m, 1H), 7.13-7.03 (m, 4H), 5.64 (s, 2H), 4.08-4.00 (m, 1H), 3.29-3.19 (m, 4H), 2.85-2.72 (m, 2H), 2.21-1.40 (m, 7H).

Step 12: Synthesis of BG-11C

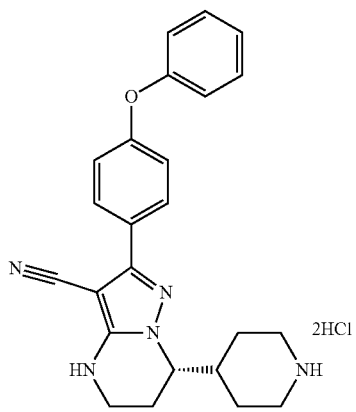

BG-11C

2HCl

To a mixture of dichloromethane (15.0 v) and 20.0% aqueous KOH (3.0 v) was added batchwise BG-11B (48.0 kg, 1.0 eq.) under nitrogen atmosphere at RT. After the reaction was completed, the organic layer was collected and the water layer was extracted with dichloromethane (5.0 v). The organic layers were combined. Con. HCl (0.36 v) was added to the above organic layers at RT. The resulting mixture was stirred until the reaction was completed. The solid was collected by centrifugation and washed with dichloromethane (1.0 v). The collected solid was slurried with MTBE (6.0 v). The solid was collected by centrifugation and washed with MTBE (1.0 v), then was dried under vacuum. This gave 31.5 Kg product (Yield: 100%).

Step 12: Synthesis of BG-11D (Alternative Intermediate)

ACN (5.0 v), soft water (10.0 v), KOH (5.0 eq) was charged to a reactor and stirred for at least 15 min. BG-11B (1.0 eq) was charge to the reactor in portion-wise. The mixture was stirred until the reaction was completed. The cake was collected by centrifugation, slurried in ACN (1.0 v) and soft water (5.0 v), and dried under vacuum to give the product.

Step 13: Synthesis of BG-12

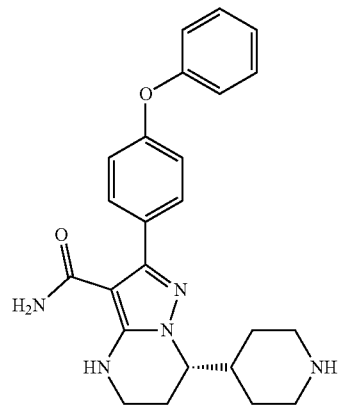

BG-12

A solution of BG-11C (15.0 Kg 1.0 eq.) in MsOH (2.5 v) was stirred at 85° C. under nitrogen atmosphere until the reaction was completed. After cooling to 5° C. purified water (4.0 v) was added dropwise to the system and kept the temperature not more than 35° C. (temperature increased obviously). The resulting solution was stirred for 16 hrs at 30° C., and then washed with DCM (2×3.0 v). The aqueous phase was collected. DCM (6.0 v) was added to the aqueous phase, the mixture was cooled to 5° C. The pH value was adjusted to 11~12 with 20% aqueous NaOH (temperature increased obviously) with stirring with the temperature not more than 30° C. The organic phase was separated and collected. The aqueous was extracted with DCM (3.0 v). The organic layers were combined and concentrated. MTBE (4.0 v) was added to the residue. The mixture was then concentrated and precipitated from n-heptane. The solid was collected by centrifugation and dried in a vacuum oven. This gave 12.55 Kg product (Yield: 94.9%). $^1$H-NMR (DMSO-$d_6$) δ 7.52-7.46 (m, 2H), 7.45-7.38 (m, 2H), 7.21-7.13 (m, 1H), 7.12-7.03 (m, 4H), 6.64 (s, 1H), 3.99-3.90 (m, 1H), 3.29-3.22 (m, 2H), 3.03-2.90 (m, 2H), 2.48-2.36 (m, 2H), 2.03 (dd, J=13.9, 5.6 Hz, 2H), 2.14-1.99 (m, 1H), 1.97-1.85 (m, 1H), 1.65-1.15 (m, 3H).

Step 14: Synthesis of BG-13

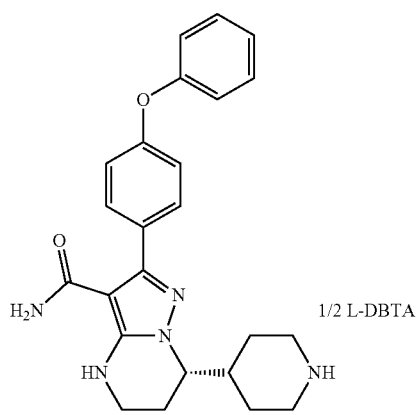

BG-13

1/2 L-DBTA

A mixture of MeOH (13.5 v), purified water (4.5 v) and BG-12 (8.5 Kg, 1.0 eq.) in a reactor was heated to 50° C. under $N_2$ atmosphere. To the mixture was charged dropwise a solution of L-DBTA (0.7 eq) in MeOH/purified water (1.5 v/0.5 v) while keeping the temperature at 50° C. After addition, the mixture was stirred for at least 2 hrs at 50° C., and then cooled to RT and stirred for at least 16 hrs at RT. The cake was collected by Centrifugation and was washed with MeOH (2.0 v). The cake was dried in a vacuum oven. This gave 9.08 Kg product (Yield: 74.8%).

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1)

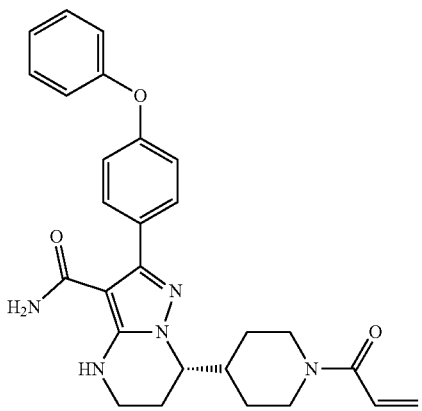 [SMILES: C=CC(=O)N1CCC([C@@H]2CCNc3c(C(N)=O)c(-c4ccc(Oc5ccccc5)cc4)nn32)CC1]

Under $N_2$ atmosphere, ACN (12.0 v), water (12.5 v), BG-13 (8.0 Kg, 1.0 eq), and $NaHCO_3$ (2.5 eq.) were added to a reactor. The mixture was then cooled to −5~0° C. To the mixture, the solution of acryloyl chloride (1.1 eq.) in MeCN (0.5 v) was added dropwise and stirred until the reaction was completed. EA (6.0 v) was then added to the reactor, and stirred. The organic phase was collected. The aqueous layer was further extracted with EA (3.0 v). The organic phases were combined and washed with brine. The organic layer was collected and concentrated.

The residue was purified by silica gel (2 wt) column, eluted with 3% w/w methanol in DCM (21.0 v). The Compound 1 solution was collected and concentrated under vacuum. The residue was precipitated from EA/MTBE (2.0 v). The cake was collected by centrifugation as the product.

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1, Alternative Method)

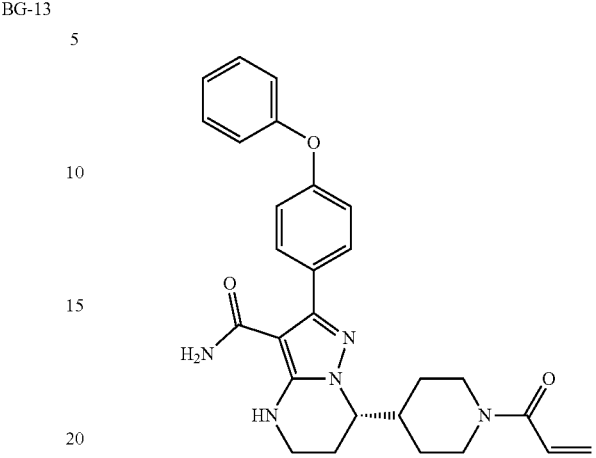

A mixture of $CH_3CN$ (10.0 v), purified water (5.0 v), NaOH (1.5 eq.) and BG-13 (1.0 eq.) was stirred to get a clear solution. EtOAc (6.0 v) was then charged to the reaction and separated. The organic phase was collected and washed with 15% brine (3.0 v) twice. The organic phase prepared above was concentrated and the solvent was swapped to $CH_3CN$ (residue volume: NMT 5.0 v). $CH_3CN$ (7.5 v) and purified water (12.5 v) were charged and cooled to 15-20° C. L-(+)-tartaric acid (0.5 eq) and $NaHCO_3$ (2.5 eq.) were charged to the reaction mixture. A solution of acryloyl chloride (1.1 eq.) in $CH_3CN$ (0.5 v) was charged drop-wise to the reaction mixture. After the reaction was completed, EtOAc (6.0 v) was charged to the reaction mixture and organic layer was collected. Aqueous phase was further extracted with EA (3.0 v). The organic layers were combined, washed with 15% brine (5.0 v) and concentrated. The solvent was swapped to DCM (volume of residue: 1.5-2.0 v) and purified by silica gel column (silica gel: 100-200 mush, 2.0 w/w; eluent: 3% w/w MeOH in DCM (about 50 v). The collected solution was concentrated and swapped to EtOAc (4.0 v). MTBE (6.4 v) was charged drop-wise to residue at 50° C. The mixture was then cooled to 5° C. and the cake was collected centrifugation.

Step 16: Preparation of Crystalline Form A of Compound 1

The above cake was dissolved in 7.0 volumes of DCM, and then swapped to solvent EA. After recrystallization from EA/MTBE, the cakes was collected by centrifugation, and was dried under vacuum. This gave 4.44 Kg product (Yield: 70.2%).

Figure 6:
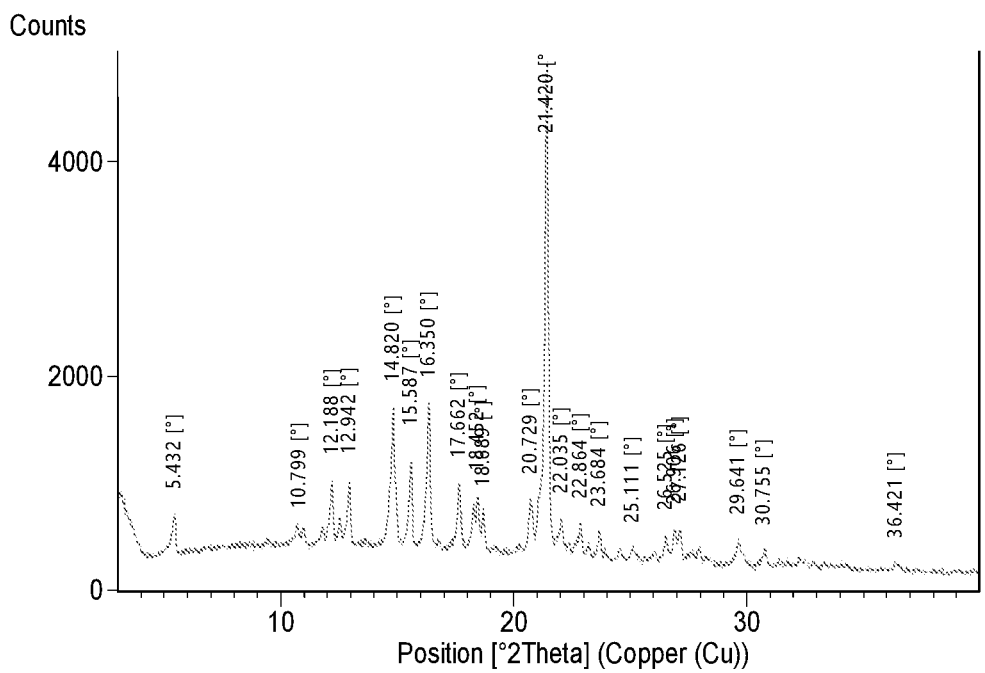
FIG. 6 shows an X-ray diffraction pattern of Compound 1 in a crystalline form.

The product was then characterized by X-ray powder diffraction (XRPD) pattern method, which was generated on a PANalytical Empyrean X-ray powder diffractometer with the XRPD parameters as follows: X-Ray wavelength (Cu, kα, Kα1 (Å): 1.540598, Kα2(Å): 1.544426; Kα2/Kα1 intensity ratio: 0.50); X-Ray tube setting (45 Kv, 40 mA); divergence slit (automatic); scan mode (Continuous); scan range (° 2TH) (3°-40); step size (° 2TH) (0.0131); scan speed (°/min) (about 10). The XRPD result found the resultant product as a crystalline shown in FIG. 6.

Figure 7:
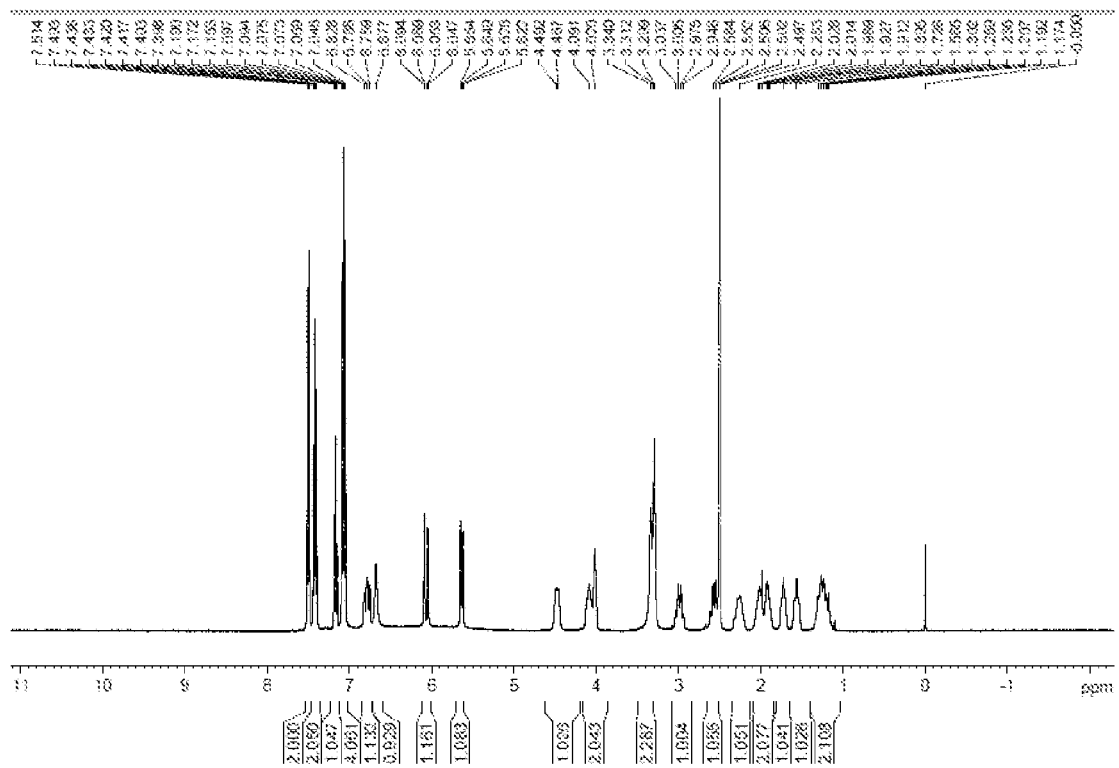
FIG. 7 shows $^1$H-NMR of the crystalline form of Compound 1.

The proton nuclear magnetic resonance ($^1$H-NMR) shown as in FIG. 7 was collected on a Bruker 400M NMR Spectrometer in DMSO-$d_6$. $^1$H-NMR (DMSO-$d_6$) δ 7.50 (d, J=8.6 Hz, 2H), 7.46-7.38 (m, 2H), 7.17 (t, J=7.6 Hz, 1H), 7.08 (d, J=7.6 Hz, 2H), 7.05 (d, J=8.8 Hz, 2H), 6.85-6.72 (m, 1H), 6.67 (s, 1H), 6.07 (dd, J=16.8, 2.2 Hz, 1H), 5.64 (dd, J=10.4 Hz, 2.2 Hz, 1H), 4.55-4.38 (m, 1H), 4.17-3.94 (m, 2H), 3.33-3.22 (m, 2H), 3.08-2.88 (m, 1H), 2.67-2.51 (m, 1H), 2.36-2.15 (m, 1H), 2.12-1.82 (m, 2H), 1.79-1.65 (m, 1H), 1.63-1.49 (m, 1H), 1.38-1.08 (m, 2H).

Figure 8:
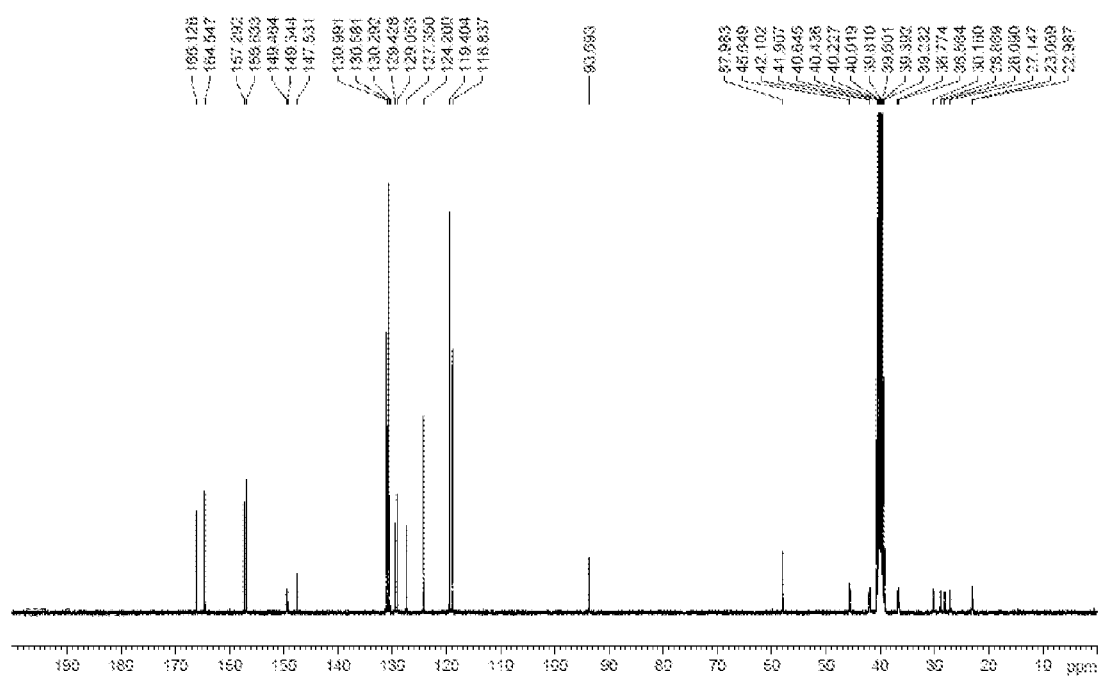
FIG. 8 shows $^{13}$C-NMR of the crystalline form of Compound 1.

The carbon nuclear magnetic resonance ($^3$C-NMR) shown as in FIG. 8 was collected on a Bruker 400M NMR Spectrometer in DMSO-$d_6$. $^{13}$C-NMR spectra for Crystalline Form A of Compound 1.

Example 2

Safety and Activity of BTK Inhibitor in Combination with PD-1 Inhibitor in Patients with B-Cell Lymphoid Malignancies Methodology First-in-human, open-label, multicenter, phase 1b trial was study to evaluate safety, tolerability, and preliminary efficacy (see FIG. 1) of Compound 1 in combination with Mab 1 in subjects with B-cell malignancies, including relapsed/refractory chronic lymphocytic leukemia (CLL)/small lymphocytic lymphoma (SLL), mantle cell lymphoma (MCL), non-germinal center B-cell (non-GCB) diffuse large B-cell lymphoma (DLBCL), GCB DLBCL or DLBCL with undetermined subtype, follicular lymphoma (FL), marginal zone lymphoma (MZL), hairy cell leukemia (HCL), transformed FL, Richter's transformation, primary central nervous system lymphoma (PCNSL), secondary CNS lymphoma (SCNSL) of breast or testicular origin, and transformed lymphoma. The study was divided into dose escalation and a dose expansion.

Study Treatment

Compound 1 was administered orally every day (320 mg QD or 160 mg BID) with or without food. Mab 1 was administered intravenously (2.0 mg/kg, 5.0 mg/kg, or 200 mg flat dose, depending on assigned dose level cohort) every 21 days (Q3W). When the 2 study drugs were administered on the same day (except on the days both PK samples are collected), Compound 1 was administered at least 30 minutes before Mab 1 infusion. All cycles included 21 days.

For dose escalation, Cycle 1 included 28 days and all subsequent cycles included 21 days. Compound 1 was administered on Cycle 1 Day 1 and then continuously every day. Mab 1 was administered on Cycle 1 Day 8 and then on Day 1 of all subsequent cycles. The period for DLT assessment was 21 days from Cycle 1 Day 8 to Cycle 1 Day 28.

For dose expansion, all cycles included 21 days. On Day 1 of each cycle, Compound 1 and Mab 1 were administered on the same day, except for 10 subjects of the CNS lymphoma cohort (Cohort 4B) as described below.

For PCNSL and SCNSL (Cohort 4A and 4B), 10 subjects (Cohort 4A) initially received single-agent Mab 1 for 4 cycles at 200 mg intravenously Q3W. On Day 1 of Cycle 5 and thereafter, the 10 subjects received combination Compound 1 and Mab 1 at the RP2D defined by the dose escalation. For Cohort 4B, 10 subjects with PCNSL and SCNSL received combination Compound 1 and Mab 1 at the RP2D defined by the dose escalation starting at Day 1 of Cycle 1 and all cycles thereafter. When the 2 drugs were administered on the same day (except on the days both PK samples to be collected), Compound 1 was administered at least 30 minutes before Mab 1 infusion. All cycles included 21 days.

Dose Escalation

The purpose of dose escalation is to determine the MTD for this study. During dose escalation, three dose levels were explored in the following order:

Dose level 1: Compound 1 320 mg QD in combination with Mab 1 2.0 mg/kg Q3W. If Dose Level 3 cleared, subjects were converted to dose level 3 dosing. Dose level −1 (applicable only if dose level 1 exceeds MTD): Compound 1 160 mg QD in combination with Mab 1 2.0 mg/kg Q3W. Further reductions of Compound 1 or Mab 1 dose levels may be allowed until a safe dose combination is identified.

Dose level 2: Compound 1 320 mg QD with Mab 1 5.0 mg/kg Q3W. If dose level 3 cleared, subjects were converted to dose level 3 dosing.

Dose level 3: Compound 1 160 mg BID with Mab 1 200 mg flat dose Q3W.

Dose escalation followed the same principles as stipulated for a standard 3+3 dose escalation design, with each cohort evaluated for safety based on the number of dose-limiting toxicities (DLTs) observed. Evaluation of a cohort of at least 3 subjects completing the DLT assessment at any given dose level is required prior to determining the next dose level and dose regimen for the subsequent cohort. Three subjects in the cohort is sufficient if no DLTs are observed within the DLT window for all 3 subjects. More than 3 subjects are required per cohort depending on the number of observed DLTs as follows:

<6 subjects enrolled in the cohort:
1 subject experiences a DLT during the DLT assessment period: the cohort must enroll a minimum of 6 subjects evaluable for DLT.
≥2 subjects experience a DLT during the DLT assessment period: the MTD is considered to have been exceeded, and no additional subjects will be treated at the current or higher doses.
≥6 subjects enrolled in the cohort:
1 subject experiences a DLT during the DLT assessment period: the cohort is considered tolerable and to not exceed the MTh.
≥33% of subjects (i.e., 2 out of 6) experience a DLT during the DLT assessment period: the MTD is considered to have been exceeded, and no additional subjects will be treated at the current or higher doses.

Dose Expansion

In the dose expansion, there were 4 dose expansion cohorts at the RP2D for the combination of Mab 1 and Compound 1:

Cohort 1 (n=20): GCB DLBCL
Cohort 2 (n=20): non-GCB DLBCL
Cohort 3 (n=20): Transformed lymphoid malignancy
Cohort 4: Primary CNS lymphoma or SCNSL of breast or testicular origin
  Cohort 4A (n=10): begin with 4 cycles of single-agent Compound 1 at 200 mg Q3W, combination of Compound 1 and Mab 1 starting Cycle 5
  Cohort 4B (n=10): combination of Compound 1 and Mab 1 starting Cycle 1

The cohorts for the dose expansion were defined in Inclusion Criterion 2. The dose and schedule of combination Compound 1 and Mab-1 were the RP2D as determined by the SMC for the non-CNS disease types (Cohorts 1 to 3). The dose and schedule of single-agent Mab 1 were 200 mg IV Q3W for Cohort 4, followed by the RP2D for the combination. Approximately 20 subjects were enrolled in each dose expansion part. Cohorts 1, 2, 3, and 4A opened simultaneously once the RP2D has been determined. Cohort 4B may not be enrolled until Cohort 4A has been completed.

Dose-Limiting Toxicity

A dose-Limiting Toxicity (DLT) is a toxicity or adverse event (AE) occurring during the DLT assessment period (21 days from Cycle 1 Day 8 to Cycle 1 Day 28), which cannot be primarily attributed to a cause other than Compound 1 and/or Mab 1 (such as disease progression, underlying illness, concurrent illness, or concomitant medication) and meets 1 of the following criteria:

1) Non-hematologic Grade 4 (or Grade 3 lasting >3 days) toxicity excluding:
 a. Laboratory abnormalities deemed by investigators as being not of serious nature
 b. Grade 3 tumor flare
 c. Grade 3 infusion-related event that resolves to Grade 1 within 28 days
 d. Grade 3 nausea or vomiting
 e. Grade 3 hypertension 2) Grade 4 neutropenia lasting >7 days, not attributable to leukemic or lymphomatous infiltration of the bone marrow 3) Grade 4 thrombocytopenia lasting >7 days, not attributable to leukemic or lymphomatous infiltration of the bone marrow 4) Any toxicity that requires drug hold of 1 or both investigational agents for more than 2 weeks.

Methods

Primary Endpoint
Dose escalation: The MTD and/or recommended Phase 2 dose (RP2D) of Mab 1 in combination with Compound 1, as determined based on the incidence of protocol-defined dose-limiting toxicities, safety, tolerability, and PK profile.
Dose expansion: The safety and tolerability of combination Compound 1 and Mab 1 (Cohorts 1 to 3, and 4B), or single agent Mab 1 followed by combination Compound 1 and Mab 1 (Cohort 4A) in previously treated subjects with B-cell malignancies, as assessed by the occurrence and severity of AEs (Common Terminology Criteria for Adverse Events [CTCAE], version 4).

Secondary Endpoints
The antitumor activity of the combination of Compound 1 and Mab 1 (Cohorts 1 to 3, and 4A), or single-agent Mab 1, followed by combination Compound 1 and Mab 1 (Cohort 4B) in previously treated subjects with specified B-cell malignancies, as determined by overall response rate (ORR, defined as the proportion of subjects who had complete response [CR] or partial response [PR] by standard disease-specific response criteria), duration of response ([DOR]; defined as the time from the date that a confirmed objective response is first documented to the date of progressive disease [PD] or death due to any cause for those subjects with a confirmed PR or CR), and progression-free survival ([PFS]; defined as the time from the first dose of study medication to objective disease progression or death).
The PK profiles of Mab 1 and Compound 1.
The incidence of development of anti-drug antibody to Mab 1 when given in combination with Compound 1.

Results

Figure 2:
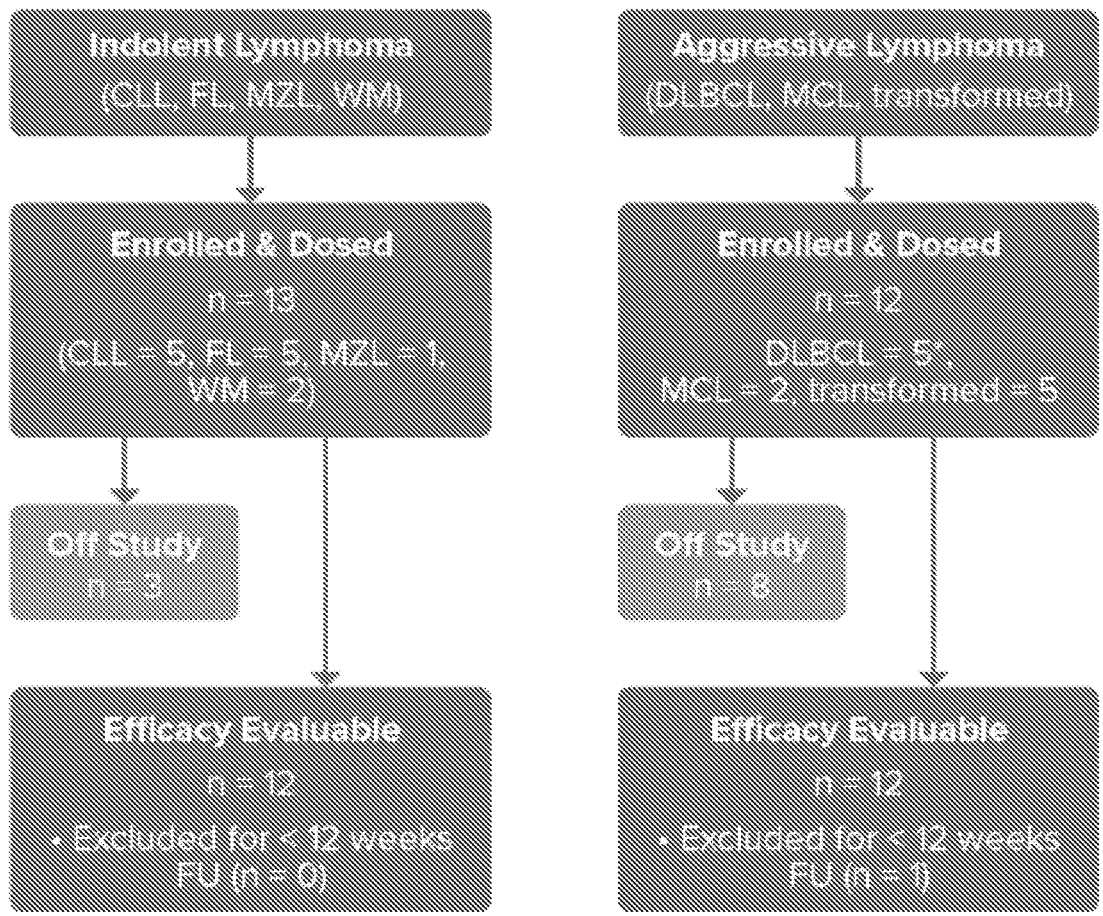
FIG. 2 shows the patient disposition at the current cutoff.

Patient disposition at the current cutoff is shown in FIG. 2. The median follow up is about 5.1 months (rang 0.4-14.1); 5.1 (1.6-14.1) and 4.2 (0.4-14.4) for indolent and aggressive lymphoma, respectively.

The patients and disease characteristics are listed in Table 1-A. The best response is listed in Table 1-B.

The DLT assessment period is 21 days from Cycle 1 Day 8 to Cycle 1 Day 28. In cohort 2, two events of hemolysis, 1 of which met criteria for DLT, see Table 2. Both events were in patients with WM and additional patients with WM were excluded form enrollment in trail, and no further DLT events following WM exclusion.

TABLE 1-A

Patients and Disease Characteristics

| Characteristic | Indolent (n = 13) | Aggressive (n = 12) | Total (N = 25) |
|---|---|---|---|
| Age, years, median (range) | 62 (47-76) | 62.5 (27-71) | 62 (27-76) |
| ECOG performances status, n (%) | | | |
| 0 | 7 (53.8) | 3 (25) | 10 (40) |
| 1 | 3 (23.1) | 7 (58.3) | 10 (40) |
| 2 | 3 (23.1) | 1 (8,3) | 4 (16) |
| 3 | 0 | 1 (8.3) | 1 (4) |
| Follow-up, months, median (range) | 5.1 (1.6-14.1) | 4.2 (0.4-14.1) | 5.1 (0.4-14.1) |
| Number of prior therapies, median range) | 4 (1-6) | 4 (1-6) | 4 (1-6) |
| Bulky disease,* n (%) | 1 (7.7) | 1 (8.3) | 2 (8) |
| Dose 1 (Compound 1 320 mg QD, Mab-1 2.0 mg/kg Q3W) | 7 (53.8) | 8 (66.7) | 15 (60) |
| Dose 2 (Compound 1 320 mg QD, Mab-1 5.0 mg/kg Q3W) | 6 (46.2) | 4 (33.3) | 10 (40) |

ECOG, Eastern Cooperative Oncology Group;
GBC, germinal center B-cell;
LDH, lactate dehydroganase;
Q3W, every 3 weeks;
QD, once daily.
*Any lymph node >10 cm in maximum diameter.

TABLE 1-B

| | Best Response | | |
|---|---|---|---|
| Response | Indolent n (%) | Aggressive n (%) | Total n (%) |
| Efficacy evaluable, n | 12 | 12 | 24 |
| Best Response, n (%) | | | |
| ORR | 4 (33.3) | 4 (33.3) | 8 (33.3) |
| CR | 1 (8.3) | 1 (8.3) | 2 (8.3) |
| VGPR | 1 (3.3) | — | 1 (4.2) |
| PR/PR-L | 1 (8.3) | 3 (25) | 4 (16.7) |
| MR | 1 (8.3) | — | 1 (4.2) |
| SD | 4 (33.3) | 3 (25) | 7 (29.2) |
| PD | 2 (16.7) | 5 (41.7) | 7 (29.2) |
| Discontinuation or NE or ND* | 2 (16.7) | 0 | 2 (8.3) |

CR, complete response;
MR, minor response;
ND, not defined;
NE, not evaluable;
ORR, overall response rate;
PD, progressive disease;
PR, partial response;
PR-L, partial response with lymphocytosis;
SD, stable disease;
VGPR, very good partial response.
*Patient discontinued for reason other than PD before 1st response assessment or response assessment was NE or scheduled response assessment was not done.

TABLE 2

| | Dose-Limiting Toxicity | | |
|---|---|---|---|
| Dose Level | Enrolled | Cohort Status | DLTs |
| Dose 1 (2.0 mg/kg Q3W) | 15 | Complete | None |
| Dose 2 (5.0 mg/kg Q3W) | 10 | Complete | 1 Hemolysis (WM) |
| Dose 3 (200 mg flat Q3W) | 0 | Open | (patients have yet to receive drug) |

DLT, dose-limiting toxicity;
WM, Waldenström's macroglobulinemia.

Figure 3A:
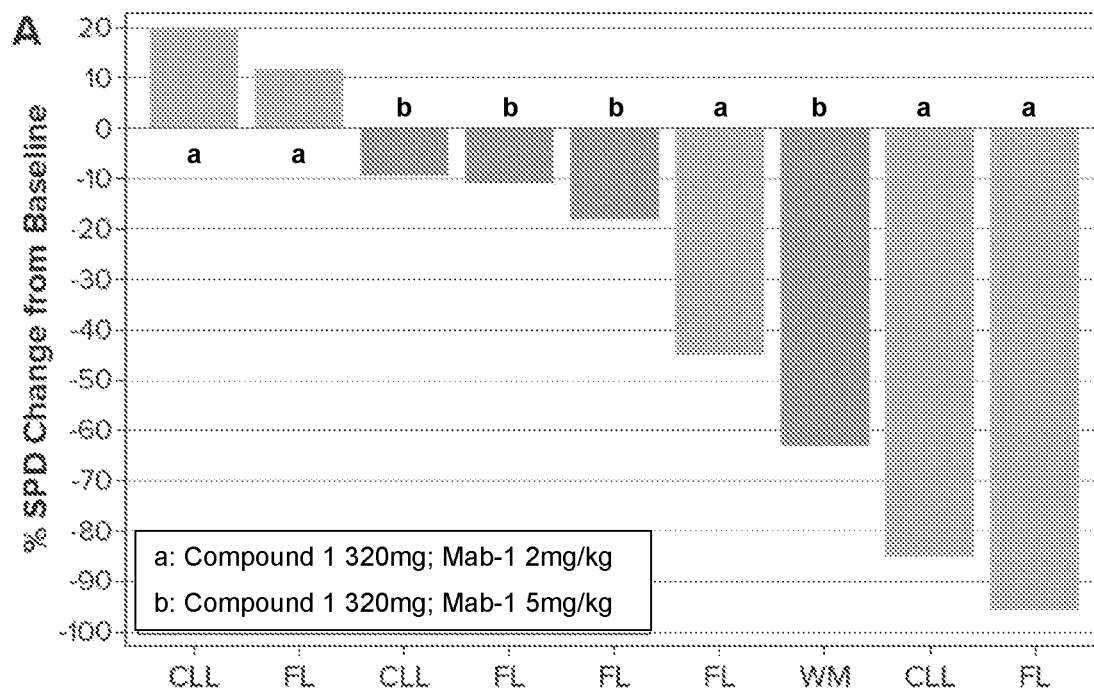
FIG. 3A and FIG. 3B show Maximum Improvement in SPD in patients with indolent and aggressive lymphoma, respectively.
Figure 3B:
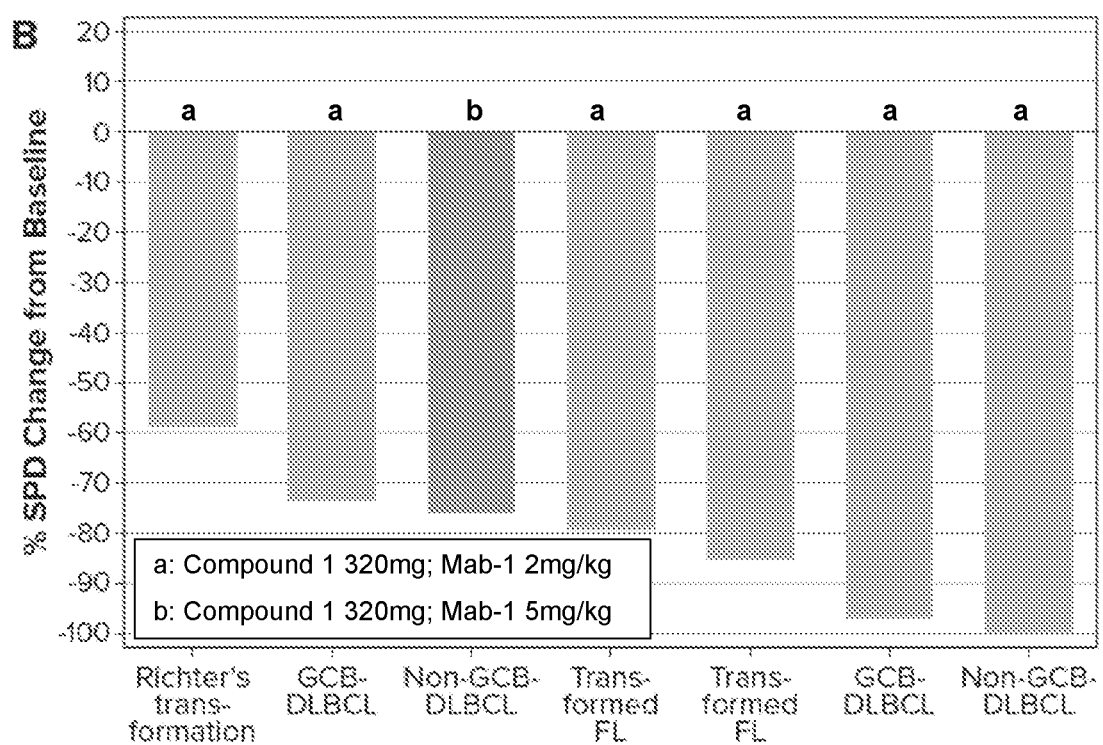
Figure 4A:
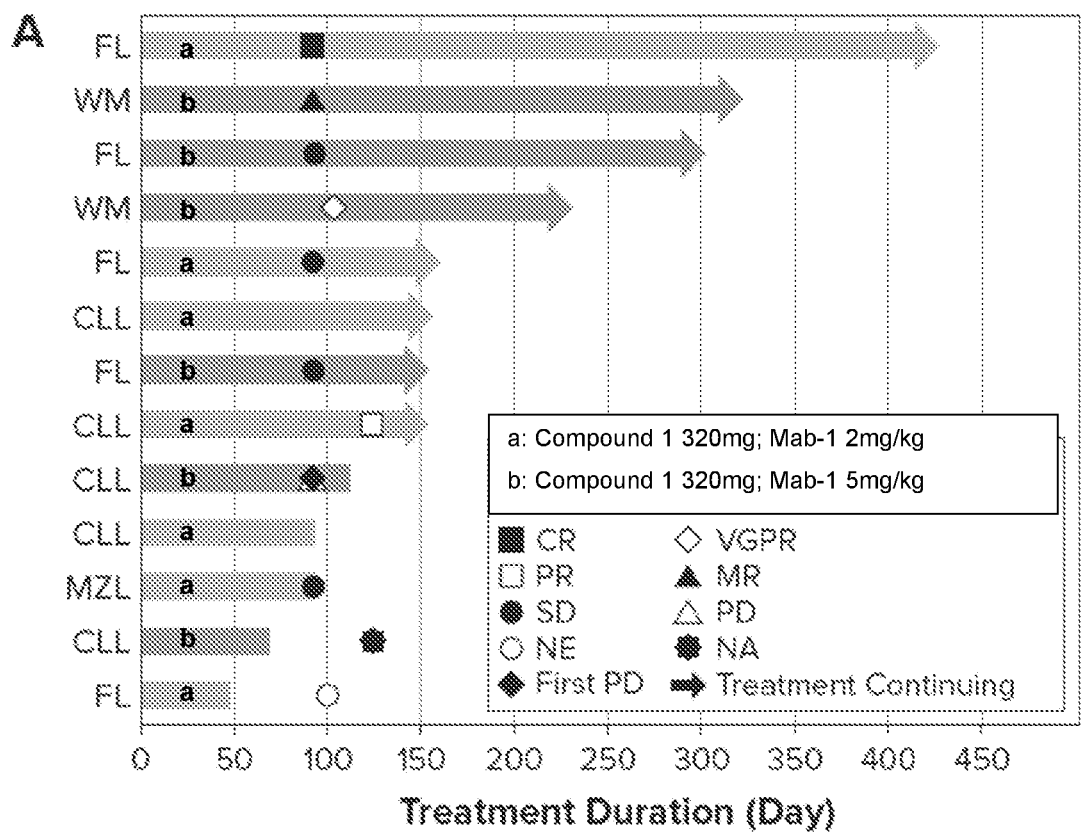
FIG. 4A and FIG. 4B show duration of treatment in patients with indolent and aggressive lymphoma, respectively.
Figure 4B:
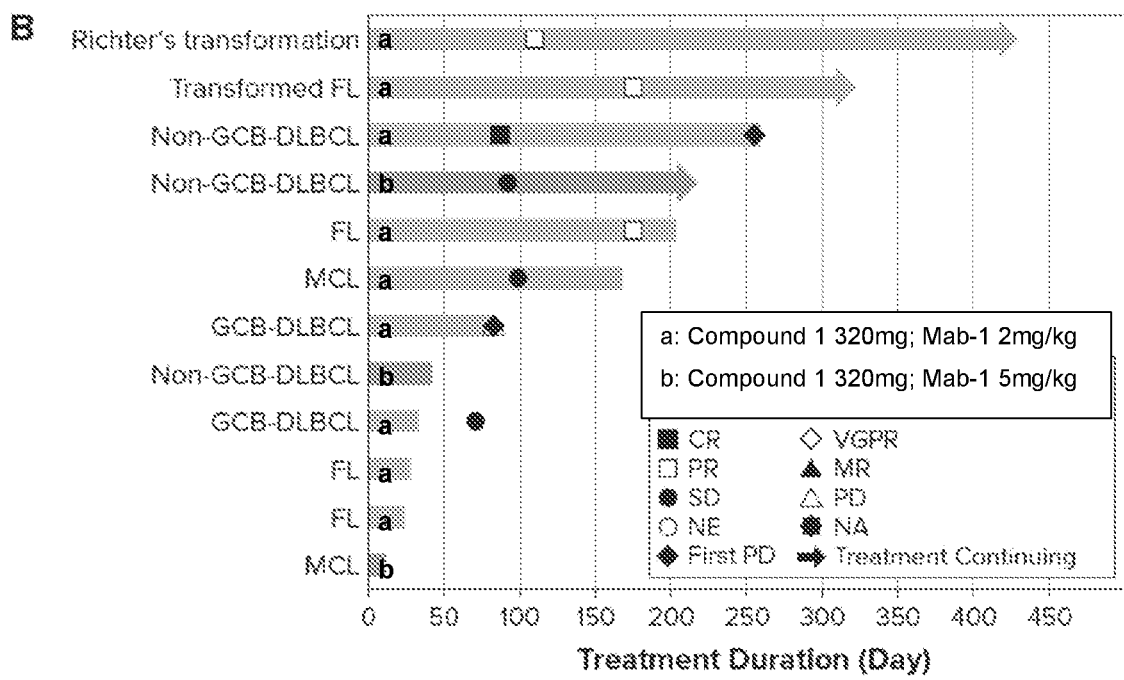
Figure 5A:
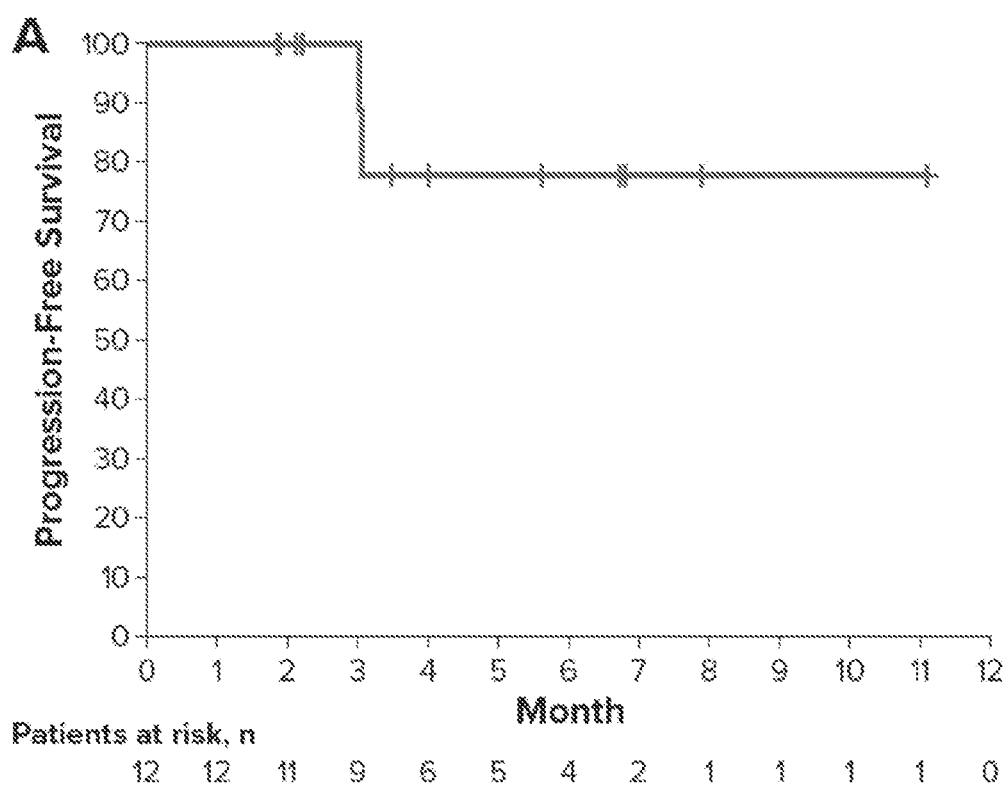
FIG. 5A and FIG. 5B show progression-free survival in patients with indolent and aggressive lymphoma, respectively.
Figure 5B:
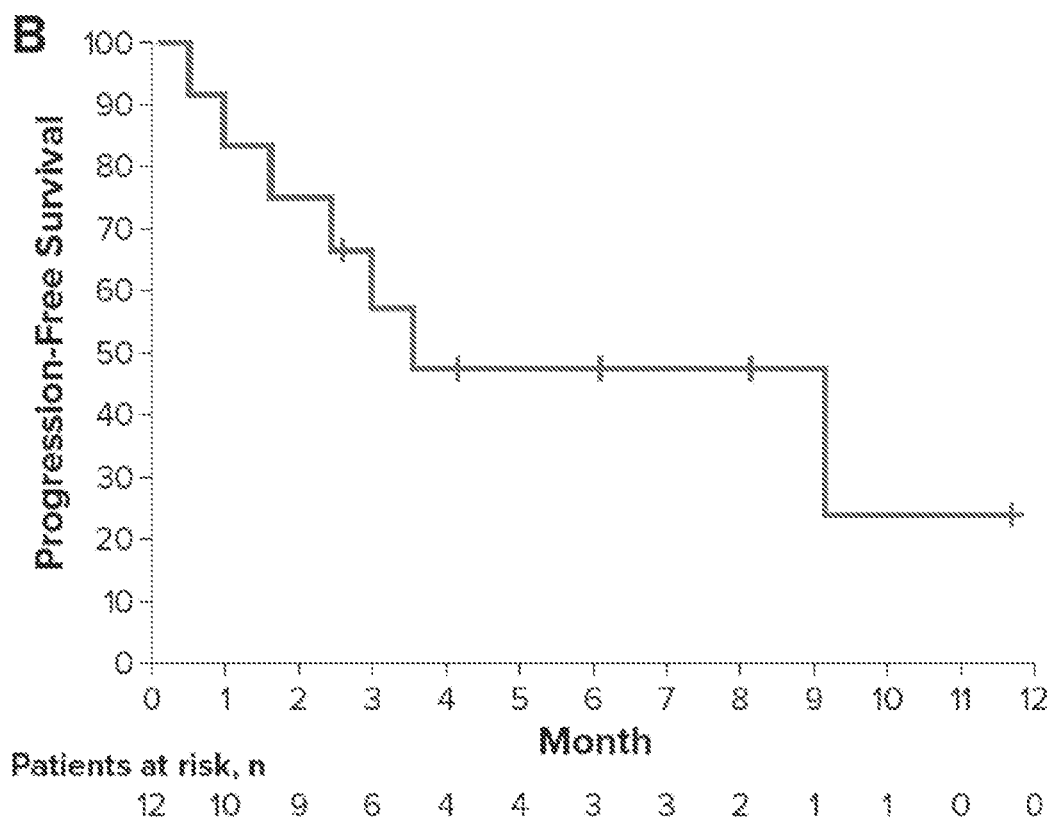

The combination of Compound 1 and Mab 1 was found to achieve maximum improvement in SPD (sum of the products of lymph node diameters by CT scan) in patients with indolent and aggressive lymphoma, respectively, as shown in FIGS. 3A and 3B. Also, the combination was found to extend the life of some of the patents enrolled with indolent and aggressive lymphoma, respectively, as shown in FIG. 4A and FIG. 4B, and to elongate progression-free survival in patients with indolent and aggressive lymphoma, respectively, as shown in FIG. 5A and FIG. 5B. In conclusion, the potent and selective BTK inhibitor in combination with the checkpoint PD1 inhibitor have a manageable toxicity profile in patients with in a wide variety of B-cell malignancies, including indolent and aggressive lymphomas.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

The invention claimed is:

1. A method for the delay of progression or treatment of an indolent or aggressive B-cell lymphoma in a human in need thereof, comprising administering to the human a therapeutically effective amount of a BTK inhibitor, in combination with a therapeutically effective amount of an anti-PD-1 antibody or an antigen-binding fragment thereof, wherein the BTK inhibitor is (S)-7-(1-acryloylpiperidin-4-yl)-2-(4-phenoxyphenyl)-4,5,6,7-tetra-hydropyrazolo[1,5-a]pyrimidine-3-carboxamide, or a pharmaceutically acceptable salt thereof;
and
the anti-PD-1 antibody or fragment comprises a heavy chain variable region (Vh) amino acid sequence of SEQ ID NO:24 and a light chain variable region (Vl) amino acid sequence of SEQ ID NO:26.

2. The method of claim 1, wherein the anti-PD-1 antibody or fragment comprises an IgG4 constant domain amino acid sequence of SEQ ID NO 88.

3. The method of claim 1, wherein the indolent or aggressive B-cell lymphoma is indolent or aggressive Hodgkin's B-cell lymphoma, or indolent or aggressive non-Hodgkin's B-cell lymphoma.

4. The method of claim 3, wherein the B-cell lymphoma is chronic lymphocytic leukemia (CLL), small lymphocytic lymphoma (SLL), mantle cell lymphoma (MCL), non-germinal center B-cell diffuse large B-cell lymphoma (non-GCB DLBCL), germinal center B-cell diffuse large B-cell lymphoma (GCB DLBCL) or DLBCL with undetermined subtype, follicular lymphoma (FL) or transformed FL, marginal zone lymphoma (MZL), Hairy cell leukemia (HCL), Richter's transformation, primary central nervous system lymphoma (PCNSL), secondary central nervous system lymphoma (SCNSL) of breast or testicular origin, transformed lymphoma, or a combination of two or more thereof.

5. The method of claim 3, wherein the B-cell lymphoma is CLL, SLL, MCL, non-GCB DLBCL, GCB DLBCL, FL, transformed FL, MZL, HCL, or Richter's transformation.

6. The method of claim 1, wherein the BTK inhibitor is (S)-7-(1-acryloylpiperidin-4-yl)-2-(4-phenoxyphenyl)-4,5, 6,7-tetra-hydropyrazolo[1,5-a]pyrimidine-3-carboxamide.

7. The method of claim 1, wherein the BTK inhibitor is administered orally at a dose of 320 mg QD or 160 mg BID.

8. The method of claim 7, wherein the BTK inhibitor is administered without food.

9. The method of claim 2, wherein the anti-PD-1 antibody is administered parenterally at a dose of 2 mg/kg Q3W to 200 mg/kg Q3W.

10. The method of claim 2, wherein the anti-PD-1 antibody is administered parenterally at a dose of 2 mg/kg Q3W, 5 mg/kg Q3W, or 200 mg flat Q3W.

11. The method of claim 10, wherein the anti-PD-1 antibody is administered at a dose of 200 mg flat dose every 21 days.

12. The method of claim 2, wherein the anti-PD-1 antibody is administered intravenously.

13. The method of claim 2, wherein the BTK inhibitor is administered at least 30 minutes before the anti-PD-1 antibody if administered on the same day.

14. The method of claim 7, wherein the BTK inhibitor is administered with food.

15. The method of claim 1, wherein the method is a method of delay of progression or treatment of an indolent or aggressive B-cell lymphoma; wherein the BTK inhibitor is administered orally at a dose of 320 mg QD or 160 mg BID; and wherein the anti-PD-1 antibody or fragment is administered intravenously at a dose of 2 mg/kg Q3W, 5 mg/kg Q3W, or 200 mg Q3W.

16. The method of claim 15, wherein the anti-PD-1 antibody or fragment comprises an IgG4 constant domain amino acid sequence of SEQ ID NO 88.

* * * * *

SEQUENCE LISTING

<160> NUMBER OF SEQ ID NOS: 107

<210> SEQ ID NO 1
<211> LENGTH: 444
<212> TYPE: DNA
<213> ORGANISM: Homo sapiens

<400> SEQUENCE: 1

```
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
tacctctgtg gggccatctc cctggccccc aaggcgcaga tcaaagagag cctgcgggca     360
gagctcaggg tgacagagag aaagggcagaa gtgcccacag cccacccccag cccctcaccc   420 aggccagccg gccagttcca aacc                                            444
```

<210> SEQ ID NO 2
<211> LENGTH: 148
<212> TYPE: PRT
<213> ORGANISM: Homo sapiens

<400> SEQUENCE: 2

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr
145
```

```
<210> SEQ ID NO 3
<211> LENGTH: 354
<212> TYPE: DNA
<213> ORGANISM: Mus musculus

<400> SEQUENCE: 3
caggtgcagc tgaaggagtc aggacctggc ctggtggcgc cctcaaagaa cctgtccatc      60
acttgcactg tctctgggtt ttcattaacc agctatggtg tacactggat tcgccagcct     120
ccaggaaagg gactggaatg gctgggagta atatgggccg gtggaagcac aaattataat     180
tcggctctca gtccagact  gagcatcagc aaagacaact ccaggagcca agttttctta     240
agaatgaaca gtctgcaaac tgatgacaca gccatgtact actgtgccag agcctatggt     300
aactactggt acatcgatgt ctggggcgca gggaccacgg tcaccgtctc ctca           354
```

```
<210> SEQ ID NO 4
<211> LENGTH: 118
<212> TYPE: PRT
<213> ORGANISM: Mus musculus

<400> SEQUENCE: 4

Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Thr Asp Asp Thr Ala Met Tyr Tyr Cys Ala
                85                  90                  95

Arg Ala Tyr Gly Asn Tyr Trp Tyr Ile Asp Val Trp Gly Ala Gly Thr
            100                 105                 110
```

Thr Val Thr Val Ser Ser
        115

<210> SEQ ID NO 5
<211> LENGTH: 321
<212> TYPE: DNA
<213> ORGANISM: Mus musculus

<400> SEQUENCE: 5
gacattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gataaactat gcatttcatc gcttcactgg agtccctgat   180
cgtttcactg gcagtggata tgggacggat tcatttttca ccatcagcac tgtgcaggct   240
gaagacctgg cagtttattt ctgtcaccag gcttatagtt ctccgtacac gttcggaggg   300
gggaccaagc tggaaatgaa a                                              321

<210> SEQ ID NO 6
<211> LENGTH: 107
<212> TYPE: PRT
<213> ORGANISM: Mus musculus

<400> SEQUENCE: 6

Asp Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Phe His Arg Phe Thr Gly Val Pro Asp Arg Phe Thr Gly
    50                  55                  60

Ser Gly Tyr Gly Thr Asp Phe Ile Phe Thr Ile Ser Thr Val Gln Ala
65                  70                  75                  80

Glu Asp Leu Ala Val Tyr Phe Cys His Gln Ala Tyr Ser Ser Pro Tyr
                85                  90                  95

Thr Phe Gly Gly Gly Thr Lys Leu Glu Met Lys
            100                 105

<210> SEQ ID NO 7
<211> LENGTH: 342
<212> TYPE: DNA
<213> ORGANISM: Mus musculus

<400> SEQUENCE: 7
cagatccagt tggtgcagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacaata ataatggaga gccaacatat   180
gctgaagagt tcaagggacg gtttgccttc tctttgaaa cctctgccag cactgcctat   240
ttgcagatca caacctcaa aaatgaggac acggctacat atttctgtgc aagagatgtt   300
atggactatt ggggtcaagg aacctcagtc accgtctcct ca                     342

<210> SEQ ID NO 8
<211> LENGTH: 114
<212> TYPE: PRT
<213> ORGANISM: Mus musculus

<400> SEQUENCE: 8

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Asn Asn Gly Glu Pro Thr Tyr Ala Glu Glu Phe
    50                  55                  60

Lys Gly Arg Phe Ala Phe Ser Leu Glu Thr Ser Ala Ser Thr Ala Tyr
65              70                  75                  80

Leu Gln Ile Asn Asn Leu Lys Asn Glu Asp Thr Ala Thr Tyr Phe Cys
            85                  90                  95

Ala Arg Asp Val Met Asp Tyr Trp Gly Gln Gly Thr Ser Val Thr Val
            100                 105                 110

Ser Ser
```

```
<210> SEQ ID NO 9
<211> LENGTH: 330
<212> TYPE: DNA
<213> ORGANISM: Mus musculus

<400> SEQUENCE: 9
gacattgtgc tgacccaatc tccagcttct ttggctgtgt ctctagggca gagggccacc      60
atatcctgca gagccagtga agtgttgat aattatggct atagttttat gcactggtac     120
cagcagaaac aggacagcc accccaactc ctcatctatc gtgcatccaa cctagaatct     180
gggatccctg ccaggttcag tggcagtggg tctaggacag gcttcaccct caccattaat     240
cctgtggagg ctgatgatgt tgcaacctat tactgtcagc aaagtaaaga atatccgacg     300
ttcggtggag gcaccaagct ggaagtcaaa                                      330
```

```
<210> SEQ ID NO 10
<211> LENGTH: 110
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Gln Leu Leu Ile Tyr Arg Ala Ser Asn Leu Glu Ser Gly Ile Pro Ala
    50                  55                  60

Arg Phe Ser Gly Ser Gly Ser Arg Thr Gly Phe Thr Leu Thr Ile Asn
65              70                  75                  80

Pro Val Glu Ala Asp Asp Val Ala Thr Tyr Tyr Cys Gln Gln Ser Lys
            85                  90                  95

Glu Tyr Pro Thr Phe Gly Gly Gly Thr Lys Leu Glu Val Lys
            100                 105                 110
```

```
<210> SEQ ID NO 11
<211> LENGTH: 10
<212> TYPE: PRT
<213> ORGANISM: Mus musculus
```

```
<400> SEQUENCE: 11

Gly Phe Ser Leu Thr Ser Tyr Gly Val His
1               5                   10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 12
<212> TYPE: PRT
<213> ORGANISM: Mus musculus

<400> SEQUENCE: 13

Ala Arg Ala Tyr Gly Asn Tyr Trp Tyr Ile Asp Val
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Ser Asn Asp Val Ala
1               5                   10

<210> SEQ ID NO 15
<211> LENGTH: 7
<212> TYPE: PRT
<213> ORGANISM: Mus musculus

<400> SEQUENCE: 15

Tyr Ala Phe His Arg Phe Thr
1               5

<210> SEQ ID NO 16
<211> LENGTH: 9
<212> TYPE: PRT
<213> ORGANISM: Mus musculus

<400> SEQUENCE: 16

His Gln Ala Tyr Ser Ser Pro Tyr Thr
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Tyr Gly Met Asn
1               5                   10

<210> SEQ ID NO 18
<211> LENGTH: 17
<212> TYPE: PRT
<213> ORGANISM: Mus musculus

<400> SEQUENCE: 18
```

```
Trp Ile Asn Asn Asn Asn Gly Glu Pro Thr Tyr Ala Glu Glu Phe Lys
1               5                   10                  15

Gly

<210> SEQ ID NO 19
<211> LENGTH: 7
<212> TYPE: PRT
<213> ORGANISM: Mus musculus

<400> SEQUENCE: 19

Ala Arg Asp Val Met Asp Tyr
1               5

<210> SEQ ID NO 20
<211> LENGTH: 15
<212> TYPE: PRT
<213> ORGANISM: Mus musculus

<400> SEQUENCE: 20

Arg Ala Ser Glu Ser Val Asp Asn Tyr Gly Tyr Ser Phe Met His
1               5                   10                  15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Mus musculus

<400> SEQUENCE: 22

Gln Gln Ser Lys Glu Tyr Pro Thr
1               5

<210> SEQ ID NO 23
<211> LENGTH: 354
<212> TYPE: DNA
<213> ORGANISM: Artificial Sequence
<220> FEATURE:
<223> OTHER INFORMATION: 317-4B6 cDNA-Vh

<400> SEQUENCE: 23
caggtgcagc tgcaggagtc gggaccagga ctggtgaagc cttcggagac cctgtccctc      60
acctgcactg tctctgggtt ttcattaacc agctatggtg tacactggat ccggcagccc     120
ccagggaagg gactggagtg gatcggggtc atatacgccg atggaagcac aaattataat     180
ccctccctca gagtcgagt gaccatatca aagacacct caagaacca ggtttccctg        240 aagctgagct ctgtgaccgc tgcggacacg gccgtgtatt actgtgcgag agcctatggt     300
aactactggt acatcgatgt ctggggccaa gggaccacgg tcaccgtctc ctca           354

<210> SEQ ID NO 24
<211> LENGTH: 118
<212> TYPE: PRT
<213> ORGANISM: Artificial Sequence
<220> FEATURE:
<223> OTHER INFORMATION: 317-4B6 pro-Vh
```

<400> SEQUENCE: 24

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
Gly Val His Trp Ile Arg Gln Pro Pro Gly Lys Gly Leu Glu Trp Ile
        35                  40                  45
Gly Val Ile Tyr Ala Asp Gly Ser Thr Asn Tyr Asn Pro Ser Leu Lys
    50                  55                  60
Ser Arg Val Thr Ile Ser Lys Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Ala Tyr Gly Asn Tyr Trp Tyr Ile Asp Val Trp Gly Gln Gly Thr
            100                 105                 110
Thr Val Thr Val Ser Ser
        115

<210> SEQ ID NO 25
<211> LENGTH: 321
<212> TYPE: DNA
<213> ORGANISM: Artificial Sequence
<220> FEATURE:
<223> OTHER INFORMATION: 317-4B6 cDNA-Vk

<400> SEQUENCE: 25
gacatcgtga tgacccagtc tccagactcc ctggctgtgt ctctgggcga gagggccacc      60
atcaactgca gtccagcga gagtgtgagt aatgatgtag cttggtacca gcagaaacca     120
ggacagcctc ctaagctgct cattaactat gcatttcatc gcttcactgg ggtccctgac     180
cgattcagtg gcagcgggta tgggacagat ttcactctca ccatcagcag cctgcaggct     240
gaagatgtgg cagtttatta ctgtcaccag gcttatagtt ctccgtacac gtttggccag     300
gggaccaagc tggagatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: 317-4B6 pro-Vk

<400> SEQUENCE: 26

Asp Ile Val Met Thr Gln Ser Pro Asp Ser Leu Ala Val Ser Leu Gly
1               5                   10                  15
Glu Arg Ala Thr Ile Asn Cys Lys Ser Ser Glu Ser Val Ser Asn Asp
            20                  25                  30
Val Ala Trp Tyr Gln Gln Lys Pro Gly Gln Pro Pro Lys Leu Leu Ile
        35                  40                  45
Asn Tyr Ala Phe His Arg Phe Thr Gly Val Pro Asp Arg Phe Ser Gly
    50                  55                  60
Ser Gly Tyr Gly Thr Asp Phe Thr Leu Thr Ile Ser Ser Leu Gln Ala
65                  70                  75                  80
Glu Asp Val Ala Val Tyr Tyr Cys His Gln Ala Tyr Ser Ser Pro Tyr
                85                  90                  95
Thr Phe Gly Gln Gly Thr Lys Leu Glu Ile Lys
            100                 105

<210> SEQ ID NO 27
<211> LENGTH: 342
<212> TYPE: DNA
<213> ORGANISM: Artificial Sequence
<220> FEATURE:
<223> OTHER INFORMATION: 326-4A3 cDNA-Vh

<400> SEQUENCE: 27

```
caggtgcagc tggtgcagag cggcagcgag ctgaagaagc ccggcgccag cgtgaaggtg    60
agctgcaagg ccagcggcta caccttcacc aactacggca tgaactgggt gagacaggcc   120
cccggccagg gcctgaagtg gatgggctgg atcaacaaca acaacgccga gcccacctac   180
gcccaggact tcagaggcag attcgtgttc agcctggaca ccagcgccag caccgcctac   240
ctgcagatca gcagcctgaa gaccgaggac accgccgtgt actactgcgc cagagacgtg   300
atggactact ggggccaggg caccctggtg accgtgagca gc                      342
```

<210> SEQ ID NO 28
<211> LENGTH: 114
<212> TYPE: PRT
<213> ORGANISM: Artificial Sequence
<220> FEATURE:
<223> OTHER INFORMATION: 326-4A3 pro-Vh

<400> SEQUENCE: 28

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Ala Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser
```

<210> SEQ ID NO 29
<211> LENGTH: 330
<212> TYPE: DNA
<213> ORGANISM: Artificial Sequence
<220> FEATURE:
<223> OTHER INFORMATION: 326-4A3 cDNA-Vk

<400> SEQUENCE: 29

```
gacattgtgc tgacccagtc tccagcctcc ttggccgtgt ctccaggaca gagggccacc    60
atcacctgca gagccagtga aagtgttgat aattatggct atagttttat gcactggtat   120
cagcagaaac aggacaaacc tcctaaactc ctgatttacc gtgcatccaa cctagaatct   180
ggggtcccag ccaggttcag cggcagtggg tctgggaccg atttcaccct cacaattaat   240
cctgtggaag ctgaggatac tgcaaattat tactgtcagc aaagtaaaga atatccgacg   300
ttcggcggag ggaccaaggt ggagatcaaa                                    330
```

<210> SEQ ID NO 30

```
<211> LENGTH: 110
<212> TYPE: PRT
<213> ORGANISM: Artificial Sequence
<220> FEATURE:
<223> OTHER INFORMATION: 326-4A3 pro-Vk

<400> SEQUENCE: 30

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 31
<211> LENGTH: 10
<212> TYPE: PRT
<213> ORGANISM: Mus musculus

<400> SEQUENCE: 31

Gly Phe Ser Leu Thr Ser Tyr Gly Val His
1               5                   10

<210> SEQ ID NO 32
<211> LENGTH: 16
<212> TYPE: PRT
<213> ORGANISM: Artificial Sequence
<220> FEATURE:
<223> OTHER INFORMATION: 317-4B6 H-CDR2 or CDR-H2

<400> SEQUENCE: 32

Val Ile Tyr Ala Asp Gly Ser Thr Asn Tyr Asn Pro Ser Leu Lys Ser
1               5                   10                  15

<210> SEQ ID NO 33
<211> LENGTH: 12
<212> TYPE: PRT
<213> ORGANISM: Mus musculus

<400> SEQUENCE: 33

Ala Arg Ala Tyr Gly Asn Tyr Trp Tyr Ile Asp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: 317-4B6 L-CDR1 or CDR-L1

<400> SEQUENCE: 34

Lys Ser Ser Glu Ser Val Ser Asn Asp Val Ala
1               5                   10

<210> SEQ ID NO 35
```

-continued

<210> SEQ ID NO 35
<211> LENGTH: 7
<212> TYPE: PRT
<213> ORGANISM: Mus musculus

<400> SEQUENCE: 35

Tyr Ala Phe His Arg Phe Thr
1               5

<210> SEQ ID NO 36
<211> LENGTH: 9
<212> TYPE: PRT
<213> ORGANISM: Mus musculus

<400> SEQUENCE: 36

His Gln Ala Tyr Ser Ser Pro Tyr Thr
1               5

<210> SEQ ID NO 37
<211> LENGTH: 10
<212> TYPE: PRT
<213> ORGANISM: Mus musculus

<400> SEQUENCE: 37

Gly Tyr Thr Phe Thr Asn Tyr Gly Met Asn
1               5                   10

<210> SEQ ID NO 38
<211> LENGTH: 17
<212> TYPE: PRT
<213> ORGANISM: Artificial Sequence
<220> FEATURE:
<223> OTHER INFORMATION: 326-4A3 H-CDR2 or CDR-H2

<400> SEQUENCE: 38

Trp Ile Asn Asn Asn Asn Ala Glu Pro Thr Tyr Ala Gln Asp Phe Arg
1               5                   10                  15

Gly

<210> SEQ ID NO 39
<211> LENGTH: 7
<212> TYPE: PRT
<213> ORGANISM: Mus musculus

<400> SEQUENCE: 39

Ala Arg Asp Val Met Asp Tyr
1               5

<210> SEQ ID NO 40
<211> LENGTH: 15
<212> TYPE: PRT
<213> ORGANISM: Mus musculus

<400> SEQUENCE: 40

Arg Ala Ser Glu Ser Val Asp Asn Tyr Gly Tyr Ser Phe Met His
1               5                   10                  15

<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Mus musculus

<400> SEQUENCE: 42

Gln Gln Ser Lys Glu Tyr Pro Thr
1               5

<210> SEQ ID NO 43
<211> LENGTH: 118
<212> TYPE: PRT
<213> ORGANISM: Artificial Sequence
<220> FEATURE:
<223> OTHER INFORMATION: 317-4B2 pro-Vh

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: 317-4B2 pro-Vk

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 45
<211> LENGTH: 118

<212> TYPE: PRT
<213> ORGANISM: Artificial Sequence
<220> FEATURE:
<223> OTHER INFORMATION: 317-4B5 pro-Vh

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 317-4B5 pro-Vk

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 47
<211> LENGTH: 354
<212> TYPE: DNA
<213> ORGANISM: Artificial Sequence
<220> FEATURE:
<223> OTHER INFORMATION: 317-1 cDNA-Vh

<400> SEQUENCE: 47
caggtgcagc tgcaggagtc gggaccagga ctggtgaagc cttcggagac cctgtccctc      60
acctgcactg tctctggggtt ttcattaacc agctatggtg tacactggat ccggcagccc    120
ccagggaagg gactggagtg gctgggggtc atatgggccg gtggaagcac aaattataat    180
ccctccctca agagtcgact gaccatatca aagacaacct ccaagagcca ggtttccctg    240

```
aagatgagct ctgtgaccgc tgcggacacg gccgtgtatt actgtgcgag agcctatggt    300
aactactggt acatcgatgt ctggggccaa gggaccacgg tcaccgtctc ctca          354
```

<210> SEQ ID NO 48
<211> LENGTH: 118
<212> TYPE: PRT
<213> ORGANISM: Artificial Sequence
<220> FEATURE:
<223> OTHER INFORMATION: 317-1 pro-Vh

<400> SEQUENCE: 48

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 49
<211> LENGTH: 321
<212> TYPE: DNA
<213> ORGANISM: Artificial Sequence
<220> FEATURE:
<223> OTHER INFORMATION: 317-1 cDNA-Vk

<400> SEQUENCE: 49

```
gacatcgtga tgacccagtc tccagactcc ctggctgtgt ctctgggcga gagggccacc    60
atcaactgca aggccagcca gagtgtgagt aatgatgtag cttggtacca gcagaaacca   120
ggacagcctc ctaagctgct cattaactat gcatttcatc gcttcactgg ggtccctgac   180
cgattcagtg gcagcgggta tgggacagat ttcactctca ccatcagcag cctgcaggct   240
gaagatgtgg cagtttatta ctgtcaccag gcttatagtt ctccgtacac gtttggcggg   300
gggaccaagc tggagatcaa a                                              321
```

<210> SEQ ID NO 50
<211> LENGTH: 107
<212> TYPE: PRT
<213> ORGANISM: Artificial Sequence
<220> FEATURE:
<223> OTHER INFORMATION: 317-1 pro-Vk

<400> SEQUENCE: 50

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45
```

```
Asn Tyr Ala Phe His Arg Phe Thr Gly Val Pro Asp Arg Phe Ser Gly
             50                  55                  60

Ser Gly Tyr Gly Thr Asp Phe Thr Leu Thr Ile Ser Ser Leu Gln Ala
 65                  70                  75                  80

Glu Asp Val Ala Val Tyr Tyr Cys His Gln Ala Tyr Ser Ser Pro Tyr
                 85                  90                  95

Thr Phe Gly Gly Gly Thr Lys Leu Glu Ile Lys
                100                 105
```

<210> SEQ ID NO 51
<211> LENGTH: 114
<212> TYPE: PRT
<213> ORGANISM: Artificial Sequence
<220> FEATURE:
<223> OTHER INFORMATION: 326-3B1 pro-Vh

<400> SEQUENCE: 51

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Lys Trp Met
             35                  40                  45

Gly Trp Ile Asn Asn Asn Asn Gly Glu Pro Thr Tyr Ala Gln Asp Phe
         50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
                100                 105                 110

Ser Ser
```

<210> SEQ ID NO 52
<211> LENGTH: 110
<212> TYPE: PRT
<213> ORGANISM: Artificial Sequence
<220> FEATURE:
<223> OTHER INFORMATION: 326-3B1 pro-Vk

<400> SEQUENCE: 52

```
Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Asp Asn Tyr
                 20                  25                  30

Gly Tyr Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Val Pro Ala
         50                  55                  60

Arg Phe Ser Gly Ser Gly Ser Arg Thr Asp Phe Thr Leu Thr Ile Asn
 65                  70                  75                  80

Pro Val Glu Ala Asn Asp Thr Ala Asn Tyr Tyr Cys Gln Gln Ser Lys
                 85                  90                  95

Glu Tyr Pro Thr Phe Gly Gly Gly Thr Lys Val Glu Ile Lys
                100                 105                 110
```

<210> SEQ ID NO 53

```
<211> LENGTH: 114
<212> TYPE: PRT
<213> ORGANISM: Artificial Sequence
<220> FEATURE:
<223> OTHER INFORMATION: 326-3G1 pro-Vh

<400> SEQUENCE: 53
```

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

```
<210> SEQ ID NO 54
<211> LENGTH: 110
<212> TYPE: PRT
<213> ORGANISM: Artificial Sequence
<220> FEATURE:
<223> OTHER INFORMATION: 326-3G1 pro-Vk

<400> SEQUENCE: 54
```

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

```
<210> SEQ ID NO 55
<211> LENGTH: 342
<212> TYPE: DNA
<213> ORGANISM: Artificial Sequence
<220> FEATURE:
<223> OTHER INFORMATION: 326-1 cDNA-Vh

<400> SEQUENCE: 55
```
caggtgcagc tggtgcagag cggcagcgag ctgaagaagc ccggcgccag cgtgaaggtg      60
agctgcaagg ccagcggcta caccttcacc aactacggca tgaactgggt gagacaggcc     120
cccggccagg gcctggagtg gatgggctgg atcaacaaca acaacggcga gcccacctac     180
gcccagggct tcagaggcag attcgtgttc agcctggaca ccagcgccag caccgcctac     240

```
ctgcagatca gcagcctgaa gaccgaggac accgccgtgt acttctgcgc cagagacgtg    300
atggactact ggggccaggg caccaccgtg accgtgagca gc                       342
```

<210> SEQ ID NO 56
<211> LENGTH: 114
<212> TYPE: PRT
<213> ORGANISM: Artificial Sequence
<220> FEATURE:
<223> OTHER INFORMATION: 326-1 pro-Vh

<400> SEQUENCE: 56

Gln Val Gln Leu Val Gln Ser Gly Ser Glu Leu Lys Lys Pro Gly Ala
1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Phe Cys
                85                  90                  95

Ala Arg Asp Val Met Asp Tyr Trp Gly Gln Gly Thr Thr Val Thr Val
            100                 105                 110

Ser Ser

<210> SEQ ID NO 57
<211> LENGTH: 330
<212> TYPE: DNA
<213> ORGANISM: Artificial Sequence
<220> FEATURE:
<223> OTHER INFORMATION: 326-1 cDNA-Vk

<400> SEQUENCE: 57

```
gacattgtgc tgacccagtc tccagcctcc ttggccgtgt ctccaggaca gagggccacc     60
atcacctgca gagccagtga aagtgttgat aattatggct atagttttat gcactggtat    120
cagcagaaac caggacaacc tcctaaactc ctgatttacc gtgcatccaa cctagaatct    180
ggggtcccag ccaggttcag cggcagtggg tctaggaccg atttcaccct cacaattaat    240
cctgtggaag ctaatgatac tgcaaattat tactgtcagc aaagtaaaga atatccgacg    300
ttcggcggag ggaccaaggt ggagatcaaa                                     330
```

<210> SEQ ID NO 58
<211> LENGTH: 110
<212> TYPE: PRT
<213> ORGANISM: Artificial Sequence
<220> FEATURE:
<223> OTHER INFORMATION: 326-1 pro-Vk

<400> SEQUENCE: 58

Asp Ile Val Leu Thr Gln Ser Pro Ala Ser Leu Ala Val Ser Pro Gly
1               5                  10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

```
Lys Leu Leu Ile Tyr Arg Ala Ser Asn Leu Glu Ser Gly Val Pro Ala
 50                  55                  60
Arg Phe Ser Gly Ser Gly Ser Arg Thr Asp Phe Thr Leu Thr Ile Asn
 65                  70                  75                  80
Pro Val Glu Ala Asn Asp Thr Ala Asn Tyr Tyr Cys Gln Gln Ser Lys
                 85                  90                  95
Glu Tyr Pro Thr Phe Gly Gly Gly Thr Lys Val Glu Ile Lys
            100                 105                 110

<210> SEQ ID NO 59
<211> LENGTH: 16
<212> TYPE: PRT
<213> ORGANISM: Artificial Sequence
<220> FEATURE:
<223> OTHER INFORMATION: 317-1 H-CDR2 or CDR-H2

<400> SEQUENCE: 59

Val Ile Trp Ala Gly Gly Ser Thr Asn Tyr Asn Pro Ser Leu Lys Ser
 1               5                  10                  15

<210> SEQ ID NO 60
<211> LENGTH: 16
<212> TYPE: PRT
<213> ORGANISM: Artificial Sequence
<220> FEATURE:
<223> OTHER INFORMATION: 317-4B2 H-CDR2 or CDR-H2

<400> SEQUENCE: 60

Val Ile Tyr Ala Gly Gly Ser Thr Asn Tyr Asn Pro Ser Leu Lys Ser
 1               5                  10                  15

<210> SEQ ID NO 61
<211> LENGTH: 11
<212> TYPE: PRT
<213> ORGANISM: Artificial Sequence
<220> FEATURE:
<223> OTHER INFORMATION: 317-4B2 L-CDR1 or CDR-L1

<400> SEQUENCE: 61

Lys Ser Ser Glu Ser Val Ser Asn Asp Val Ala
 1               5                  10

<210> SEQ ID NO 62
<211> LENGTH: 17
<212> TYPE: PRT
<213> ORGANISM: Artificial Sequence
<220> FEATURE:
<223> OTHER INFORMATION: 326-1 H-CDR2 or CDR-H2

<400> SEQUENCE: 62

Trp Ile Asn Asn Asn Asn Gly Glu Pro Thr Tyr Ala Gln Gly Phe Arg
 1               5                  10                  15
Gly

<210> SEQ ID NO 63
<211> LENGTH: 17
<212> TYPE: PRT
<213> ORGANISM: Artificial Sequence
<220> FEATURE:
<223> OTHER INFORMATION: 326-3G1 H-CDR2 or CDR-H2

<400> SEQUENCE: 63

Trp Ile Asn Asn Asn Asn Gly Glu Pro Thr Tyr Ala Gln Asp Phe Arg
 1               5                  10                  15
```

Gly

<210> SEQ ID NO 64
<211> LENGTH: 118
<212> TYPE: PRT
<213> ORGANISM: Artificial Sequence
<220> FEATURE:
<223> OTHER INFORMATION: 317-3A1 pro-Vh

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: 317-3C1 pro-Vh

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: 317-3E1 pro-Vh

<400> SEQUENCE: 66

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
             20                  25                  30

Gly Val His Trp Ile Arg Gln Pro Pro Gly Lys Gly Leu Glu Trp Ile
         35                  40                  45

Gly Val Ile Trp Ala Gly Gly Ser Thr Asn Tyr Asn Pro Ser Leu Lys
     50                  55                  60

Ser Arg Val Thr Ile Ser Val Asp Thr Ser Lys Ser Gln Phe Ser Leu
 65                  70                  75                  80

Lys Leu Ser Ser Val Thr Ala Ala Asp Thr Ala Val Tyr Tyr Cys Ala
             85                  90                  95

Arg Ala Tyr Gly Asn Tyr Trp Tyr Ile Asp Val Trp Gly Gln Gly Thr
             100                 105                 110

Thr Val Thr Val Ser Ser
            115

<210> SEQ ID NO 67
<211> LENGTH: 118
<212> TYPE: PRT
<213> ORGANISM: Artificial Sequence
<220> FEATURE:
<223> OTHER INFORMATION: 317-3F1 pro-Vh

<400> SEQUENCE: 67

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
             20                  25                  30

Gly Val His Trp Ile Arg Gln Pro Pro Gly Lys Gly Leu Glu Trp Ile
         35                  40                  45

Gly Val Ile Trp Ala Gly Gly Ser Thr Asn Tyr Asn Pro Ser Leu Lys
     50                  55                  60

Ser Arg Val Thr Ile Ser Val Asp Thr Ser Lys Asn Gln Val Ser Leu
 65                  70                  75                  80

Lys Leu Ser Ser Val Thr Ala Ala Asp Thr Ala Val Tyr Tyr Cys Ala
             85                  90                  95

Arg Ala Tyr Gly Asn Tyr Trp Tyr Ile Asp Val Trp Gly Gln Gly Thr
             100                 105                 110

Thr Val Thr Val Ser Ser
            115

<210> SEQ ID NO 68
<211> LENGTH: 118
<212> TYPE: PRT
<213> ORGANISM: Artificial Sequence
<220> FEATURE:
<223> OTHER INFORMATION: 317-3G1 pro-Vh

<400> SEQUENCE: 68

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
             20                  25                  30

Gly Val His Trp Ile Arg Gln Pro Pro Gly Lys Gly Leu Glu Trp Ile
         35                  40                  45

Gly Val Ile Trp Ala Gly Gly Ser Thr Asn Tyr Asn Pro Ser Leu Lys
```

```
                50                  55                  60
Ser Arg Val Thr Ile Ser Val Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: 317-3H1 pro-Vh

<400> SEQUENCE: 69

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Ile
            35                  40                  45

Gly Val Ile Trp Ala Gly Gly Ser Thr Asn Tyr Asn Pro Ser Leu Lys
     50                  55                  60

Ser Arg Val Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
        115

<210> SEQ ID NO 70
<211> LENGTH: 118
<212> TYPE: PRT
<213> ORGANISM: Artificial Sequence
<220> FEATURE:
<223> OTHER INFORMATION: 317-3I1 pro-Vh

<400> SEQUENCE: 70

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Ile
            35                  40                  45

Gly Val Ile Trp Ala Gly Gly Ser Thr Asn Tyr Asn Pro Ser Leu Lys
     50                  55                  60

Ser Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110
```

```
Thr Val Thr Val Ser Ser
        115

<210> SEQ ID NO 71
<211> LENGTH: 118
<212> TYPE: PRT
<213> ORGANISM: Artificial Sequence
<220> FEATURE:
<223> OTHER INFORMATION: 317-4B1 pro-Vh

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: 317-4B3 pro-Vh

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Asn Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: 317-4B4 pro-Vh
```

-continued

<400> SEQUENCE: 73

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Pro Tyr Ile Asp Val Trp Gly Gln Gly Thr
            100                 105                 110

Thr Val Thr Val Ser Ser
        115
```

<210> SEQ ID NO 74
<211> LENGTH: 107
<212> TYPE: PRT
<213> ORGANISM: Artificial Sequence
<220> FEATURE:
<223> OTHER INFORMATION: 317-4A2 pro-Vk

<400> SEQUENCE: 74

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105
```

<210> SEQ ID NO 75
<211> LENGTH: 114
<212> TYPE: PRT
<213> ORGANISM: Artificial Sequence
<220> FEATURE:
<223> OTHER INFORMATION: 326-3A1 pro-Vh

<400> SEQUENCE: 75

```
Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60
```

-continued

```
Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: 326-3C1 pro-Vh

<400> SEQUENCE: 76

Gln Val Gln Leu Val Gln Ser Gly Pro Glu Leu Lys Lys Pro Gly Ala
 1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Lys Trp Met
             35                  40                  45

Gly Trp Ile Asn Asn Asn Gly Glu Pro Thr Tyr Ala Gln Asp Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Val Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: 326-3D1 pro-Vh

<400> SEQUENCE: 77

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Glu Trp Met
             35                  40                  45

Gly Trp Ile Asn Asn Asn Gly Glu Pro Thr Tyr Ala Gln Gly Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
            100                 105                 110

Ser Ser

<210> SEQ ID NO 78
```

```
<211> LENGTH: 114
<212> TYPE: PRT
<213> ORGANISM: Artificial Sequence
<220> FEATURE:
<223> OTHER INFORMATION: 326-3E1 pro-Vh

<400> SEQUENCE: 78
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

```
<210> SEQ ID NO 79
<211> LENGTH: 114
<212> TYPE: PRT
<213> ORGANISM: Artificial Sequence
<220> FEATURE:
<223> OTHER INFORMATION: 326-3F1 pro-Vh

<400> SEQUENCE: 79
```

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

```
<210> SEQ ID NO 80
<211> LENGTH: 114
<212> TYPE: PRT
<213> ORGANISM: Artificial Sequence
<220> FEATURE:
<223> OTHER INFORMATION: 326-3B N55D pro-Vh

<400> SEQUENCE: 80
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

```
Gly Met Asn Trp Val Arg Gln Ala Pro Gly Gln Gly Leu Lys Trp Met
            35                  40                  45

Gly Trp Ile Asn Asn Asn Asp Gly Glu Pro Thr Tyr Ala Gln Asp Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
                100                 105                 110

Ser Ser

<210> SEQ ID NO 81
<211> LENGTH: 110
<212> TYPE: PRT
<213> ORGANISM: Artificial Sequence
<220> FEATURE:
<223> OTHER INFORMATION: 326-4A1 pro-Vk

<400> SEQUENCE: 81

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Asp Asn Tyr
             20                  25                  30

Gly Tyr Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Val Pro Ala
 50                  55                  60

Arg Phe Ser Gly Ser Gly Ser Arg Thr Asp Phe Thr Leu Thr Ile Asn
 65                  70                  75                  80

Pro Val Glu Ala Glu Asp Thr Ala Asn Tyr Tyr Cys Gln Gln Ser Lys
                 85                  90                  95

Glu Tyr Pro Thr Phe Gly Gly Gly Thr Lys Val Glu Ile Lys
                100                 105                 110

<210> SEQ ID NO 82
<211> LENGTH: 110
<212> TYPE: PRT
<213> ORGANISM: Artificial Sequence
<220> FEATURE:
<223> OTHER INFORMATION: 326-4A2 pro-Vk

<400> SEQUENCE: 82

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Asp Asn Tyr
             20                  25                  30

Gly Tyr Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln Gln Ser Lys
                 85                  90                  95

Glu Tyr Pro Thr Phe Gly Gly Gly Thr Lys Val Glu Ile Lys
                100                 105                 110
```

```
<210> SEQ ID NO 83
<211> LENGTH: 327
<212> TYPE: PRT
<213> ORGANISM: Artificial Sequence
<220> FEATURE:
<223> OTHER INFORMATION: huIgG4mt1 pro

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 84
<211> LENGTH: 327
<212> TYPE: PRT
<213> ORGANISM: Artificial Sequence
```

<220> FEATURE:
<223> OTHER INFORMATION: huIgG4mt2 pro

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 327
<212> TYPE: PRT
<213> ORGANISM: Artificial Sequence
<220> FEATURE:
<223> OTHER INFORMATION: huIgG4mt6 pro

<400> SEQUENCE: 85

Ala Ser Thr Lys Gly Pro Ser Val Phe Pro Leu Ala Pro Cys Ser Arg

```
                1               5                   10                  15
            Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Lys Thr
            65                  70                  75                  80

Tyr Thr Cys Asn Val Asp His Lys Pro Ser Asn Thr Lys Val Asp Lys
                            85                  90                  95

Arg Val Glu Ser Lys Tyr Gly Pro Pro Cys Pro Pro Cys Pro Ala Pro
                        100                 105                 110

Pro Val Ala Gly Gly Pro Ser Val Phe Leu Phe Pro Pro Lys Pro Lys
                        115                 120                 125

Asp Thr Leu Met Ile Ser Arg Thr Pro Glu Val Thr Cys Val Val Val
                    130                 135                 140

Ala Val Ser Gln Glu Asp Pro Glu Val Gln Phe Asn Trp Tyr Val Asp
            145                 150                 155                 160

Gly Val Glu Val His Asn Ala Lys Thr Lys Pro Arg Glu Glu Gln Phe
                                165                 170                 175

Asn Ser Thr Tyr Arg Val Val Ser Val Leu Thr Val Leu His Gln Asp
                            180                 185                 190

Trp Leu Asn Gly Lys Glu Tyr Lys Cys Lys Val Ser Asn Lys Gly Leu
                        195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
            225                 230                 235                 240

Asn Gln Val Ser Leu Thr Cys Leu Val Lys Gly Phe Tyr Pro Ser Asp
                            245                 250                 255

Ile Ala Val Glu Trp Glu Ser Asn Gly Gln Pro Glu Asn Asn Tyr Lys
                        260                 265                 270

Thr Thr Pro Pro Val Leu Asp Ser Asp Gly Ser Phe Phe Leu Tyr Ser
                        275                 280                 285

Arg Leu Thr Val Asp Lys Ser Arg Trp Gln Glu Gly Asn Val Phe Ser
                        290                 295                 300

Cys Ser Val Met His Glu Ala Leu His Asn His Tyr Thr Gln Lys Ser
            305                 310                 315                 320

Leu Ser Leu Ser Leu Gly Lys
                        325

<210> SEQ ID NO 86
<211> LENGTH: 327
<212> TYPE: PRT
<213> ORGANISM: Artificial Sequence
<220> FEATURE:
<223> OTHER INFORMATION: huIgG4mt8 pro

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Pro Val Ala Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Thr Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 87
<211> LENGTH: 327
<212> TYPE: PRT
<213> ORGANISM: Artificial Sequence
<220> FEATURE:
<223> OTHER INFORMATION: huIgG4mt9 pro

<400> SEQUENCE: 87

Ala Ser Thr Lys Gly Pro Ser Val Phe Pro Leu Ala Pro Cys Ser Arg
 1                   5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                    85                  90                  95
Arg Val Glu Ser Lys Tyr Gly Pro Pro Cys Pro Pro Cys Pro Ala Pro
                100                 105                 110
Pro Val Ala Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
            130                 135                 140
Ala Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
            275                 280                 285
Lys Leu Thr Val Asp Lys Ser Arg Trp Gln Glu Gly Asn Val Phe Ser
        290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 88
<211> LENGTH: 327
<212> TYPE: PRT
<213> ORGANISM: Artificial Sequence
<220> FEATURE:
<223> OTHER INFORMATION: huIgG4mt10 pro

<400> SEQUENCE: 88

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
```

```
                100                 105                 110
Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 367
<212> TYPE: PRT
<213> ORGANISM: Artificial Sequence
<220> FEATURE:
<223> OTHER INFORMATION: OS8 pro

<400> SEQUENCE: 89

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
                20                  25                  30

Pro Gly Ala Ser Val Lys Met Ser Cys Lys Ala Ser Gly Tyr Thr Phe
            35                  40                  45

Thr Arg Tyr Thr Met His Trp Val Lys Gln Arg Pro Gly Gln Gly Leu
50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Ser Gly Gly Gly Gly Ser Gly
```

```
                130             135             140
Gly Gly Gly Ser Gly Gly Gly Ser Gln Ile Val Leu Thr Gln Ser
145             150             155             160

Pro Ala Ile Met Ser Ala Ser Pro Gly Glu Lys Val Thr Met Thr Cys
                165             170             175

Ser Ala Ser Ser Ser Val Ser Tyr Met Asn Trp Tyr Gln Gln Lys Ser
            180             185             190

Gly Thr Ser Pro Lys Arg Trp Ile Tyr Asp Thr Ser Lys Leu Ala Ser
        195             200             205

Gly Val Pro Ala His Phe Arg Gly Ser Gly Ser Gly Thr Ser Tyr Ser
    210             215             220

Leu Thr Ile Ser Gly Met Glu Ala Glu Asp Ala Ala Thr Tyr Tyr Cys
225             230             235             240

Gln Gln Trp Ser Ser Asn Pro Phe Thr Phe Gly Ser Gly Thr Lys Leu
                245             250             255

Glu Ile Asn Ser Ser Val Val Pro Val Leu Gln Lys Val Asn Ser Thr
            260             265             270

Thr Thr Lys Pro Val Leu Arg Thr Pro Ser Pro Val His Pro Thr Gly
        275             280             285

Thr Ser Gln Pro Gln Arg Pro Glu Asp Cys Arg Pro Arg Gly Ser Val
    290             295             300

Lys Gly Thr Gly Leu Asp Phe Ala Cys Asp Ile Tyr Ile Trp Ala Pro
305             310             315             320

Leu Ala Gly Ile Cys Val Ala Leu Leu Leu Ser Leu Ile Ile Thr Leu
                325             330             335

Ile Cys Tyr His Arg Ser Arg Lys Arg Val Cys Lys Cys Pro Arg Pro
            340             345             350

Leu Val Arg Gln Glu Gly Lys Pro Arg Pro Ser Glu Lys Ile Val
        355             360             365

<210> SEQ ID NO 90
<211> LENGTH: 304
<212> TYPE: PRT
<213> ORGANISM: Artificial Sequence
<220> FEATURE:
<223> OTHER INFORMATION: P3Z pro

<400> SEQUENCE: 90

Met Gln Ile Pro Gln Ala Pro Trp Pro Val Val Trp Ala Val Leu Gln
1               5               10              15

Leu Gly Trp Arg Pro Gly Trp Phe Leu Asp Ser Pro Asp Arg Pro Trp
            20              25              30

Asn Pro Pro Thr Phe Ser Pro Ala Leu Leu Val Val Thr Glu Gly Asp
        35              40              45

Asn Ala Thr Phe Thr Cys Ser Phe Ser Asn Thr Ser Glu Ser Phe Val
    50              55              60

Leu Asn Trp Tyr Arg Met Ser Pro Ser Asn Gln Thr Asp Lys Leu Ala
65              70              75              80

Ala Phe Pro Glu Asp Arg Ser Gln Pro Gly Gln Asp Cys Arg Phe Arg
                85              90              95

Val Thr Gln Leu Pro Asn Gly Arg Asp Phe His Met Ser Val Val Arg
            100             105             110

Ala Arg Arg Asn Asp Ser Gly Thr Tyr Leu Cys Gly Ala Ile Ser Leu
        115             120             125

Ala Pro Lys Ala Gln Ile Lys Glu Ser Leu Arg Ala Glu Leu Arg Val
```

```
                130             135             140
Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
                180                 185                 190

Val Lys Phe Ser Arg Ser Ala Asp Ala Pro Ala Tyr Gln Gln Gly Gln
                195                 200                 205

Asn Gln Leu Tyr Asn Glu Leu Asn Leu Gly Arg Arg Glu Glu Tyr Asp
                210                 215                 220

Val Leu Asp Lys Arg Arg Gly Arg Asp Pro Glu Met Gly Gly Lys Pro
225                 230                 235                 240

Gln Arg Arg Lys Asn Pro Gln Glu Gly Leu Tyr Asn Glu Leu Gln Lys
                245                 250                 255

Asp Lys Met Ala Glu Ala Tyr Ser Glu Ile Gly Met Lys Gly Glu Arg
                260                 265                 270

Arg Arg Gly Lys Gly His Asp Gly Leu Tyr Gln Gly Leu Ser Thr Ala
                275                 280                 285

Thr Lys Asp Thr Tyr Asp Ala Leu His Met Gln Ala Leu Pro Pro Arg
                290                 295                 300

<210> SEQ ID NO 91
<211> LENGTH: 327
<212> TYPE: PRT
<213> ORGANISM: Artificial Sequence
<220> FEATURE:
<223> OTHER INFORMATION: IgG4 Fc region 228P-233P

<400> SEQUENCE: 91

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Glu Phe Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 92
<211> LENGTH: 327
<212> TYPE: PRT
<213> ORGANISM: Artificial Sequence
<220> FEATURE:
<223> OTHER INFORMATION: IgG4 Fc region 228P-234V

<400> SEQUENCE: 92

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Val Phe Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
```

```
            225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 93
<211> LENGTH: 327
<212> TYPE: PRT
<213> ORGANISM: Artificial Sequence
<220> FEATURE:
<223> OTHER INFORMATION: IgG4 Fc region 228P-235A

<400> SEQUENCE: 93

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Ala Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

```
                    260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 94
<211> LENGTH: 327
<212> TYPE: PRT
<213> ORGANISM: Artificial Sequence
<220> FEATURE:
<223> OTHER INFORMATION: IgG4 Fc region 228P-234V-235A

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                    290                 295                 300
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 95
<211> LENGTH: 327
<212> TYPE: PRT
<213> ORGANISM: Artificial Sequence
<220> FEATURE:
<223> OTHER INFORMATION: IgG4 Fc region 228P-234A

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Phe Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 96
<211> LENGTH: 327
<212> TYPE: PRT
<213> ORGANISM: Artificial Sequence
<220> FEATURE:
<223> OTHER INFORMATION: IgG4 Fc region 228P-234A-235A

<400> SEQUENCE: 96

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 97
<211> LENGTH: 327
<212> TYPE: PRT

<213> ORGANISM: Artificial Sequence
<220> FEATURE:
<223> OTHER INFORMATION: IgG4 Fc region 228P-233P-234A-235A

<400> SEQUENCE: 97

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
| | | | 20 | | | | 25 | | | | 30 | | | | |

| Phe | Pro | Glu | Pro | Val | Thr | Val | Ser | Trp | Asn | Ser | Gly | Ala | Leu | Thr | Ser |
| | | 35 | | | | 40 | | | | 45 | | | | | |

| Gly | Val | His | Thr | Phe | Pro | Ala | Val | Leu | Gln | Ser | Ser | Gly | Leu | Tyr | Ser |
| | 50 | | | | 55 | | | | 60 | | | | | | |

| Leu | Ser | Ser | Val | Val | Thr | Val | Pro | Ser | Ser | Ser | Leu | Gly | Thr | Lys | Thr |
| 65 | | | | 70 | | | | 75 | | | | 80 | | | |

| Tyr | Thr | Cys | Asn | Val | Asp | His | Lys | Pro | Ser | Asn | Thr | Lys | Val | Asp | Lys |
| | | | 85 | | | | 90 | | | | 95 | | | | |

| Arg | Val | Glu | Ser | Lys | Tyr | Gly | Pro | Pro | Cys | Pro | Pro | Cys | Pro | Ala | Pro |
| | | 100 | | | | 105 | | | | 110 | | | | | |

| Pro | Ala | Ala | Gly | Gly | Pro | Ser | Val | Phe | Leu | Phe | Pro | Pro | Lys | Pro | Lys |
| | 115 | | | | 120 | | | | 125 | | | | | | |

| Asp | Thr | Leu | Met | Ile | Ser | Arg | Thr | Pro | Glu | Val | Thr | Cys | Val | Val | Val |
| 130 | | | | | 135 | | | | 140 | | | | | | |

| Asp | Val | Ser | Gln | Glu | Asp | Pro | Glu | Val | Gln | Phe | Asn | Trp | Tyr | Val | Asp |
| 145 | | | | 150 | | | | 155 | | | | 160 | | | |

| Gly | Val | Glu | Val | His | Asn | Ala | Lys | Thr | Lys | Pro | Arg | Glu | Glu | Gln | Phe |
| | | | 165 | | | | 170 | | | | 175 | | | | |

| Asn | Ser | Thr | Tyr | Arg | Val | Val | Ser | Val | Leu | Thr | Val | Leu | His | Gln | Asp |
| | | 180 | | | | 185 | | | | 190 | | | | | |

| Trp | Leu | Asn | Gly | Lys | Glu | Tyr | Lys | Cys | Lys | Val | Ser | Asn | Lys | Gly | Leu |
| | 195 | | | | 200 | | | | 205 | | | | | | |

| Pro | Ser | Ser | Ile | Glu | Lys | Thr | Ile | Ser | Lys | Ala | Lys | Gly | Gln | Pro | Arg |
| 210 | | | | | 215 | | | | 220 | | | | | | |

| Glu | Pro | Gln | Val | Tyr | Thr | Leu | Pro | Pro | Ser | Gln | Glu | Glu | Met | Thr | Lys |
| 225 | | | | 230 | | | | 235 | | | | 240 | | | |

| Asn | Gln | Val | Ser | Leu | Thr | Cys | Leu | Val | Lys | Gly | Phe | Tyr | Pro | Ser | Asp |
| | | | 245 | | | | 250 | | | | 255 | | | | |

| Ile | Ala | Val | Glu | Trp | Glu | Ser | Asn | Gly | Gln | Pro | Glu | Asn | Asn | Tyr | Lys |
| | | 260 | | | | 265 | | | | 270 | | | | | |

| Thr | Thr | Pro | Pro | Val | Leu | Asp | Ser | Asp | Gly | Ser | Phe | Phe | Leu | Tyr | Ser |
| | 275 | | | | 280 | | | | 285 | | | | | | |

| Arg | Leu | Thr | Val | Asp | Lys | Ser | Arg | Trp | Gln | Glu | Gly | Asn | Val | Phe | Ser |
| 290 | | | | 295 | | | | 300 | | | | | | | |

| Cys | Ser | Val | Met | His | Glu | Ala | Leu | His | Asn | His | Tyr | Thr | Gln | Lys | Ser |
| 305 | | | | 310 | | | | 315 | | | | 320 | | | |

| Leu | Ser | Leu | Ser | Leu | Gly | Lys |
| | | | | 325 | | |

<210> SEQ ID NO 98
<211> LENGTH: 327
<212> TYPE: PRT
<213> ORGANISM: Artificial Sequence
<220> FEATURE:
<223> OTHER INFORMATION: IgG4 Fc region 228P-234V-235A-265A

<400> SEQUENCE: 98

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 99
<211> LENGTH: 327
<212> TYPE: PRT
<213> ORGANISM: Artificial Sequence
<220> FEATURE:
<223> OTHER INFORMATION: IgG4 Fc region 228P-234A-235A-265A

<400> SEQUENCE: 99

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 100
<211> LENGTH: 327
<212> TYPE: PRT
<213> ORGANISM: Artificial Sequence
<220> FEATURE:
<223> OTHER INFORMATION: IgG4 Fc region 228P-233P-234A-235A-265A

<400> SEQUENCE: 100

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 101
<211> LENGTH: 327
<212> TYPE: PRT
<213> ORGANISM: Artificial Sequence
<220> FEATURE:
<223> OTHER INFORMATION: IgG4 Fc region 228P-265A

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Cys Pro Ala Pro
                100             105             110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 102
<211> LENGTH: 327
<212> TYPE: PRT
<213> ORGANISM: Artificial Sequence
<220> FEATURE:
<223> OTHER INFORMATION: IgG4 Fc region 228P-309V

<400> SEQUENCE: 102

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100             105             110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 103
<211> LENGTH: 327
<212> TYPE: PRT
<213> ORGANISM: Artificial Sequence
<220> FEATURE:
<223> OTHER INFORMATION: IgG4 Fc region 228P-409K

<400> SEQUENCE: 103

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 104
<211> LENGTH: 327
<212> TYPE: PRT
<213> ORGANISM: Artificial Sequence
<220> FEATURE:
<223> OTHER INFORMATION: IgG4 Fc region 228P-309V-409K

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 105
<211> LENGTH: 327
<212> TYPE: PRT
<213> ORGANISM: Artificial Sequence
<220> FEATURE:
<223> OTHER INFORMATION: IgG4 Fc region 228P-265A-309V-409K

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Val His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 106
<211> LENGTH: 327
<212> TYPE: PRT
<213> ORGANISM: Artificial Sequence
<220> FEATURE:
<223> OTHER INFORMATION: IgG4 Fc region 228P-233P-234A-235A-265A-309V-
      409K

<400> SEQUENCE: 106

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

Ile Ala Val Glu Trp Glu Ser Asn Gly Gln Pro Glu Asn Asn Tyr Lys
          260                 265                 270

Thr Thr Pro Pro Val Leu Asp Ser Asp Gly Ser Phe Phe Leu Tyr Ser
      275                 280                 285

Lys Leu Thr Val Asp Lys Ser Arg Trp Gln Glu Gly Asn Val Phe Ser
  290                 295                 300

Cys Ser Val Met His Glu Ala Leu His Asn His Tyr Thr Gln Lys Ser
305                 310                 315                 320

Leu Ser Leu Ser Leu Gly Lys
              325

<210> SEQ ID NO 107
<211> LENGTH: 327
<212> TYPE: PRT
<213> ORGANISM: Homo sapiens

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser

```
            290                 295                 300
Cys Ser Val Met His Glu Ala Leu His Asn His Tyr Thr Gln Lys Ser
305                 310                 315                 320

Leu Ser Leu Ser Leu Gly Lys
                325
```